(12) United States Patent
Park et al.

(10) Patent No.: US 7,332,233 B2
(45) Date of Patent: Feb. 19, 2008

(54) IRIDIUM COMPOUND AND ORGANIC ELECTROLUMINESCENT DEVICE USING THE SAME

(75) Inventors: Soo-Jin Park, Seoul (KR); Kwan-Hee Lee, Seoul (KR); Dong-Hyun Jung, Suwon-si (KR); Dae-Yup Shin, Suwon-si (KR); Tae-Hyok Kwon, Seoul (KR); Jong-In Hong, Seoul (KR)

(73) Assignee: Samsung SDI Co., Ltd., Suwon (KR)

( * ) Notice: Subject to any disclaimer, the term of this patent is extended or adjusted under 35 U.S.C. 154(b) by 339 days.

(21) Appl. No.: 10/912,287

(22) Filed: Aug. 6, 2004

(65) Prior Publication Data

US 2005/0031903 A1    Feb. 10, 2005

(30) Foreign Application Priority Data

Aug. 7, 2003   (KR) .................. 10-2003-0054778
Feb. 17, 2004  (KR) .................. 10-2004-0010414

(51) Int. Cl.
*H01L 51/54* (2006.01)
*C09K 11/06* (2006.01)

(52) U.S. Cl. ................. 428/690; 428/917; 313/504; 548/103; 548/106; 257/E51.044

(58) Field of Classification Search ............... 548/103, 548/106
See application file for complete search history.

(56) References Cited

U.S. PATENT DOCUMENTS

2001/0019782 A1* 9/2001 Igarashi et al. ............ 428/690
2002/0034656 A1* 3/2002 Thompson et al. ......... 428/690
2002/0063516 A1* 5/2002 Tsuboyama et al. ....... 313/504
2004/0048101 A1* 3/2004 Thompson et al. ......... 428/690

FOREIGN PATENT DOCUMENTS

EP       1 239 526 A2    9/2002
KR       2002-0070299 A   9/2002

OTHER PUBLICATIONS

Arnold B. Tamayo, et al., Synthesis and Characterization of Facial and Meridional Tris-cyclometalated Iridium(III) Complexes, J. Am. Chem. Soc., vol. 125, pp. 7377-7387, Jun. 18, 2003.
Chihaya Adachi, et al., Endothermic Energy Transfer: A mechanism for generating very efficient high-energy phosphorescent emission in organic materials, Appl. Phys, Lett, vol. 79, pp. 2082-2084, Sep. 24, 2001.
S. A. Stockman, J. M. Redwing, M. E. Thompson, S. R. Forest, D. J. Gisser, G. C. Lisensky, K. J. Nordell, S. M. Condren, J. G. Breitzer, C. G. Windstrand, A. B. Ellis; New Lamps For Old. Opportunities For Chemists In Lighting And Display Technologies, Seminar material sponsored by Materials Research Science and Engineering Center for Nanostructured Materials and Interfaces University of Wisconsin—Madison, Apr. 1, 2001.

* cited by examiner

*Primary Examiner*—Marie Yamnitzky
(74) *Attorney, Agent, or Firm*—H.C. Park & Associates, PLC

(57) ABSTRACT

A blue phosphorescent compound and an organic electroluminescent device using the same are provided. The blue phosphorescent compound can emit deep blue light and can improve color purity and reduce power consumption when used in an organic electroluminescent device.

3 Claims, 27 Drawing Sheets

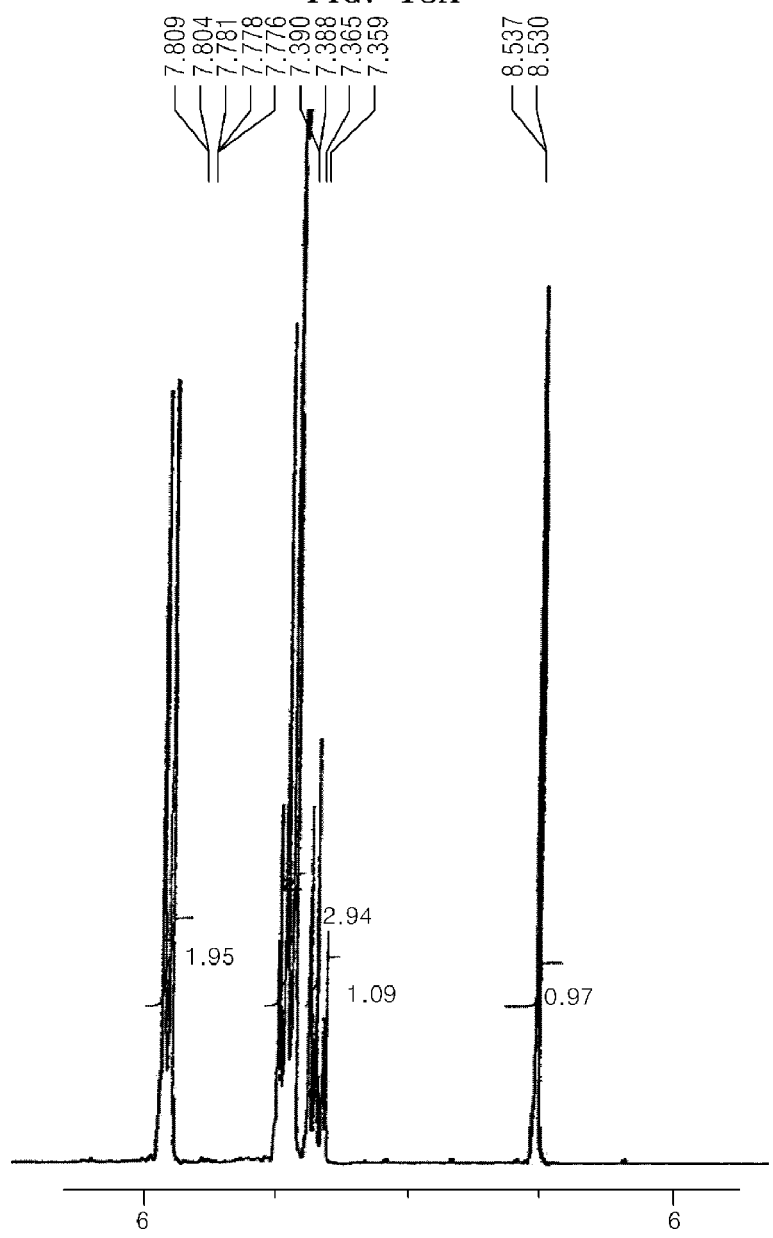

IRIDIUM COMPOUND AND ORGANIC ELECTROLUMINESCENT DEVICE USING THE SAME

BACKGROUND OF THE INVENTION

This application claims priority from Korean Patent Application No. 2003-54778, filed on Aug. 7, 2003, and No. 2004-10414, filed on Feb. 17, 2004 in the Korean Intellectual Property Office, the disclosures of which are incorporated herein in their entirety by reference.

1. Field of the Invention

The present invention relates to an organometallic compound that contains iridium (Ir) and an organic electroluminescent device using the same, and more particularly, to an iridium compound that may be used as a blue phosphorescent material and an organic electroluminescent device using the same.

2. Description of the Related Art

Electroluminescent (EL) devices, known as self-luminous displays, have the advantages of large viewing angle, high contrast, and short response time. EL devices can be classified depending on the material used for the emissive layer as inorganic or organic EL devices. As compared with inorganic EL devices, organic EL devices have the advantages of higher luminance, lower driving voltage, shorter response time, and the ability to display a wider range of colors.

A typical organic EL device includes an anode on the top surface of a substrate. A hole transporting layer, an emissive layer, an electron transporting layer, and a cathode are formed sequentially on the anode. The hole transporting layer, the emissive layer, and the electron transporting layer are thin films made of organic compounds.

Organic EL devices with the above-described structure operate according to the following principles. When a voltage is applied across the anode and the cathode, holes injected from the anode migrate via the hole transporting layer into the emissive layer. Electrons injected from the cathode migrate via the electron transporting layer into the emissive layer and combine with the holes therein to generate exitons. When the exitons transit from excited state to base state, molecules in the emissive layer emit light to form visible images.

Materials for the emissive layer can be classified depending on their light emission mechanism as fluorescent materials that emit light from exitons in a singlet state or phosphorescent materials that emit light from exitons in a triplet state. In general, phosphorescent materials are organometallic compounds that contain a heavy atom and an organic ligand. In phosphorescence from phosphorescent materials, exitons which are in a non-emissive triplet state due to the heavy atom are allowed to change state and participate in emission. Such phosphorescent materials use 75% of triplet state exitons for emission and offer higher luminescent efficiency compared to fluorescent materials that use only 25% of singlet state exitions for emission.

A number of triple state phosphorescent materials, such as metallic compounds, for example, iridium and platinum, have been reported. Blue phosphorescent materials developed so far include (4,6-F2 ppy)2Irpic, Ir compounds with a fluorinated ppy ligand structure, etc. However, these materials emit light in a sky blue range and lack suitable host materials, thereby leading to very low efficiency and short lifetime compared to red and green phosphorescent materials. Therefore, there is an urgent need for the development of deep blue, high-efficiency, long lifespan phosphorescent materials.

SUMMARY OF THE INVENTION

Embodiments of the present invention provide a deep blue phosphorescent compound that has improved color purity and consumes less power than conventional blue phosphorescent materials, and a metallic phosphorescent compound containing a new ligand.

Embodiments of the present invention also provide an organic electroluminescent (EL) device using the compound and having improved luminescent efficiency, color purity, and consumption power One aspect of the present invention provides an iridium compound of formula (1) below:

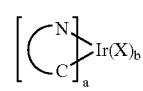 (1)

in which:

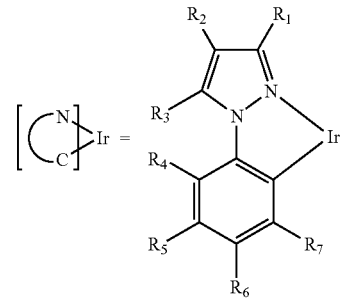

where $R_1$, $R_2$, $R_3$, $R_4$, $R_5$, $R_6$, and $R_7$ are independently selected from the group consisting of a halogen atom, a cyano group, a hydroxy group, a thiol group, a halogen atom, a substituted or unsubstituted C1-C30 alkyl group, a substituted or unsubstituted C1-C30 alkoxy group, a substituted or unsubstituted C2-C30 alkenyl group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C30 cycloalkyl group, a substituted or unsubstituted C2-C30 heterocycloalkyl group, a C1-C30 alkylthio group, —Si(R')(R")(R''') where each of R', R" and R''' is independently a hydrogen atom or a C1-C30 alkyl group, and —N(R')(R") where each of R' and R" is independently a hydrogen atom or a C1-C30 alkyl group, wherein at least two among $R_1$, $R_2$, $R_3$, $R_4$, $R_5$, $R_6$, and $R_7$ can be combined together; X is a monoanionic, bidentate ligand; a is an integer from 1 to 3; b is an integer from 0 to 2; and the sum of a and b equals to 3, wherein all of $R_1$, $R_2$, $R_3$, $R_4$, $R_5$, $R_6$, and $R_7$ are hydrogen when a=3 and b=0, and all of $R_1$, $R_2$, $R_3$, $R_4$, and $R_7$ are hydrogen when both $R_5$ and $R_6$ are fluorine, X is picolinate (pic), a=2, and b=1, are excluded.

Another aspect of the present invention provides a metallic compound having a bidentate ligand of formula (31) below:

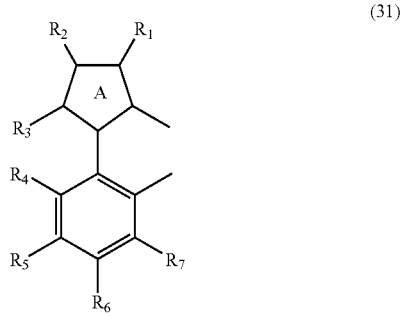

in which:

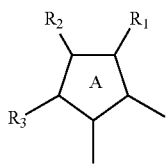

is selected from the group consisting of

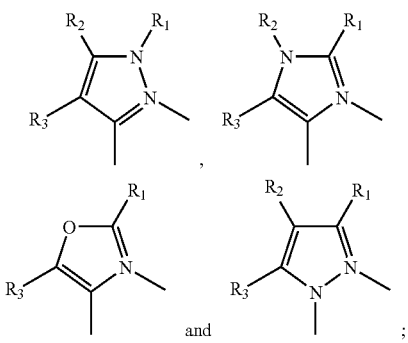

$R_1$, $R_2$, $R_3$, $R_4$, $R_5$, $R_6$, and $R_7$ are independently selected from the group consisting of a hydrogen atom, a cyano group, a hydroxy group, a thiol group, a halogen atom, a substituted or unsubstituted C1-C30 alkyl group, a substituted or unsubstituted C1-C30 alkoxy group, a substituted or unsubstituted C2-C30 alkenyl group, a substituted or unsubstituted $C_6$-$C_{30}$ aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C30 cycloalkyl group, a substituted or unsubstituted C2-C30 heterocycloalkyl group, a substituted or unsubstituted C1-C30 alkylcarbonyl group, a substituted or unsubstituted C7-C30 arylcarbonyl group, a C1-C30 alkylthio group, —Si(R')(R'')(R''') in which each of R', R'', and R''' is independently a hydrogen atom or a C1-C30 alkyl group, and —N(R')(R'') in which each of R' and R'' is independently a hydrogen atom or a C1-C30 alkyl group, wherein at least two among $R_1$, $R_2$, $R_3$, $R_4$, $R_5$, $R_6$, and $R_7$ can be combined together, and adjacent substituted groups form an unsaturated or saturated ring.

Another aspect of the present invention provides an organic EL device that includes an organic film containing the above-described compound between a pair of electrodes.

BRIEF DESCRIPTION OF THE DRAWINGS

The above and other features and aspects of the present invention will become more apparent by describing in detail exemplary embodiments thereof with reference to the attached drawings in which:

FIG. 13A is the NMR spectrum of a compound of formula (A-1) according to the embodiments of the present invention in $CHCl_3$ solution;

DETAILED DESCRIPTION OF THE INVENTION

Figure 1:
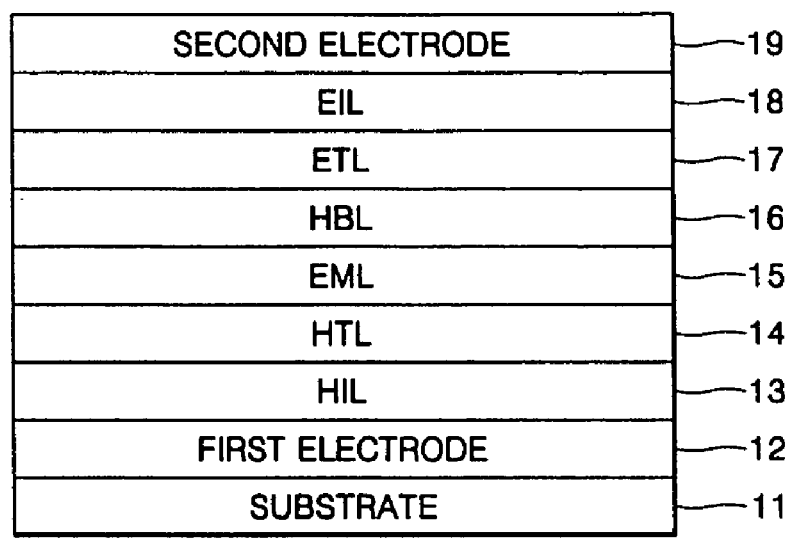
FIG. 1 is a sectional view illustrating a structure of a typical organic electroluminescent (EL) device in accordance with embodiments of the present invention.

Embodiments of the present invention provide an iridium compound of formula (1) below that emits deeper blue light than conventional blue luminescent molecules and may be used as a blue phosphorescent dopant for full-color organic electroluminescent devices:

in which:

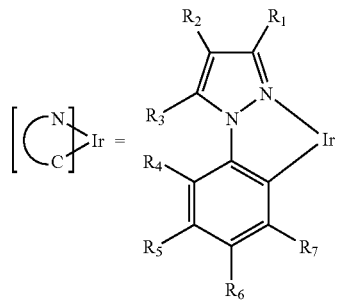

and in which $R_1$, $R_2$, $R_3$, $R_4$, $R_5$, $R_6$, and $R_7$ are independently selected from the group consisting of a hydrogen atom, a cyano group, a hydroxy group, a thiol group, a halogen atom, a substituted or unsubstituted C1-C30 alkyl group, a substituted or unsubstituted C1-C30 alkoxy group, a substituted or unsubstituted C2-C30 alkenyl group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C2-C30 heterocycloalkyl group, a C1-C20 alkylthio group, —Si(R')(R")(R''') in which each of R', R" and R''' is independently a hydrogen atom or a C1-C30 alkyl group, and —N(R') (R") in which each of R' and R" is independently a hydrogen atom or a C1-C30 alkyl group, wherein at least two among $R_1$, $R_2$, $R_3$, $R_4$, $R_5$, $R_6$, and $R_7$ are combined together;

X is a monoanionic, bidentate ligand;

a is an integer from 1 to 3; b is an integer from 0 to 2; and the sum of a and b equals to 3, wherein the following cases are excluded: all of $R_1$, $R_2$, $R_3$, $R_4$, $R_5$, $R_6$, and $R_7$ are hydrogen, a=3, and b=0, and all of $R_1$, $R_2$, $R_3$, $R_4$, and $R_7$ are hydrogen, both of $R_5$ and $R_6$ are fluorine, X is picolinate (pic), a=2, and b=1.

At least two selected among from $R_1$, $R_2$, $R_3$, $R_4$, $R_5$, $R_6$, and $R_7$
  may be combined together to form a cyclic system. For example, $R_1$ and $R_2$; $R_2$ and $R_3$; $R_1$, $R_2$, and $R_3$; $R_4$ and $R_5$; $R_5$ and $R_6$; $R_4$, $R_5$, and $R_6$; $R_6$ and $R_7$; or $R_5$, $R_6$, and $R_7$ may be combined to form a cyclic system.

The iridium compound of formula (1) may be expressed by formula 2a or 2b below depending on the combination of a and b. Formula 2b represents an iridium compound with a=3 and b=0, and formula 2c represents an iridium compound with a=2 and b=1.

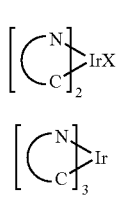
(2a)

(2b)

Examples of X in formula (1) above include acetylacetonate (acac), hexafluoroacetylacetonate (hfacac), salicylidene (sal), picolinate (pic), 8-hydroxyquinolinate (hquin), α-amino acid L-proline (L-pro), dibenzoylmethane (dbm), tetrametylheptanedionate (tmd), 1-(2-hydoxyphenyl)pyrazolate (oppz), 3-isoquinolinecarboxylate (3iq), 1-isoquinolinecarboxylate (1iq), 1,5-dimethyl-3-pyrazolecarboxylate (dm3PC), phenylpyrazole (ppz), quinolinecarboxylate (quin) and phenylpyridine (ppy), which have the following formulae:

acac
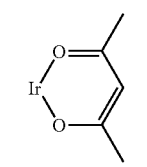

hfacac
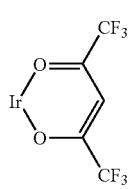

tmd
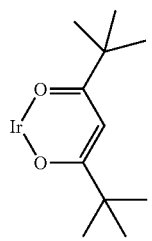

dbm
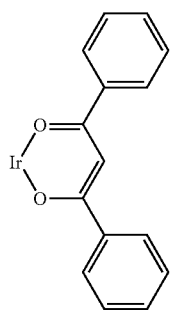

pic
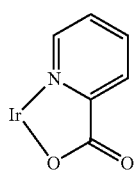

-continued quin
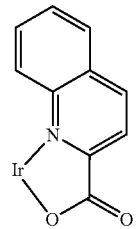

L-pro
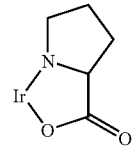

oppz
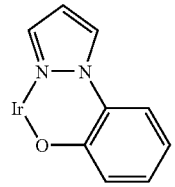

3iq
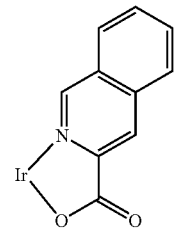

ppz
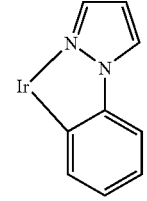

sal
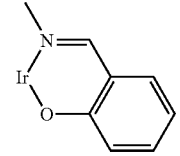

hquin
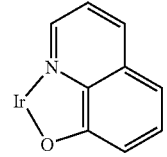

dm3PC
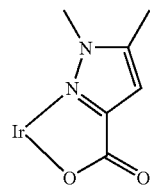

-continued

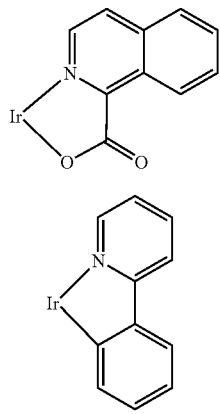

liq ppy

In formula (1) above, $R_1$, $R_2$, $R_3$, $R_4$, $R_5$, $R_6$, and $R_7$ may be independently selected from among a methyl group, an ethyl group, a propyl group, an n-butyl group, an isopropyl group, a tert-butyl group, a sec-butyl group, a tert-amyl group, a trifluoromethyl group, a pentafluoroethyl group, a perfluoroalkyl group, a benzyl group, 4-(tert-butyl)benzyl, 3,5-di-(tert-butyl)benzyl, 3,5-di-(isopropyl)benzyl, a naphthyl group, a phenyl group, a furyl group, a thienyl group, a pyridyl group, a cyano group, a methoxy group, an ethoxy group, and a halogen atom, with the halogen atom, the methyl group, the ethyl group, the propyl group, the phenyl group, and the cyano group being preferred.

In the iridium compound of formula (1) according to the embodiments of the present invention, $R_1$, $R_2$, and $R_3$ may be independently methyl or ethyl, and $R_4$, $R_5$, $R_6$, and $R_7$ may be independently selected from among a halogen atom, a methyl group, an ethyl group, a phenyl group, and a cyano group. Examples of these iridium compounds include:

in which all of $R_8$, $R_9$, $R_{10}$, $R_{11}$ and $R_{17}$ are methyl groups, $R_{14}$ and $R_{18}$ is a methyl group, a phenyl group, a cyano group, a methoxy group or a halogen atom, and each of $R_{12}$, $R_{13}$, $R_{15}$ and $R_{16}$ is independently a methyl group, a phenyl group, a cyano group, a methoxy group or a halogen atom.

Figure 8:
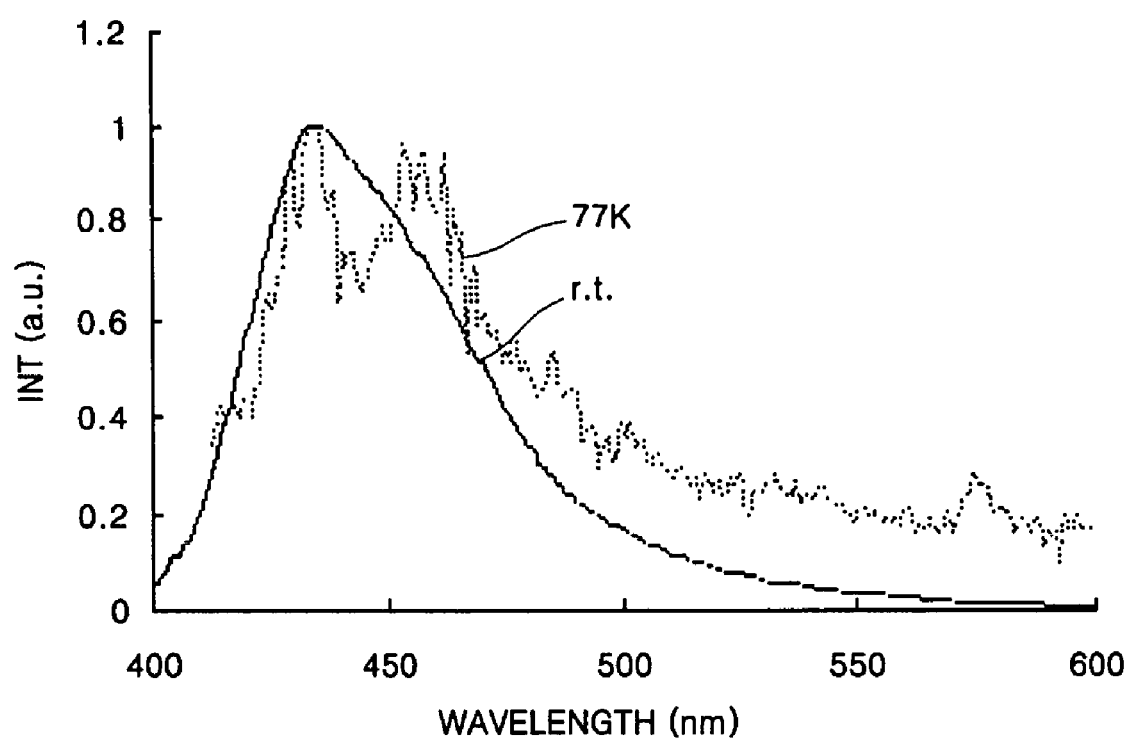
FIG. 8 is the PL spectra of the iridium compound of formula (11) in $CH_2Cl_2$ solution at room temperature and 77K.

The iridium compound of formula (1) according to the embodiments of the present invention is a deep blue luminescent material. The ability of the iridium compound of formula (1) to emit deep blue light is attributed to a pyrazol 5-membered ring structure in the ppy ligand that is transformed from a pyridine 6-membered ring structure that appears in conventional materials. The pyrazol 5-membered ring structure with shorter p-conjugation length and greater bandgap energy (Eg) leads to blue shifting. In particular, the introduction of —CN substituent as an electron withdrawing group into a phenyl ring increases the molecular repulsion and volatility, thereby allowing for easy deposition. The —CN substituent also hinders molecular interactions, thereby suppressing concentration dilution effects and crystallization and raising film stability and emission efficiency. The substitution of a phenyl group with an aromatic ring substituent raises thermal stability, film stability, and emission efficiency. The introduction of an alkyl group, such as methyl, leads to a steric hindrance effect and reduces molecular interactions, thereby preventing concentration dilution effects that appear due to molecular interactions. As a result, the emission efficiency is greatly improved as shown in FIG. 8. The reduced molecular interaction suppresses crystallization in thin films and improves the properties of the thin films, thereby resulting in a greater emission efficiency.

Examples of the iridium compound of formula (1) include compounds of formulae (4) through (24) below.

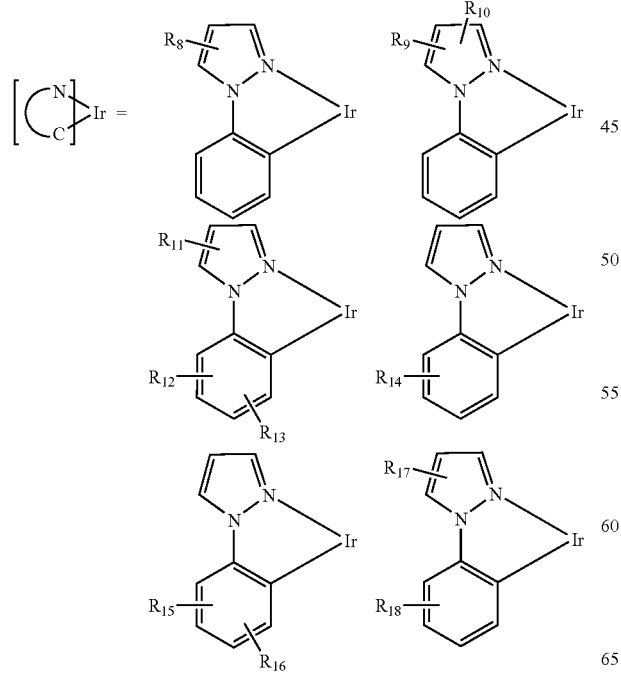

(4)

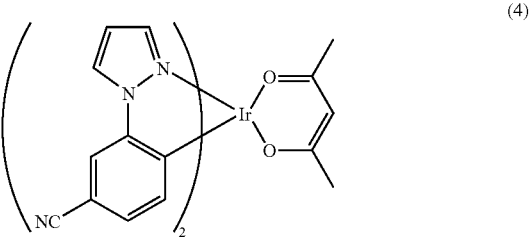

(5)

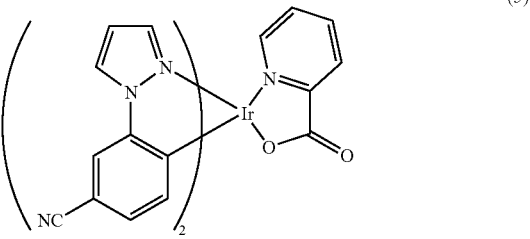

(7)

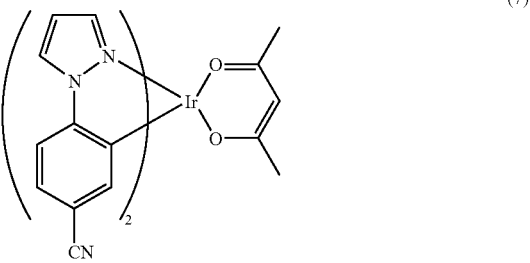

-continued
(8)
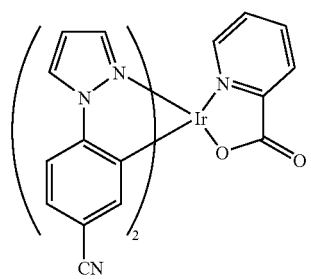
(9)
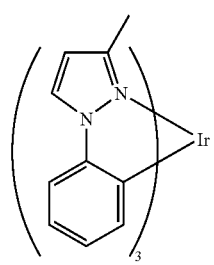
(10)
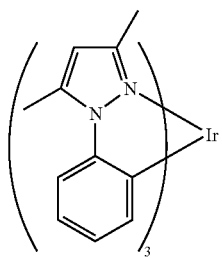
(11)
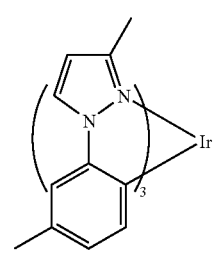
(12)
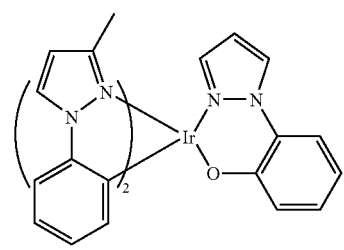
-continued
(13)
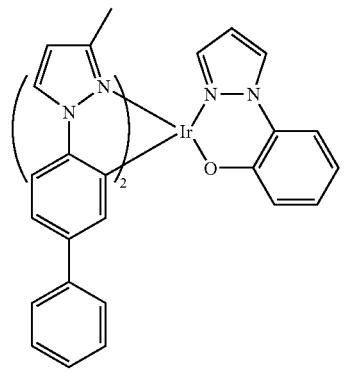
(14)
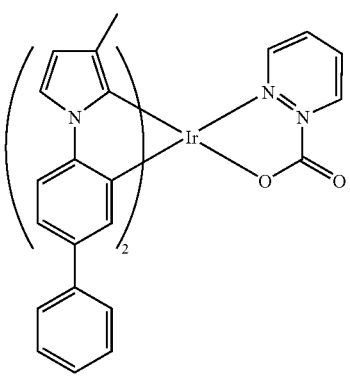
(15)
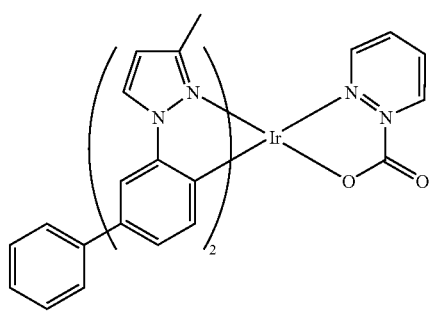
(16)
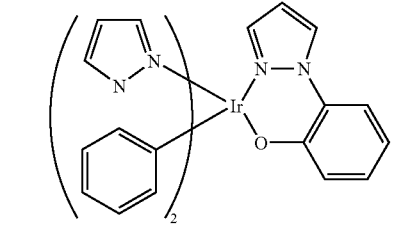
(17)
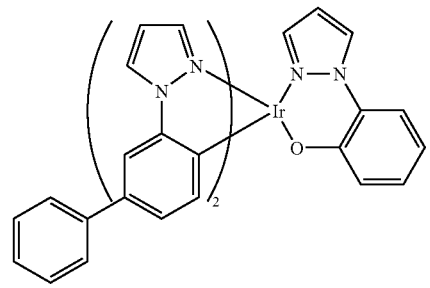

-continued

(18)
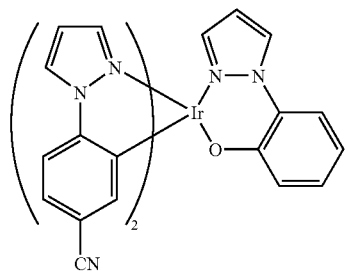

(19)
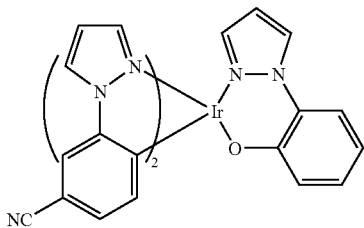

(20)
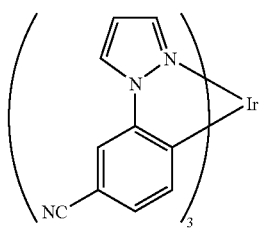

(21)
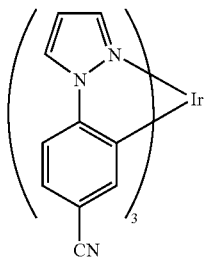

(22)
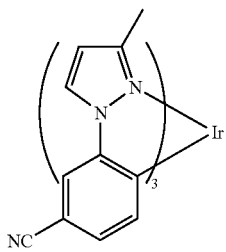

(23)
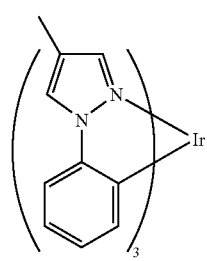

-continued

(24)
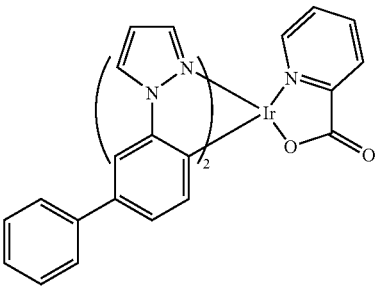

The iridium compound of formula (1) according to the present invention may be synthesized via various reaction paths that are common in the art. An exemplary method of synthesizing the iridium compound of formula (1) will be described below.

Initially, a phenylpyrazole compound is synthesized according to reaction scheme (1) below.

Reaction scheme (1)

In reaction scheme (1), $R_1$, $R_2$, $R_3$, $R_4$, $R_5$, $R_6$, and $R_7$ are the same as described above, and X is a halogen atom.

This phenylpyrazole compound is reacted with an iridium compound, for example, $Ir(acac)_3$, to obtain the iridium compound of formula (2b) that contains no ligand X.

The iridium compound of formula (2a) that contains the ligand X may be synthesized by reacting the phenylpyrazole compound, an iridium compound, for example, $IrCl_3$, and a compound (XH) that contains the ligand X.

The metallic compound having a novel bidentate ligand of formula (31) above according to the present invention is an organic metallic compound, which may contain Ir, etc. as a metallic component. Unlike a conventional ppy(2-phenylpyridine) ligand having a pyridine ring, the bidentate ligand of formula (31) contains a pyrazole ring, an imidazole ring or an oxazole ring.

An example of a compound of formula (31) with a bidentate ligand is the metallic compound of formula (32) below.

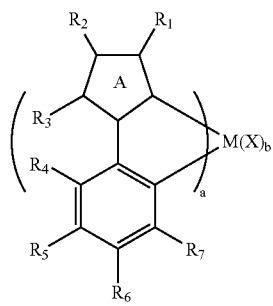
(32)

wherein M is one of Ir, Pt, and Os;

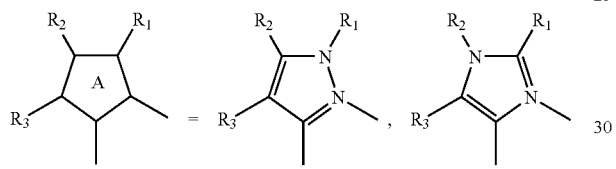

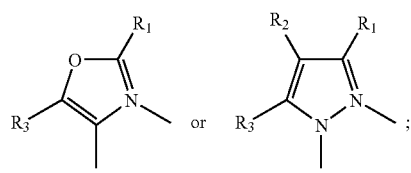
or $R_1$, $R_2$, $R_3$, $R_4$, $R_5$, $R_6$, and $R_7$ are the same as described above; X is a monoanionic, bidentate ligand; and a is an integer from 1 to 3; and b is an integer from 0 to 2 where a+b=3.

Examples of X in formula (32) above include acetylacetonate (acac), hexafluoroacetylacetonate (hfacac), salicylidene (sal), picolinate (pic), 8-hydroxyquinolinate (hquin), α-amino acid L-proline (L-pro), dibenzoylmethane (dbm), tetramethylheptanedionate (tmd), 1-(2-hydoxyphenyl) pyrazolate (oppz), 3-isoquinolinecarboxylate (3iq), 1-isoquinolinecarboxylate (1iq), 1,5-dimethyl-3-pyrazolecarboxylate (dm3PC), phenylpyrazole (ppz), and quinolinecarboxylate (quin) and phenylpyridine (ppy). These ligands have formulae that are given below. In the following formulae, Ir is an exemplary metallic component.

acac

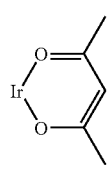

-continued hfacac

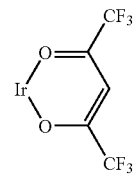

tmd

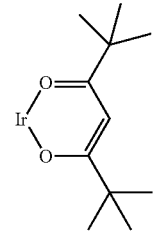

dbm

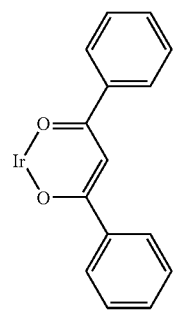

pic

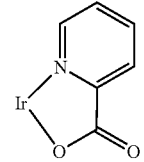

quin

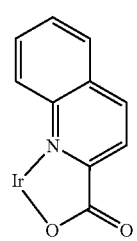

L-pro

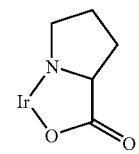

oppz

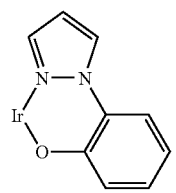

-continued

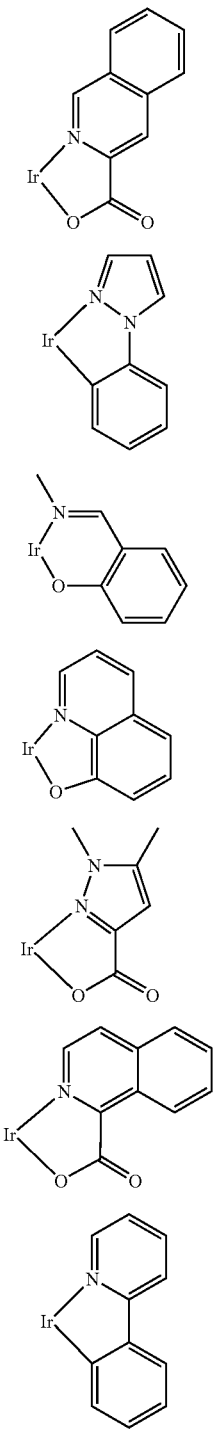

3iq ppz sal hquin dm3PC liq ppy

In the compound of formula (32) above, it is preferable that $R_1$, $R_2$, $R_3$, $R_4$, $R_5$, $R_6$, and $R_7$ are independently a C1-C12 alkyl group, a C5-C10 carbocyclic group, C6-C20 aryl group, a C1-C12 alkoxy group, a cyano group, a C2-C20 heterocycloalkyl group, a C2-C20 heteroaryl group, a fused C6-C20 aryl group, etc.

Examples of the metallic compound of formula (1) above having bidentate ligand include compounds of formulae (33) through (44) below.

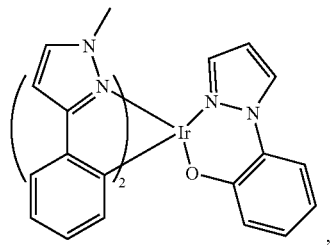
(33)

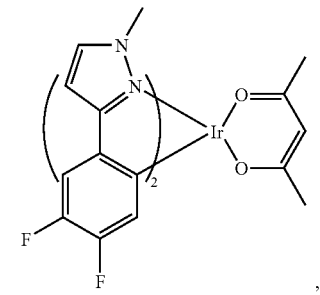
(34)

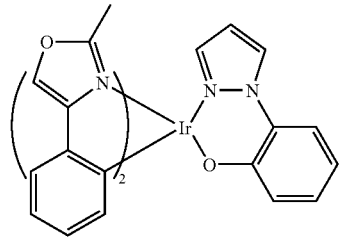
(35)

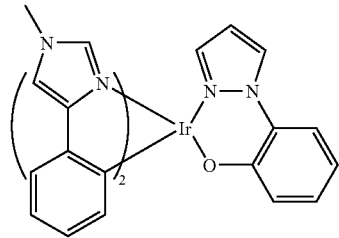
(36)

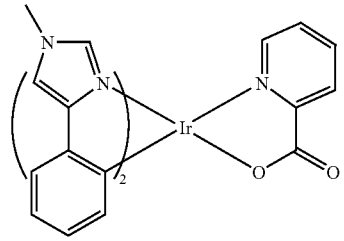
(37)

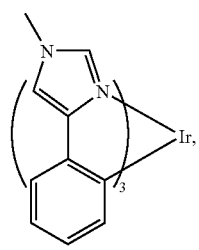
(38)

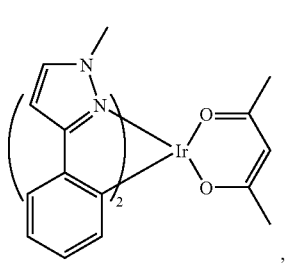 (39)
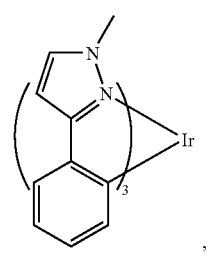 (40)
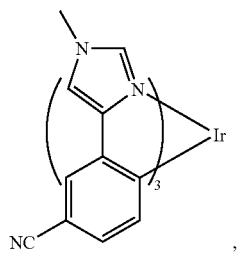 (41)
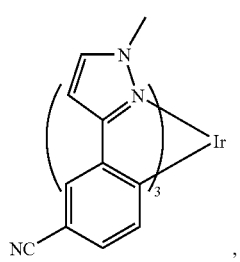 (42)
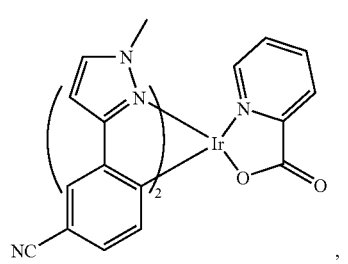 (43)
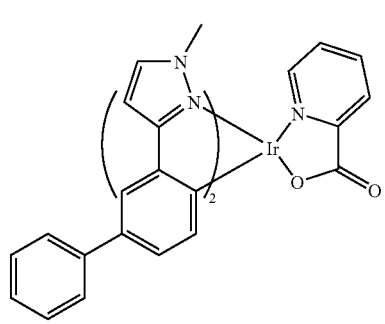 (44)
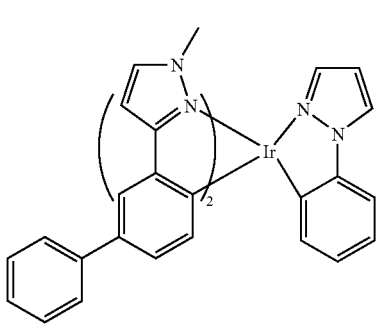 (45)
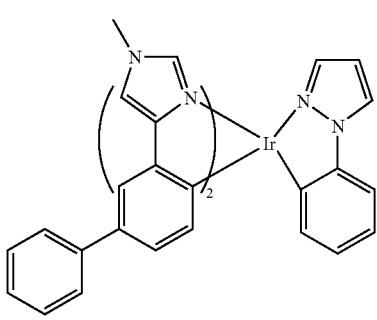 (46)
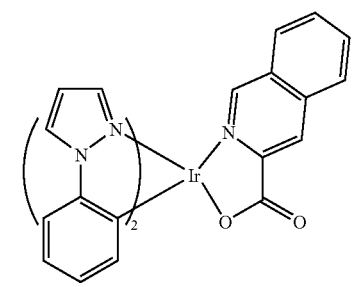 (47)
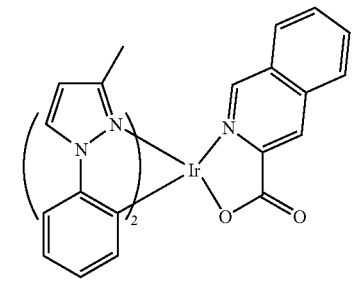 (48)
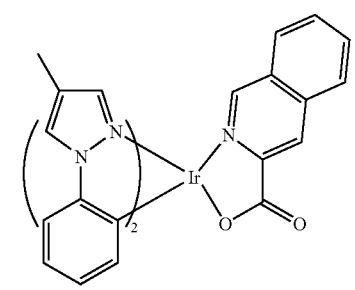 (49)

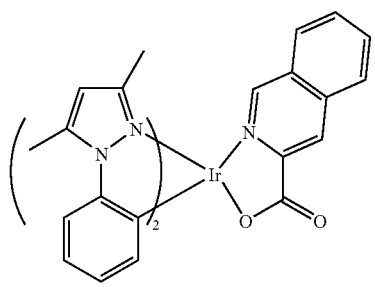
(50)
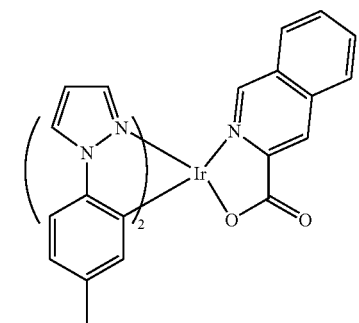
(51)
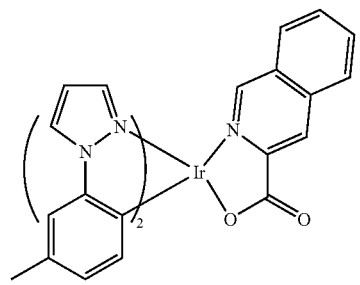
(52)
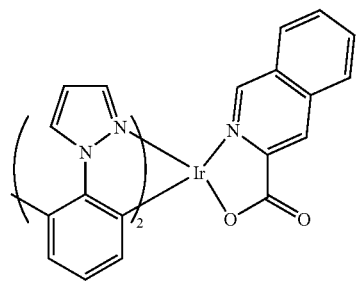
(53)
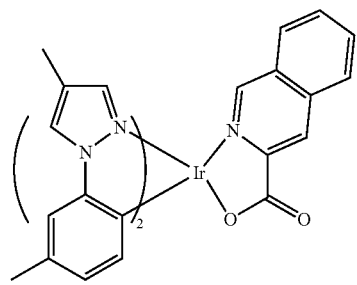
(54)
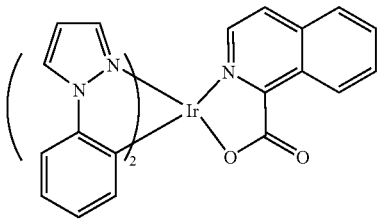
(55)
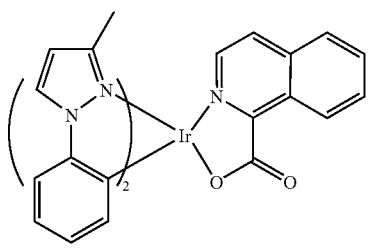
(56)
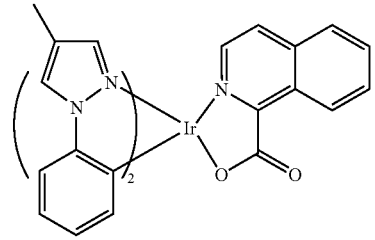
(57)
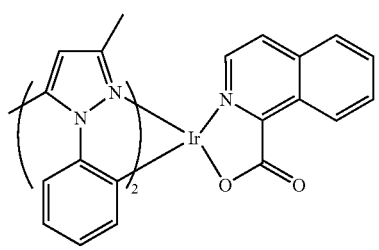
(58)
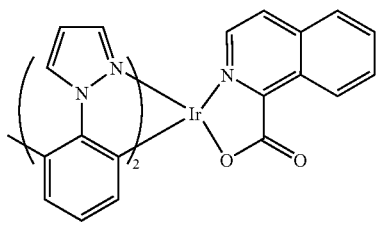
(59)
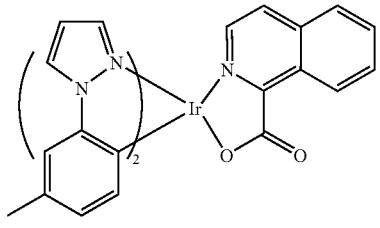
(60)

-continued

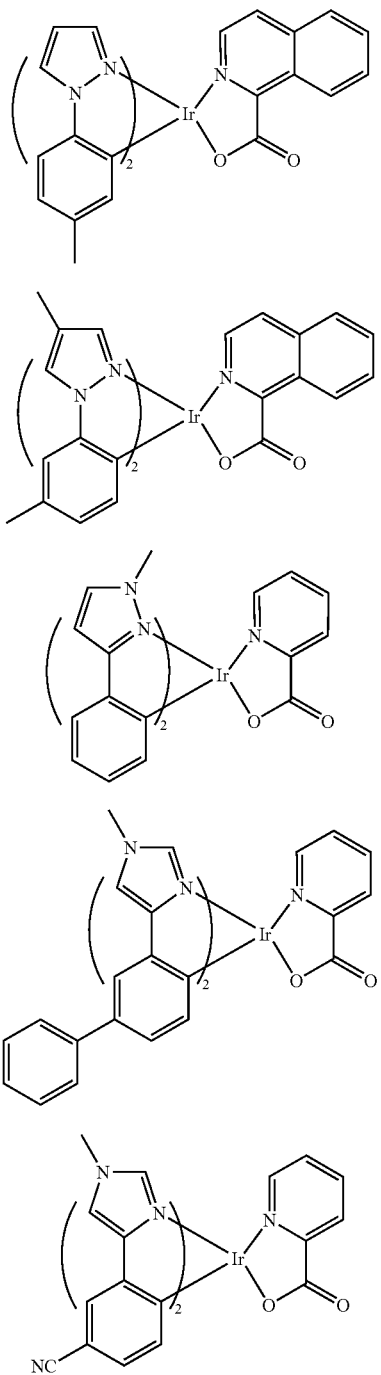

There are many reaction pathways for synthesizing the metallic compound having the bidentate ligand of formula (31) above. An exemplary method of synthesizing the metallic compound having the bidentate ligand of formula (31) will be described.

As illustrated in a reaction scheme below, initially, a compound containing the bidentate ligand of formula (31) is synthesized. This compound is reacted with an iridium compound to obtain an iridium dimmer. The iridium compound may be $IrCl_3$.

Next, the iridium dimmer is reacted with a compound (XH) containing ligand X.

Reaction Scheme (2)

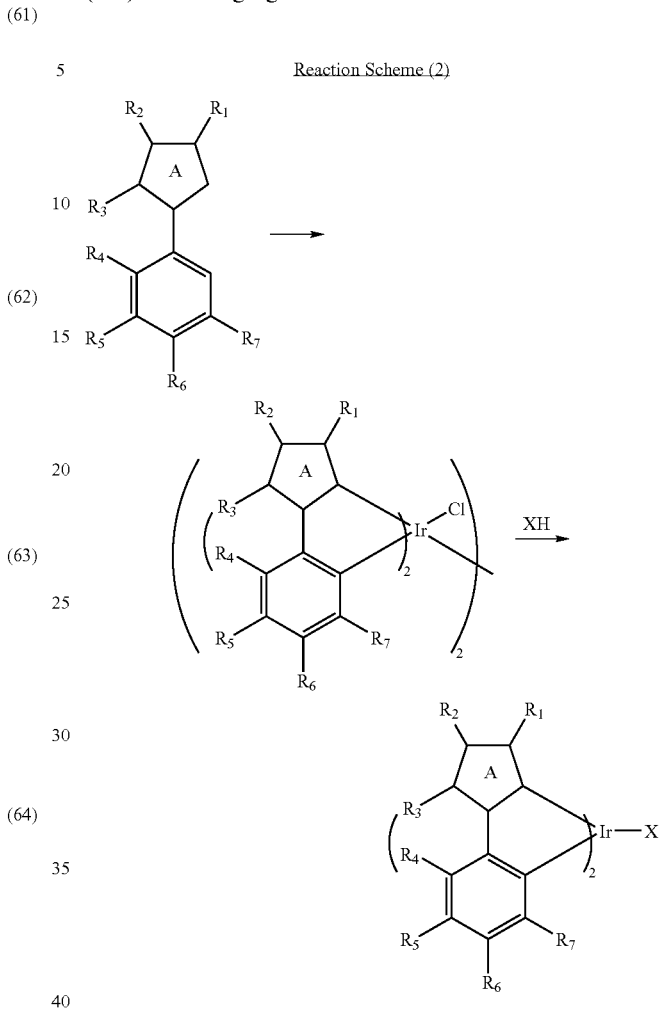

Examples of an unsubstituted C1-C30 alkyl group that may act as a substitute group for the iridium compound according to the embodiments of the present invention include methyl, ethyl, propyl, isobutyl, sec-butyl, pentyl, iso-amyl, hexyl, etc. At least one hydrogen atom of the alkyl group may be substituted with halogen atom, a C1-C30 alkyl group, a C1-C30 alkoxy group, a lower alkylamino group, a hydroxy group, a nitro group, a cyano group, an amino group, a amidino group, hydrazine, hydrazone, a carboxyl group, a sulfonic acid group, a phosphoric acid group, etc.

Examples of an unsubstituted C2-C30 alkenyl group that may act as a substitute group for the iridium compound according to the embodiments of the present invention include ethylene, propylene, isobutylene, vinyl, allyl, etc. At least one hydrogen atom of the alkenyl group may be substituted with halogen atom, a C1-C30 alkyl group, a C1-C30 alkoxy group, a lower alkylamino group, a hydroxy group, a nitro group, a cyano group, an amino group, a amidino group, hydrazine, hydrazone, a carboxyl group, a sulfonic acid group, a phosphoric acid group, etc.

Examples of an unsubstituted C1-C30 alkoxy group that may act as a substitute group for the iridium compound according to the embodiments of the present invention include methoxy, ethoxy, propoxy, isobutyloxy, sec-butyloxy, pentyloxy, iso-amyloxy, hexyloxy, etc. At least one hydrogen atom of the alkoxy group may be substituted with any substitute group that is described above as being suitable for the C1-C30 alkyl group.

The aryl group used as a substitute group for the iridium compound may be a C6-C30 carbocyclic aromatic system that contains at least one ring. The rings of the aryl group may be attached together in a pendent manner or may be fused. The term "aryl" embraces aromatic systems, such as phenyl, naphthyl, tetrahydronaphthyl, etc. At least one hydrogen atom of the aryl group may be substituted with any substitute group described above as being suitable for the C1-C20 alkyl group.

The arylalkyl group used as a substitute group for the iridium compound may be one of the above-defined aryl groups with lower alkyl groups, for example, methyl, ethyl, propyl, etc. substituted for some hydrogen atoms. Examples of such an arylalkyl group include benzyl, phenylethyl, 4-(tertbutyl)benzyl, 3,5-di-(tertbutyl)benzyl, 3,5-di(isopropyl)benzyl, etc. At least one hydrogen atom of the arylalkyl group may be substituted with any substitute group described above as being suitable for the C1-C30 alkyl group.

The heteroaryl group used as a substitute group for the iridium compound may be a C2-C30 monocarbocyclic system that contains one, two, or three hetero atoms selected from the group consisting of N, O, P, and S and has at least one ring. The rings of the heteroaryl group may be attached together in a pendent manner or may be fused. Examples of such a heteroaryl group include pyridyl, thienyl, furyl, etc.

The heteroarylalkyl group used as a substitute group for the iridium compound may be one of the above-defined heteroaryl groups with lower alkyl groups substituted for some hydrogen atoms. At least one hydrogen atom of the heteroarylalkyl group may be substituted with any substitute group described above as being suitable for the C1-C20 alkyl group.

The cycloalkyl group used as a substitute group for the iridium compound may be a C5-C30 monovalent monocyclic system. At least one hydrogen atom of the cycloalkyl group may be substituted with any substitute group described above as being suitable for the $C_1$-C30 alkyl group.

The heterocycloalkyl group used as a substitute group for the iridium compound may be a C1-C30 monovalent monocarbocyclic system that contains one, two, or three hetero atoms selected from the group consisting of N, O, P, and S and has lower alkyl groups substituted for some hydrogen atoms. At least one hydrogen atom of the heterocycloalkyl group may be substituted with any substitute group described above as being suitable for the C1-C20 alkyl group.

The compounds of formulae (1) and (31) according to the embodiments of the present invention can be used as deep blue luminescent materials for various display systems, and in particular, as host materials or dopants in the manufacturing of red (R), green (G), and blue (B) emissive layers of an organic electroluminescent (EL) device.

An organic EL device according to an embodiment of the present invention that includes the compound of formula (1) or (31), and a method of manufacturing the organic EL device will be described below with reference to FIG. 1.

As shown in FIG. 1, a first electrode 12 is initially formed as a pattern on a surface of a substrate 11. Any substrate that is commonly used for organic EL devices may be used as the first electrode 12. In most embodiments, glass substrates and transparent plastic substrates are used because they are easy to handle and waterproof and have an even surface. The substrate 11 may have a thickness of 0.3-0.7 mm.

The first electrode 12 is made of a conductive metal, which allows for easy hole injection, or a conductive metal oxide. Examples of materials for the first electrode 12 include indium tin oxide (ITO), indium zinc oxide (IZO), nickel (Ni), platinum (Pt), gold (Au), iridium (Ir), etc.

The substrate 11 with the first electrode 12 is washed, for example, using an organic solvent, such as isopropanol (IPA), acetone, etc. After washing, the substrate 11 is subjected to UV/ozone treatment.

Next, a hole injecting layer (HIL) 13 is optionally formed on the first electrode 12 on the substrate 11. The HIL 13 reduces contact resistance between the first electrode 12 and a hole transporting layer (HTL) 14 to be formed thereon and improves the ability of the HTL 14 to transport holes from the first electrode 12 to an emissive layer (EML) 15. It also improves the driving voltage and lifespan of the device. Suitable materials for the HIL 13 include water-soluble PEDOT {poly(3,4-ethylenedioxythiophene)}, PSS (polystyrene parasulfonate), starburst amines, such as IDE 406 (available from Idemitsu Kosan Co.), etc. The first electrode 12 is coated with such a material and dried to form the HIL 13.

When water-soluble PEDOT is used for the HIL 13, it is preferable to dry the coated layer may be dried at a temperature of 100-250° C., for example, at about 200° C. When a material that is compatible with vacuum deposition is used to form the HIL 13, no additional process, such as drying, is required after the formation of the HIL 13 prior to deposition of an overlaying layer.

Next, the HTL 14 is formed on the HIL 13. Exemplary materials for the HTL 14 include N,N'-bis(3-methylphenyl)-N,N'-diphenyl-[1,1-biphenyl]-4,4'-diamine (TPD), N,N'-di (naphthalene-1-yl)-N,N'-diphenyl benzidine{N,N'-di(naphthalene-1-yl)-N,N'-diphenyl-benzidine (NPB)} of formula (25) below, etc. The HTL 14 may be formed by any method, including spin coating and vacuum deposition. Vacuum deposition may be advantageous when using lower molecular weight materials.

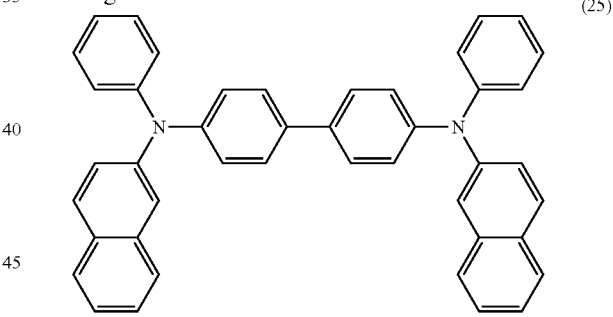

(25)

Next, the EML 15 is formed on the HTL 14. The EML 15 may be made of the compound of formula (1) alone or in combination with a common host material. In the latter case, the compound of formula (1) acts as a dopant. Suitable host materials include 4,4'-bis(carbazol-9-yl)-biphenyl (CBP) of formula (26) below, etc.

The EML 15 may be made of the compound of formula (31) alone or in combination with a common dopant material. In the latter case, the phosphorescent metallic compound of formula (31) acts as a host material.

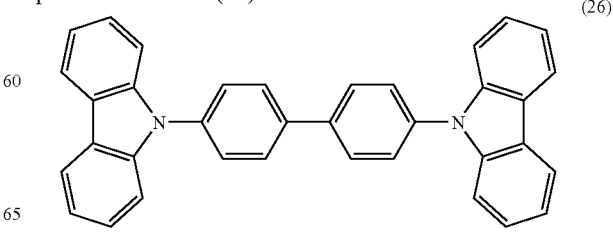

(26)

Any method, for example, simultaneous deposition, can be used when forming the EML layer 15. The amount of the compound of formula (1) that is used as a dopant is not limited. However, in some embodiments, the amount of the compound of formula (1) that is used as a dopant may be in a range of 5-40 parts by weight with respect to 100 parts by weight of the material of the EML layer 15. Greater or lesser amounts of dopant may affect the luminescent properties of the EL device.

Any method, for example, simultaneous deposition, can be applied when forming the EML layer 15. The amount of the compound of formula (31) that is used as a host material is not limited. However, in some embodiments the amount of the compound of formula (31) that is used as a host material may be in a range of 60-95 parts by weight with respect to 100 parts by weight of the material of the EML layer 15. Greater or lesser amounts of host material may affect the luminescent properties of the EL device deteriorate.

The EML layer 15 may have a thickness of 100-500 Å. If the thickness of the EML layer 15 is smaller than 100 Å, luminescent efficiency may drop. If the thickness of the EML layer 15 is greater than 500 Å, the driving voltage may increase.

A hole barrier layer (HBL) 16 is formed on the EML layer 15. The HBL 16 blocks exitons, which are generated from the emissive material in the EML layer 15, or holes from migrating into an electron transporting layer (ETL) 17. Suitable materials for the HBL 16 include phenanthrolines, such as BCP available from Universal Display Corporation (UDC); imidazoles; triazoles; oxadiazoles, such as PBD; aluminum complexes, such as BAlq having a formula below (available from UDC), etc. Any method may be applied when forming the HBL 16 without limitation. For example, vacuum deposition or spin coating may be used when forming the HBL 16, depending on the material used for the HBL 16.

The ETL 17 is formed on the HBL 16. Suitable materials for the ETL 17 include a compound of formula (27) below; oxazoles; isooxazoles; triazoles; isothiazoles; oxadiazoles; thiadiazoles; perylenes (see the formula below); aluminum complexes, such as Alq3 (tris(8-quinolinolato)-aluminum), BAlq, SAlq, and Almq3 (refer to the following formulae); gallium complexes, such as Gaq'$_2$OPiv, Gaq'$_2$OAc, and 2(Gaq'$_2$) (refer to the following formulae), etc. Vacuum deposition or spin coating may be used to form the ETL 17, depending on the material for the ETL 17.

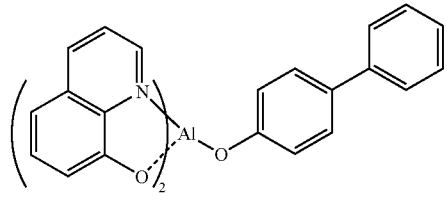

(27)

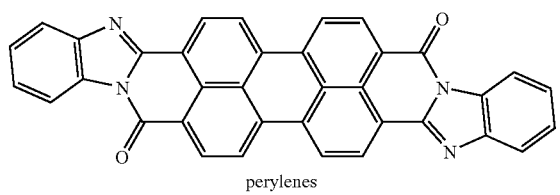

perylenes

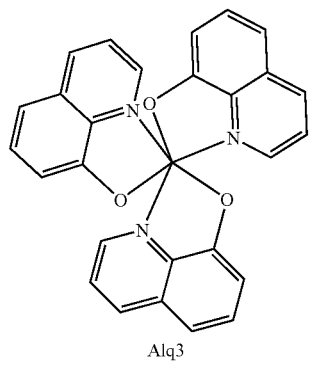

Alq3

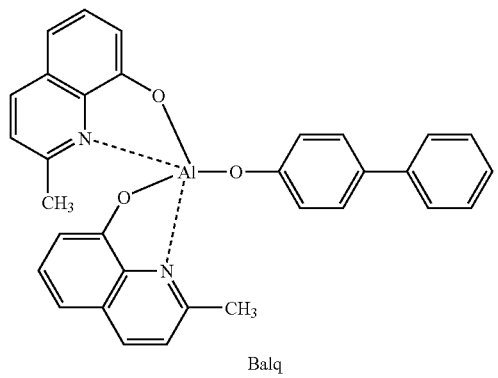

Balq

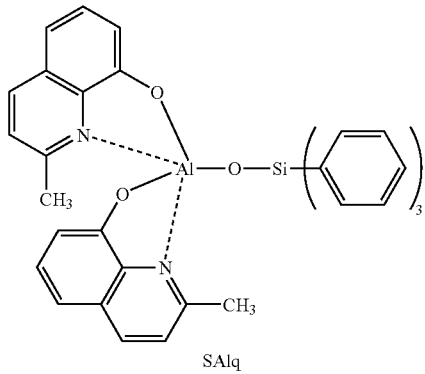

SAlq

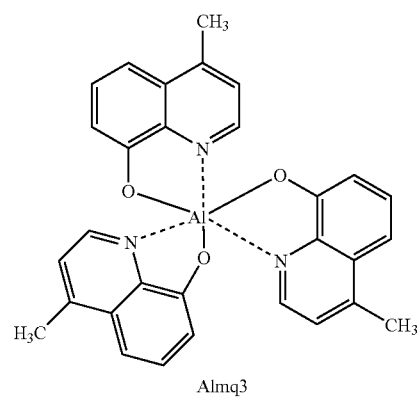

Almq3

-continued

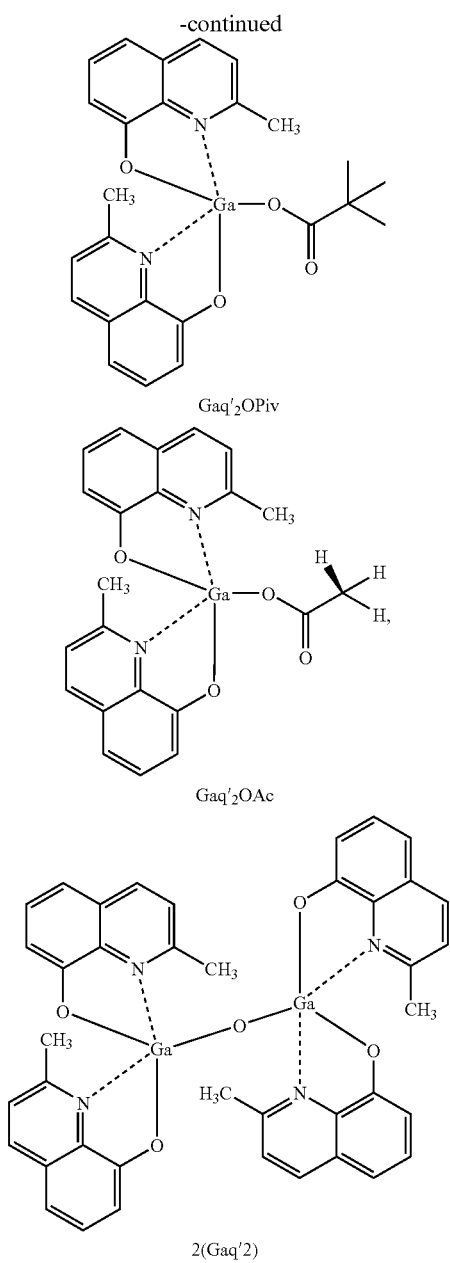

Gaq'₂OPiv

Gaq'₂OAc

2(Gaq'2)

Next, an electron injecting layer (EIL) 18 is formed on the ETL 17. Suitable materials for the EIL 18 include Alq3, LiF, NaCl, CsF, etc. Vacuum deposition or spin coating may be used to form the EIL 18. The EIL 18 may have a thickness of 1-15 Å.

Next, a second electrode 19 is formed on the EIL 18, and the device is sealed to complete its manufacture. The second electrode 19 is made of a low work function metal, for example, Li, Ca, LiF/Ca, LiF/Al, Al, Mg, or a Mg alloy, by deposition. The second electrode 19 may have a thickness of 800-3000 Å.

An organic EL device according to the present invention may have a stacked structure as illustrated in FIG. 1 or may may have an additional single or dual intermediate layer if required. The HIL, the HBL, and the EIL are optional.

The present invention will be described in greater detail with reference to the following examples. The following examples are illustrative purposes and are not intended to limit the scope of the invention.

Reagents Used

Potassium phosphate tribasic monohydrate, 1,4-dioxane, copper iodide, and (+,−) trans-1,2-diaminocyclohexane were purchased from Acros Co. Iridium chloride hydrate, iridium chloride acetylacetonate, glycerol, 2-methoxyethanol, 2-ethoxyethanol, 1-pyrazole, 3-methyl-1-phenylpyrazole, 3-methyl-1-m-tolylpyrazole, 3,5-dimethyl-1-phenylpyrazole, 3-iodobenzonitrile, 4-iodebenzonitrile, acetylacetone, and picolinic acid were purchased from Aldrich Co. Methylene chloride, methanol, hexane, magnesium sulfate, and magnesium carbonate were purchased from Ducksan Chemicals Co.

Pyrazole, 2-iodoanisol, acetophenone, N,N-dimethylformamide, dimethylformamide dimethylacetal, dimethyl sulfate, 1H-4-phenylimidazole, 2-bromoacetophenone, and acetoamide were purchased from Tokyo Kasei Co. Ltd. (TCI).

Nitrobenzene, potassium carbonate ($K_2CO_3$), HBr, hydrazine monohydrate, ethanol, acetone, ethylcellosolve, sodium carbonate, 1,2-dichloroethane, 2-pyridine carboxylic acid, acetylacetone, THF, NaHa were purchased from Wako Pure Chemical Co. Ltd. (WAKO). Iridium chloride hydrochloride hydrate, iridium chloride, 3,4-difluoroacetophenone, 3-cyanoacetophenone, 1-phenylpyrazole, 1-isoquinoline carboxylic acid, and 3-isoquinolinecarboxylic acid were purchased from Aldrich Co.

Analysis Methods

The structure of compounds synthesized in the following examples was identified using $^1$H-NMR, $^{13}$C-NMR, a UV spectrometer, and a spectrofluorometer. $^1$H-NMR and $^{13}$C-NMR were measured using a Bruker AM-300 spectrometer. The UV spectrometer used was a BECKMAN DU-650. The spectrofluorometer used was a JASCO FP-750. Chemical shift in solvent was measured in ppm.

SYNTHESIS EXAMPLE 1

Synthesis of 3-pyrazol benzonitrile of Formula (3)

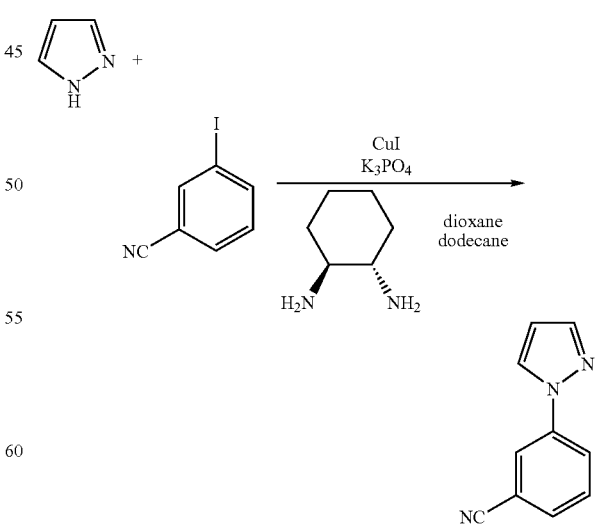

0.01 mmol of copper iodide, 2.1 mmol of potassium phosphate tribasic monohydrate, 1.2 mmol of 1-pyrazole, and 10 mL of 1,4-dioxane were placed in a sealed tube, followed by injection of nitrogen and stirring for 30 minutes. 3-iodobenzonitrile and 0.01 mmol of (+,−)-trans-1,2-diminocyclohexane were added into the reaction mixture, the tube was plugged and heated at 110° C. for 24 hours while stirring.

The progress of the reaction was checked using thin layer chromatography (TLC) to determine if the reaction had completed. After the completion of the reaction, the solvent was removed by high-vacuum distillation. The reaction product was extracted using methylene chloride and washed with a saturated NaCl solution. The extracted methylene chloride phase was dried using MgSO$_4$ and purified into solid form using flash column chromatography (eluent of methylene chloride and methanol). This resulting solid material was dried in a vacuum for 3 hours to provide a compound of formula (3) with a yield of 50%.

$^1$H-NMR (CDCl$_3$, 300 MHz): δ(ppm) 8.04 (d, J=1.11, 1H) 7.99~7.95 (m, 2H) 7.78 (d, J=1.53, 1H) 7.62~7.53 (m, 2H) 6.54 (t, J=2.11, 1H)

SYNTHESIS EXAMPLE 2

Synthesis of Compound (A)

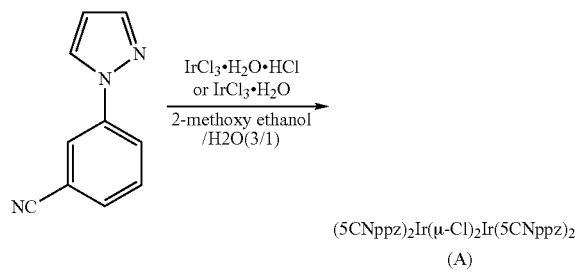

(5CNppz)$_2$Ir(μ-Cl)$_2$Ir(5CNppz)$_2$
(A)

100 mL of 2-methoxy ethanol was stirred in a nitrogen atmosphere at room temperature for 30 minutes, and 4 mmol of iridium chloride hydrochloride hydrate and 10 mmol of the compound (3) were added and heated in a nitrogen atmosphere for 12 hours.

After reaction was completed, the reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered and dried in a vacuum for about 3 hours to provide compound A with a yield of 50%.

SYNTHESIS EXAMPLE 3

Synthesis of Ir(5-CNphenyl-pyrazol)$_2$(acac) of Formula (4)

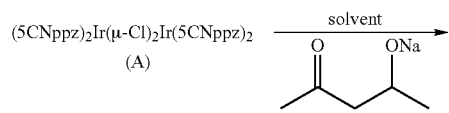

-continued

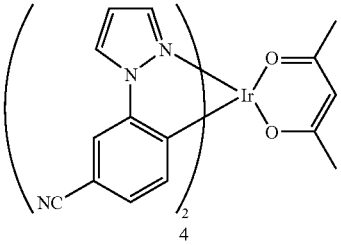

100 mL of 2-ethoxy ethanol was stirred in a nitrogen atmosphere at room temperature for 30 minutes, and 5 mmol of compound (A), 15 mmol of acac salt, and 2.5 mL of 3N Na$_2$CO$_3$ were added and heated in a nitrogen atmosphere while stirring for 12 hours and checking the progress of the reaction using TLC to determine if the reaction had completed. The reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered, purified using column chromatography, and dried in a vacuum for 3 hours to provide the compound of formula (4) with a yield of 50%.

$^1$H-NMR (CDCl$_3$, 300 MHz): δ(ppm) 8.82 (d, J=2.874 Hz, 2H), 7.86 (d, J=1.5 Hz, 2H), 7.81 (d, J=2.157 Hz, 2H), 6.97~6.52 (m, 4H), 6.41 (d, J=7.773 Hz, 2H), 5.34 (s, 1H), 1.77 (s, 6H)

SYNTHESIS EXAMPLE 4

Synthesis of Ir(5-CNphenyl-pyrazol)$_2$(pic) of Formula (5)

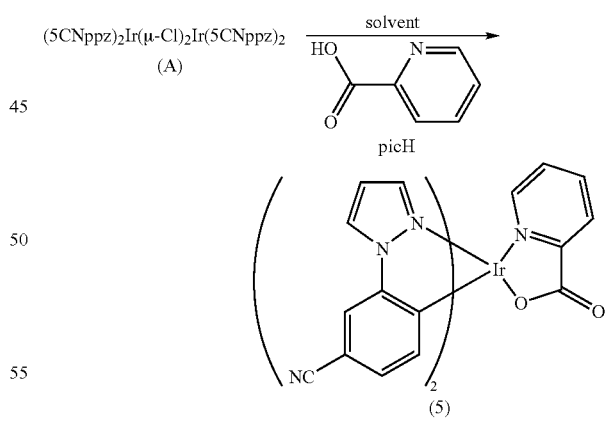

100 mL of 2-ethoxy ethanol was stirred in a nitrogen atmosphere at room temperature for 30 minutes, 5 mmol of compound (A), 15 mmol of picolinic acid, and 2.5 mL of 3N Na$_2$CO$_3$ were added and heated in a nitrogen atmosphere while stirring for 12 hours and checking the progress of the reaction using TLC to determine if the reaction had completed.

The reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered, purified using column chromatography, and dried in a vacuum for 3 hours to provide the compound of formula (5) with a yield of 50%.

$^1$H-NMR (CDCl$_3$, 300 MHz): δ(ppm) 8.38 (d, J=7.626 Hz, 1H), 8.19 (d, J=2.859 Hz, 1H), 8.165 (d, J=2.87 Hz, 1H), 8.017 (td, J=1.45 Hz, 7.713 Hz, 1H), 7.467 (m, 3H), 7.029 (dd, J=1.53 Hz, 7.78 Hz, 1H), 6.96 (dd, J=1.428 Hz, 7.73 Hz, 1H), 6.8392 (d, J=2.172 Hz, 1H), 6.7514 (t, J=5.154 Hz, 1H), 6.5772 (t, J=5.05 Hz, 1H), 6.5022 (d, J=7.82 Hz, 1H), 6.1772 (d, J=7.797 Hz, 1H)

SYNTHESIS EXAMPLE 5

Synthesis of 4-pyrazol benzonitrile of Formula (6)

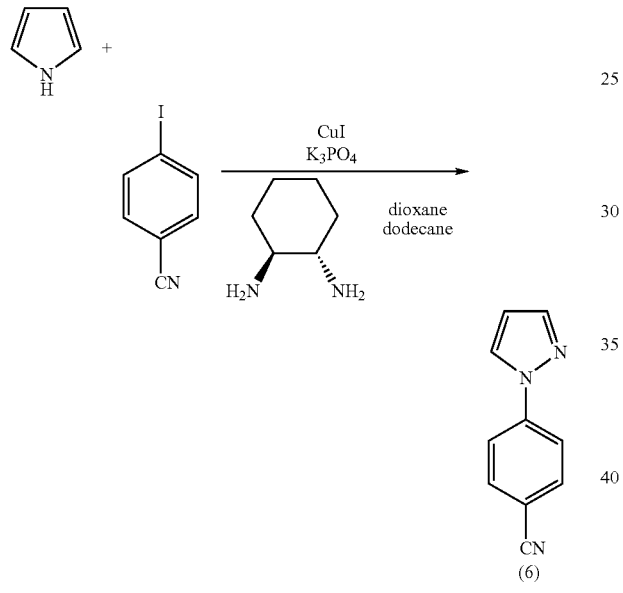

0.01 mmol of copper iodide, 2.1 mmol of potassium phosphate tribasic monohydrate, 1.2 mmol of 1-pyrazole, and 10 mL of 1,4-dioxane were placed in a sealed tube, followed by stirring for 30 minutes in a nitrogen atmosphere. 4-iodobenzonitrile and 0.01 mmol of (+,−)-trans-1,2-diminocyclohexane were added into the reaction mixture, the tube was plugged and heated at 110° C. for 24 hours while stirring.

The progress of the reaction was checked using TLC to determine if the reaction had completed. After the completion of the reaction, the solvent was removed by high-vacuum distillation. The reaction product was extracted using methylene chloride and washed with a saturated NaCl solution. The extracted methylene chloride phase was dried using MgSO$_4$ and purified into solid form using flash column chromatography (eluent of methylene chloride and methanol). This resulting solid material was dried in a vacuum for 3 hours to provide the compound of formula (6) with a yield of 75%.

$^1$H-NMR (CDCl$_3$, 300 MHz): δ(ppm) 8.00 (d, J=2.86, 1H) 7.84~7.81 (m, 2H) 7.77~7.71 (m, 3H) 6.53 (t, J=2.06, 1H)

SYNTHESIS EXAMPLE 6

Synthesis of Compound (B)

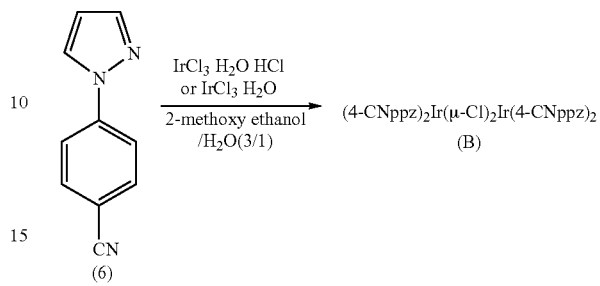

100 mL of 2-methoxy ethanol was stirred in a nitrogen atmosphere at room temperature for 30 minutes, and 4 mmol of iridium chloride hydrochloride hydrate and 10 mmol of the compound (6) were added and heated in a nitrogen atmosphere while stirring.

The progress of the reaction was checked using TLC to determine if the reaction had completed. After the completion of the reaction, the reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered and dried in a vacuum for about 3 hours to provide compound B with a yield of 75%.

SYNTHESIS EXAMPLE 7

Synthesis of Ir(4-CNphenyl-pyrazol)$_2$(acac) of Formula (7)

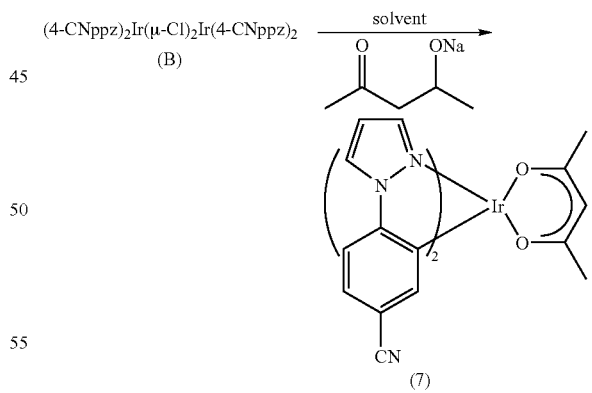

100 mL of 2-ethoxy ethanol was stirred in a nitrogen atmosphere at room temperature for 30 minutes, 5 mmol of the compound (B), 15 mmol of acac salt, and 2.5 mL of 3N Na$_2$CO$_3$ were added and heated in a nitrogen atmosphere for 12 hours while stirring.

The progress of the reaction was checked using TLC to determine if the reaction had completed. After the completion of the reaction, the reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered, purified using column chromatography, and dried in a vacuum for 3 hours to provide the compound of formula (7) with a yield of 50%.

$^1$H-NMR (CDCl$_3$, 300 MHz): δ(ppm) 8.15 (d, J=2.78 Hz, 2H), 7.66 (d, J=1.74 Hz, 2H), 7.22 (d, J=4.59 Hz, 4H), 6.78 (t, J=4.734 Hz, 2H), 6.4778 (s, 2H), 5.2902 (s, 1H), 1.8508 (s, 6H), 1.5848 (s, 5H)

SYNTHESIS EXAMPLE 8

Synthesis of Ir(4-CNphenyl-pyrazole)$_2$(pic) of Formula (8)

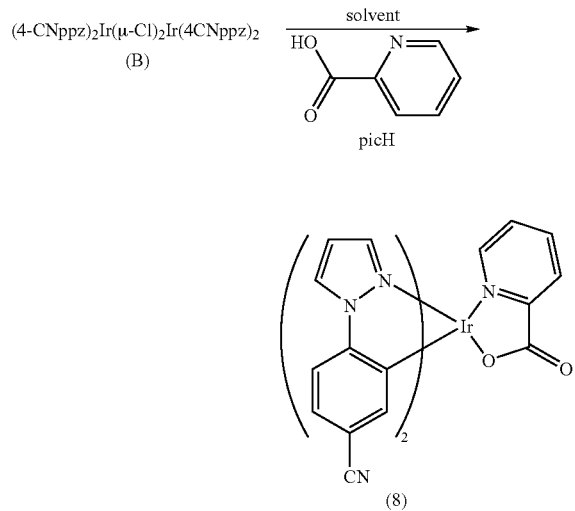

100 mL of 2-ethoxy ethanol were stirred in a nitrogen atmosphere at room temperature for 30 minutes, 5 mmol of compound (B), 15 mmol of picolinic acid, and 2.5 mL of 3N Na$_2$CO$_3$ were added and heated in a nitrogen atmosphere while stirring for 12 hours and checking the progress of the reaction using TLC to determine if the reaction had completed.

The reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered, purified using column chromatography, and dried in a vacuum for 3 hours to provide the compound of formula (8) with a yield of 50%.

$^1$H-NMR (CDCl$_3$, 300 MHz): δ(ppm) 8.37 (d, J=7.79 Hz, 1H), 8.176 (t, J=5.28 Hz, 2H), 8.0084 (td, 1H), 8.3834 (d, J=2.364 Hz, 2H), 7.4492 (td, 14.29 Hz, 1H), 7.3456 (s, 2H), 7.2812 (m, 3H), 6.8580 (d, J=2.18 Hz, 1H), 6.77422 (t, J=5.187 Hz, 1H), 6.64209 (m, 2H), 6.45282 (s, 1H)

SYNTHESIS EXAMPLE 9

Synthesis of Fac Ir(5-methyl-phenylpyrazol)$_3$ of Formula (9)

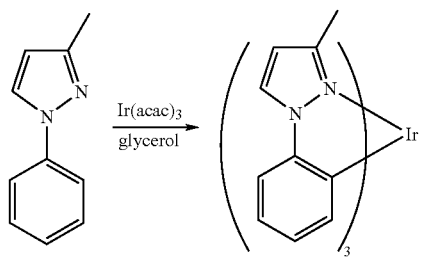

100 mL of glycerol was stirred in a nitrogen atmosphere at room temperature for 30 minutes, Ir(acac)$_3$ and 6 equivalents of 3-methyl-1-phenylpyrazol were added and heated at 180-200° C. for 24 hours while stirring.

Figure 12:
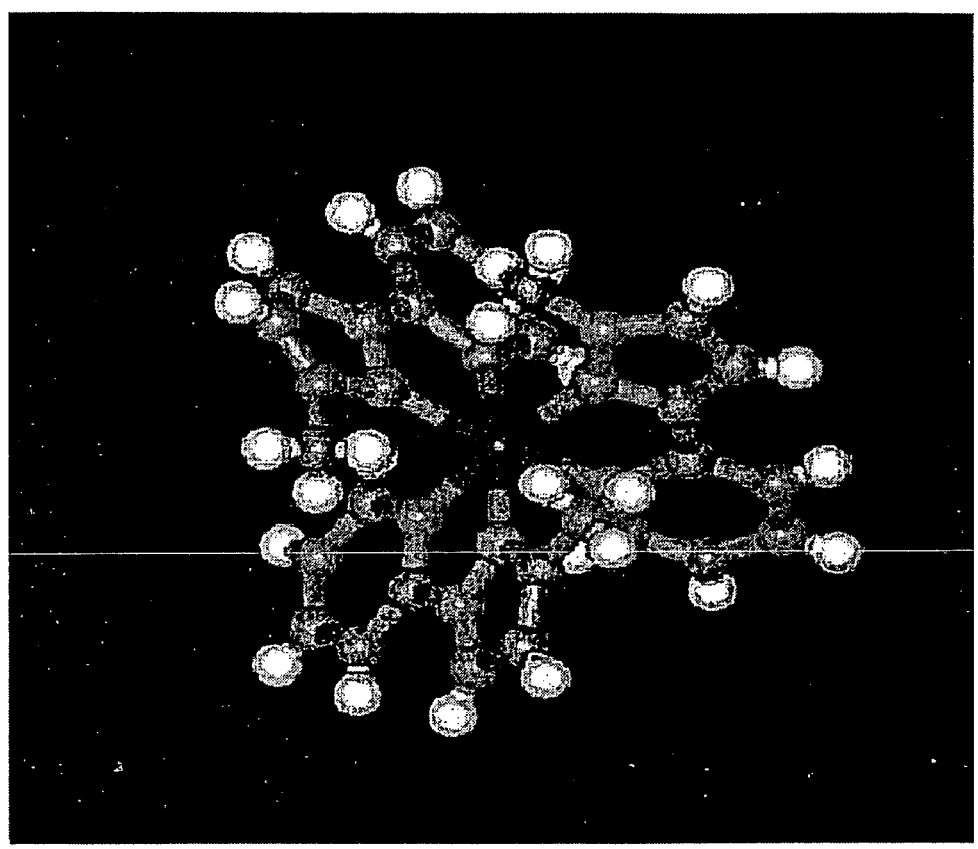
FIG. 12 illustrates the crystalline structure of the iridium compound of formula (9) according to the embodiments of the present invention.

After the completion of the reaction, water was added to the reaction product and filtered through a glass filter to obtain a crude product. This crude product was washed with hexane, dissolved in methylene chloride, purified using flash column chromatography, and dried in a vacuum for 3 hours to provide the compound of formula (9) with a yield of 20%. A dispersion of hexane in a solution of 1 part by weight of methanol dissolved in methylene chloride was used to identify the crystalline structure of the compound 9 illustrated in FIG. 12.

$^1$H-NMR (CDCl$_3$, 300 MHz): 7.93 (d, J=2.31, 3H) 7.18 (d, J=13.44, 3H) 6.92 (t, J=3.58, 3H) 6.74~6.62 (m, 6H) 6.14 (d, J=2.55, 3H) 1.708 (s, 9H)

SYNTHESIS EXAMPLE 10

Synthesis of Fac Ir(3,5-dimethyl-phenylpyrazol)$_3$ of Formula (10)

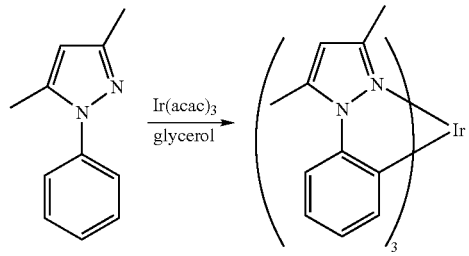

100 mL of glycerol was stirred in a nitrogen atmosphere at room temperature for 30 minutes, Ir(acac)$_3$ and 6 equivalents of 3,5-dimethyl-1-phenylpyrazol were added and heated at 180-200° C. for 24 hours while stirring.

After the completion of the reaction, water was added to the reaction product and filtered through a glass filter to obtain a crude product. This crude product was washed with hexane, dissolved in methylene chloride, purified using flash column chromatography, and dried in a vacuum for 3 hours to provide the compound of formula (10) with a yield of 20%.

$^1$H-NMR (CDCl$_3$, 300 MHz): 7.39 (d, J=8.04, 3H) 6.90~6.84 (m, 3H) 6.70~6.61 (m, 6H) 5.86 (s, 3H) 2.75 (s, 9H) 1.62 (s, 9H)

SYNTHESIS EXAMPLE 11

Synthesis of Fac Ir(5-methylphenyl-4-methylpyrazol)₃ of Formula (11)

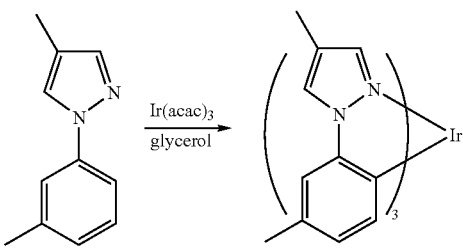

100 mL of glycerol was stirred in a nitrogen atmosphere at room temperature for 30 minutes, Ir(acac)₃ and 6 equivalents of 3-methyl-1-m-tolyl-pyrazol were added and heated at 180-200° C. for 24 hours while stirring.

After the completion of the reaction, water was added to the reaction product and filtered through a glass filter to obtain a crude product. This crude product was washed with hexane, dissolved in methylene chloride, purified using flash column chromatography, and dried in a vacuum for 3 hours to provide the compound of formula (11) with a yield of 20%.

¹H-NMR (CDCl₃, 300 MHz): 8.36 (s, 3H) 7.20 (s, 3H) 6.81 (s, 3H) 6.48~6.41 (m, 6H) 2.17 (s, 9H) 2.02 (s, 9H)

SYNTHESIS EXAMPLE 12

Synthesis of Ir(5-methyl-phenylpyrazol)₂(oppz) of Formula (12)

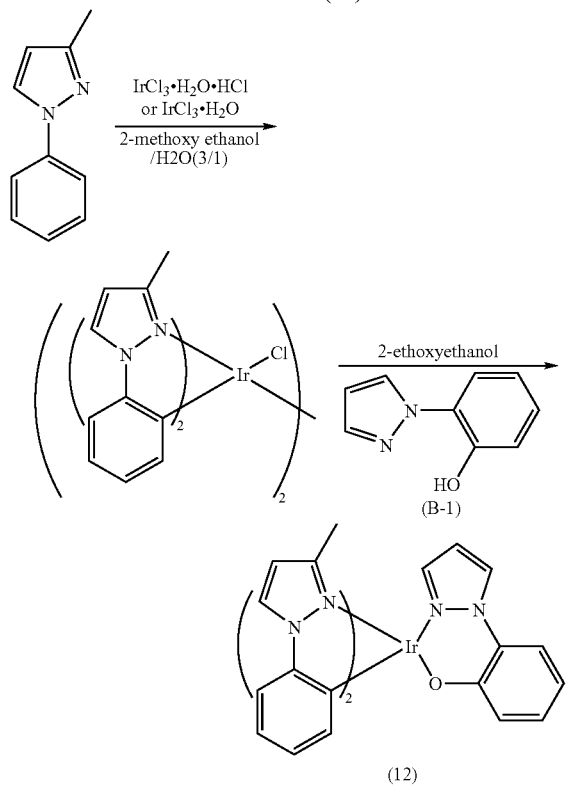

100 mL of 2-methoxy ethanol was stirred in a nitrogen atmosphere at room temperature for 30 minutes, and 4 mmol of iridium chloride hydrochloride hydrate and 10 mmol of 3-methyl-1-phenylpyrazol were added and heated in a nitrogen atmosphere for 12 hours while stirring.

The progress of the reaction was checked using TLC to determine if the reaction had completed. After the completion of the reaction, the reaction product was distilled in a high vacuum to remove the solvent, followed by extraction using methylene chloride. The extracted methylene chloride phase was washed with a saturated NaCl solution and dried using MgSO₄, followed by distillation under reduced pressure to minimize the remaining solvent. Hexane was added to precipitate a solid material. This solid material was filtered and dried in a vacuum for about 3 hours to provide a dimer with a yield of 50%.

100 mL of 2-ethoxy ethanol were stirred in a nitrogen atmosphere at room temperature for 30 minutes, 5 mmol of the dimer, 15 mmol of compound (B-1), and 2.5 mL of 3N Na₂CO₃ were added and heated in a nitrogen atmosphere while stirring for 12 hours and checking the progress of the reaction using TLC to determine if the reaction had completed.

After the completion of the reaction, the reaction product was distilled in a high vacuum to remove the solvent, followed by extraction using methylene chloride. The extracted methylene chloride phase was washed with a saturated NaCl solution and dried using MgSO₄, followed by distillation under reduced pressure to minimize the remaining solvent. Hexane was added to precipitate a solid material. This solid material was filtered, purified using column chromatography, and dried in a vacuum for 3 hours to provide the compound of formula (12) with a yield of 50%.

¹H-NMR (CDCl₃, 300 MHz): 8.02 (d, J=2.76, 2H) 7.98 (d, J=2.12, 2H) 7.857 (d, J=2.76, 1H) 7.205 (d, J=7.638, 1H) 7.134~7.082 (m, 2H) 6.955~6.86 (m, 3H) 6.749~6.636 (m, 4H) 6.539~6.48 (m, 2H) 6.34~6.28 (m, 3H) 6.099 (d, J=2.73, 1H)

SYNTHESIS EXAMPLE 13

Synthesis of Ir(2-(4-phenyl-phenyl)-5-methylpyrazol)₂ (oppz) of Formula (13)

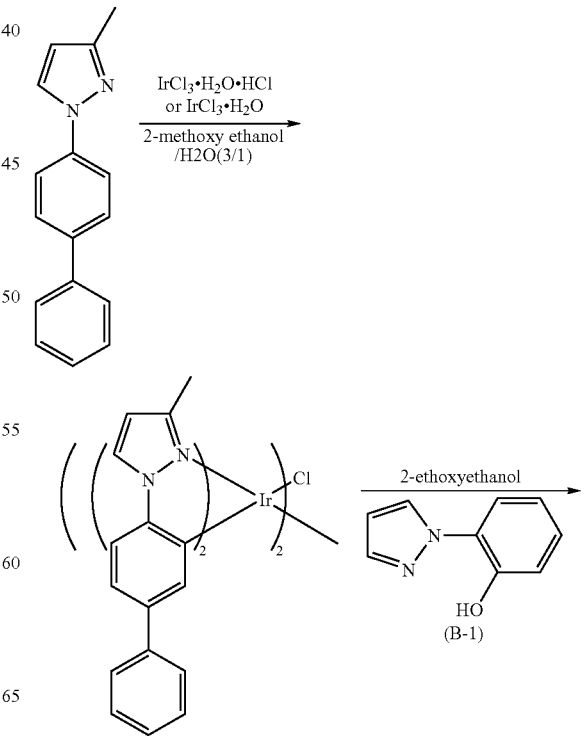

-continued

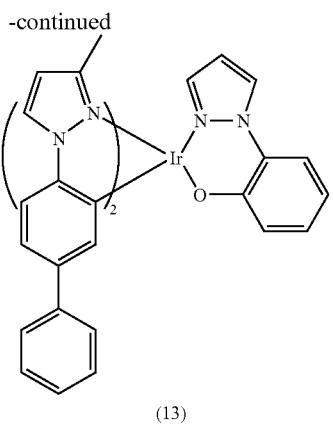

(13)

100 mL of 2-methoxy ethanol was stirred in a nitrogen atmosphere at room temperature for 30 minutes, and 4 mmol of iridium chloride hydrochloride hydrate and 10 mmol of 1-biphenyl-4-yl-3-methyl-1H-pyrazol were added and heated in a nitrogen atmosphere for 12 hours while stirring.

The progress of the reaction was checked using TLC to determine if the reaction had completed. After the completion of the reaction, the reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered and dried in a vacuum for about 3 hours to provide a dimer with a yield of 50%.

100 mL of 2-ethoxy ethanol were stirred in a nitrogen atmosphere at room temperature for 30 minutes, 5 mmol of the dimer, 15 mmol of the compound (B-1), and 2.5 mL of 3N Na$_2$CO$_3$ were added and heated in a nitrogen atmosphere while stirring for 12 hours and checking the progress of the reaction using TLC to determine if the reaction had completed.

After the completion of the reaction, the reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered, purified using column chromatography, and dried in a vacuum for 3 hours to provide the compound of formula (13) with a yield of 50%.

$^1$H-NMR (CDCl$_3$, 300 MHz): 8.57 (d, J=2.79, 1H) 8.37 (d, J=2.65, 2H) 7.55 (d, J=8.17, 1H) 7.44~7.09 (m, 14H) 6.87~6.80 (m, 2H) 6.72 (d, J=1.94, 1H) 6.56~6.40 (m, 5H) 6.32 (d, J=2.75, 1H)

SYNTHESIS EXAMPLE 14

Synthesis of Ir(2-(4-phenyl-phenyl)-5-methylpyrazol)$_2$ (pic) of Formula (14)

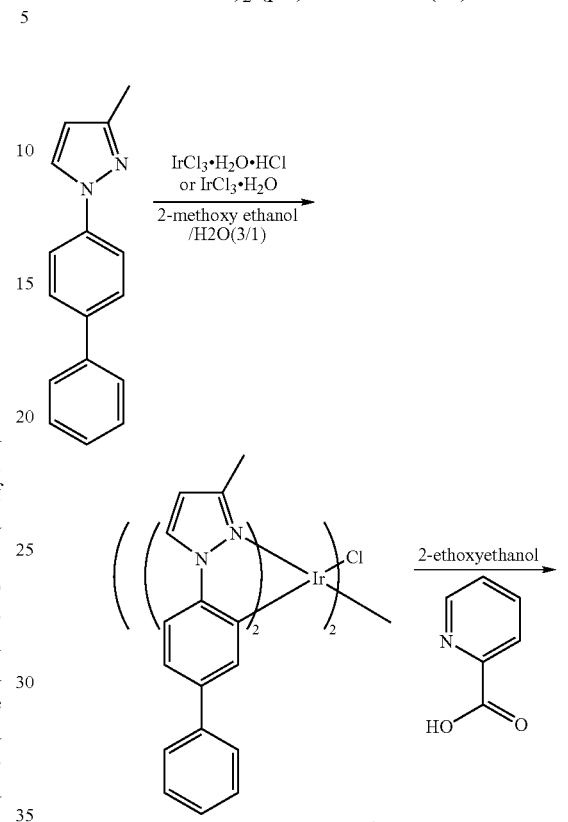

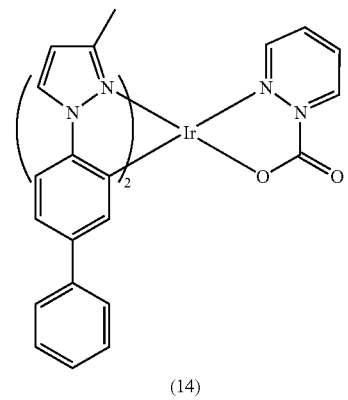

(14)

100 mL of 2-methoxy ethanol was stirred in a nitrogen atmosphere at room temperature for 30 minutes, and 4 mmol of iridium chloride hydrochloride hydrate and 10 mmol of 1-biphenyl-4-yl-3-methyl-1H-pyrazol were added and heated in a nitrogen atmosphere for 12 hours while stirring.

The progress of the reaction was checked using TLC to determine if the reaction had completed. After the completion of the reaction, the reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered and dried in a vacuum for about 3 hours to provide a dimer with a yield of 50%.

100 mL of 2-ethoxy ethanol were stirred in a nitrogen atmosphere at room temperature for 30 minutes, 5 mmol of the dimer, 15 mmol of picolinic acid, and 2.5 mL of 3N $Na_2CO_3$ were added and heated in a nitrogen atmosphere while stirring for 12 hours and checking the progress of the reaction using TLC to determine if the reaction had completed.

After the completion of the reaction, the reaction product was distilled in a high vacuum to remove the solvent, followed by extraction using methylene chloride. The extracted methylene chloride phase was washed with a saturated NaCl solution and dried using $MgSO_4$, followed by distillation under reduced pressure to minimize the remaining solvent. Hexane was added to precipitate a solid material. This solid material was filtered, purified using column chromatography, and dried in a vacuum for 3 hours to provide the compound of formula (14) with a yield of 50%.

$^1$H-NMR ($CDCl_3$, 300 MHz): 8.37 (s, 1H) 8.00~7.96 (m, 4H) 7.39~7.19 (m, 17H) 6.44~6.40 (m, 2H) 2.51 (s, 3H) 1.65 (s, 3H)

SYNTHESIS EXAMPLE 15

Synthesis of Ir(2-(5-phenyl-phenyl)-5-methylpyrazol)$_2$ (pic) of Formula (15)

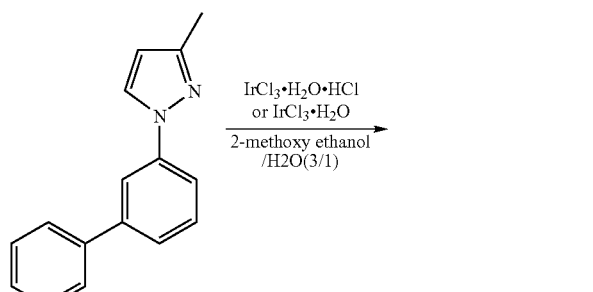

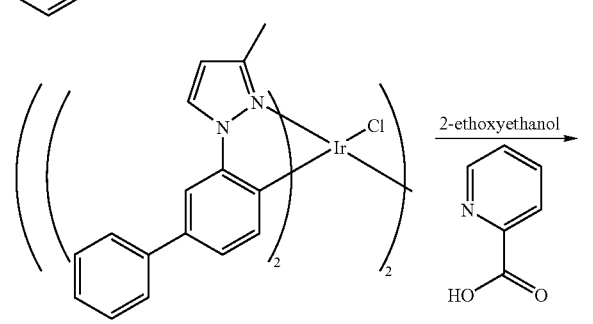

(15)

100 mL of 2-methoxy ethanol was stirred in a nitrogen atmosphere at room temperature for 30 minutes, and 4 mmol of iridium chloride hydrochloride hydrate and 10 mmol of 1-biphenyl-4-yl-3-methyl-1H-pyrazol were added and heated in a nitrogen atmosphere for 12 hours while stirring.

The progress of the reaction was checked using TLC to determine if the reaction had completed. After the completion of the reaction, the reaction product was distilled in a high vacuum to remove the solvent, followed by extraction using methylene chloride. The extracted methylene chloride phase was washed with a saturated NaCl solution and dried using $MgSO_4$, followed by distillation under reduced pressure to minimize the remaining solvent. Hexane was added to precipitate a solid material. This solid material was filtered and dried in a vacuum for about 3 hours to provide a dimer with a yield of 50%.

100 mL of 2-ethoxy ethanol were stirred in a nitrogen atmosphere at room temperature for 30 minutes, 5 mmol of the dimer, 15 mmol of picolinic acid, and 2.5 mL of 3N $Na_2CO_3$ were added and heated in a nitrogen atmosphere while stirring for 12 hours and checking the progress of the reaction using TLC to determine if the reaction had completed.

After the completion of the reaction, the reaction product was distilled in a high vacuum to remove the solvent, followed by extraction using methylene chloride. The extracted methylene chloride phase was washed with a saturated NaCl solution and dried using $MgSO_4$, followed by distillation under reduced pressure to minimize the remaining solvent. Hexane was added to precipitate a solid material. This solid material was filtered, purified using column chromatography, and dried in a vacuum for 3 hours to provide the compound of formula (15) with a yield of 50%.

$^1$H-NMR ($CDCl_3$, 300 MHz): 9.01 (t, J=3.58, 2H) 8.11 (s, 2H) 7.98 (d, J=1.70, 1H) 7.94~7.90 (m, 2H) 7.70~7.62 (m, 6H) 7.44~7.38 (m, 4H) 7.31~7.29 (m, 2H) 7.09~7.06 (m, 2H) 7.01 (d, J=7.41, 1H) 6.81 (t, J=2.49, 1H) 6.76 (t, J=2.54, 1H) 6.35 (d, J=7.80, 1H) 6.23 (d, J=7.80, 1H)

SYNTHESIS EXAMPLE 16

Synthesis of Fac Ir(ppz)$_2$(oppz) of Formula (16)

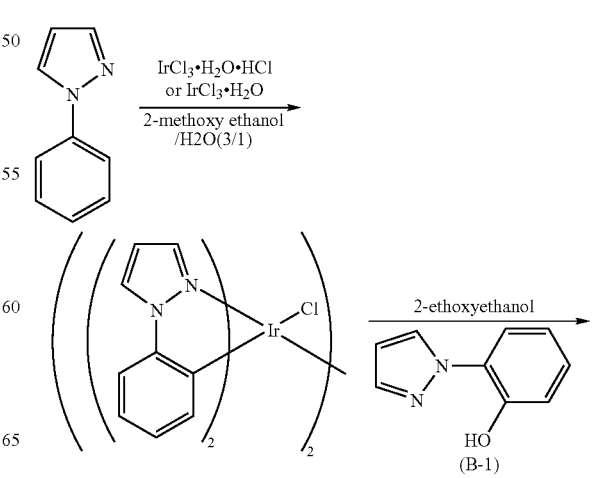

(B-1)

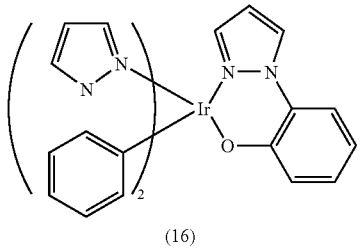

(16)

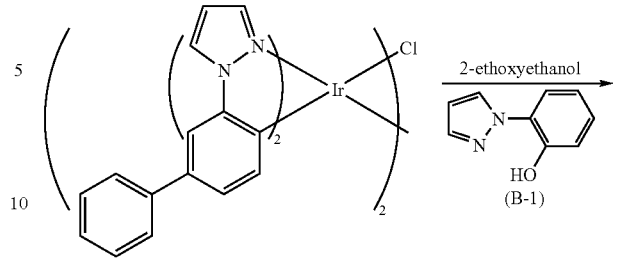

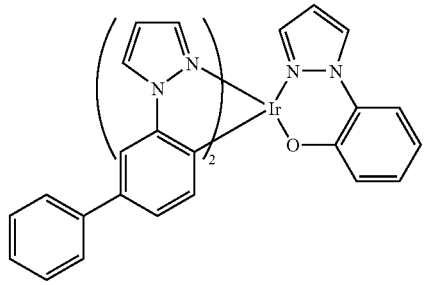

(17)

100 mL of 2-methoxy ethanol was stirred in a nitrogen atmosphere at room temperature for 30 minutes, and 4 mmol of iridium chloride hydrochloride hydrate and 10 mmol of ppz were added and heated in a nitrogen atmosphere for 12 hours while stirring.

The progress of the reaction was checked using TLC to determine if the reaction had completed. After the completion of the reaction, the reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. T his solid material was filtered and dried in a vacuum for about 3 hours to provide a dimer with a yield of 50%.

100 mL of 2-ethoxy ethanol were stirred in a nitrogen atmosphere at room temperature for 30 minutes, 5 mmol of the dimer, 15 mmol of compound (B-1), and 2.5 mL of 3N Na$_2$CO$_3$ were added and heated in a nitrogen atmosphere while stirring for 12 hours and checking the progress of the reaction using TLC to determine if the reaction had completed.

After the completion of the reaction, the reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered, purified using column chromatography, and dried in a vacuum for 3 hours to provide the compound of formula (16) with a yield of 50%.

$^1$H-NMR (CDCl$_3$, 300 MHz): 8.02 (d, J=2.76, 1H) 7.96~7.92 (m, 2H) 7.32 (d, J=1.89, 1H) 7.17~7.02 (m, 7H) 6.89~6.82 (m, 2H) 6.74~6.66 (m, 2H) 6.62~6.54 (m, 1H) 6.50~6.36 (m, 4H) 6.23 (d, J=7.35, 1H)

SYNTHESIS EXAMPLE 17

Synthesis of Ir(2-(5-phenyl)-phenylpyrazol)$_2$ (oppz) of Formula (17)

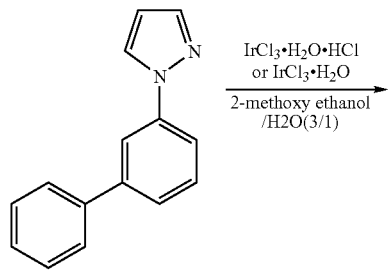

100 mL of 2-methoxy ethanol was stirred in a nitrogen atmosphere at room temperature for 30 minutes, and 4 mmol of iridium chloride hydrochloride hydrate and 10 mmol of 1-biphenyl-3-yl-1H-pyrazol were added and heated in a nitrogen atmosphere for 12 hours while stirring.

The progress of the reaction was checked using TLC to determine if the reaction had completed. After the completion of the reaction, the reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered and dried in a vacuum for about 3 hours to provide a dimer with a yield of 50%.

100 mL of 2-ethoxy ethanol were stirred in a nitrogen atmosphere at room temperature for 30 minutes, 5 mmol of the dimer, 15 mmol of the compound (B-1), and 2.5 mL of 3N Na$_2$CO$_3$ were added and heated in a nitrogen atmosphere while stirring for 12 hours and checking the progress of the reaction using TLC to determine if the reaction had completed.

Figure 6:
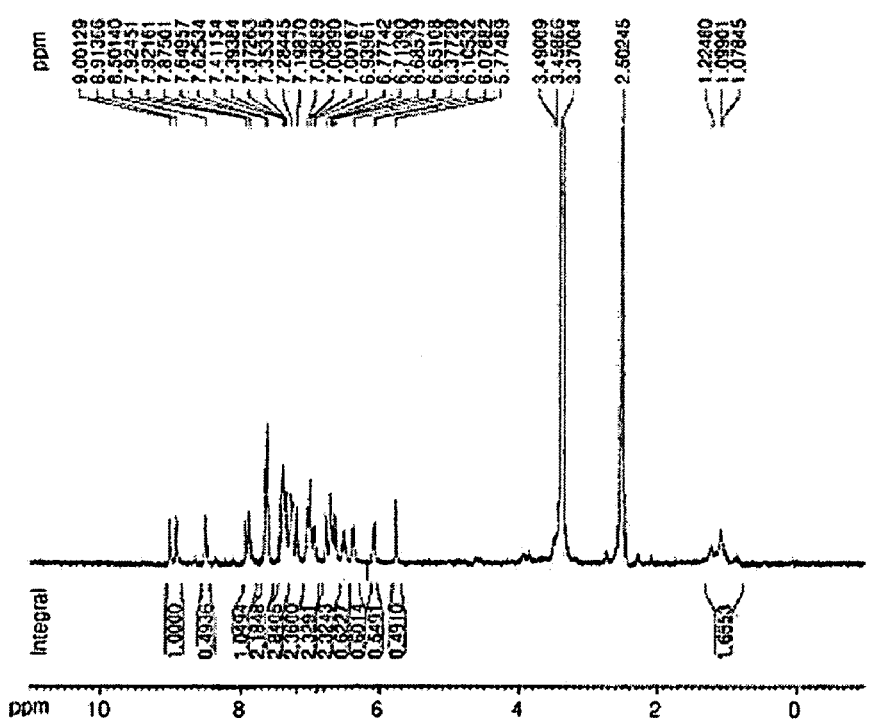
FIG. 6 is the NMR spectrum of an iridium compound of formula (17) according to the embodiments of the present invention in $CHCl_3$ solution.

After the completion of the reaction, the reaction product was distilled in a high vacuum to remove the solvent, followed by extraction using methylene chloride. The extracted methylene chloride phase was washed with a saturated NaCl solution and dried using MgSO$_4$, followed by distillation under reduced pressure to minimize the remaining solvent. Hexane was added to precipitate a solid material. This solid material was filtered, purified using column chromatography, and dried in a vacuum for 3 hours to provide the compound of formula (17) with a yield of 50%. An NMR spectrum of the compound of formula (17) dissolved in CHCl$_3$ is illustrated in FIG. 6.

The hotoluminescence (PL) characteristics of the iridium compounds with formulae (4), (5), (7), and (8) produced in the above synthesis examples were observed. The resulting PL spectra are illustrated in FIG. 2.

Figure 2:
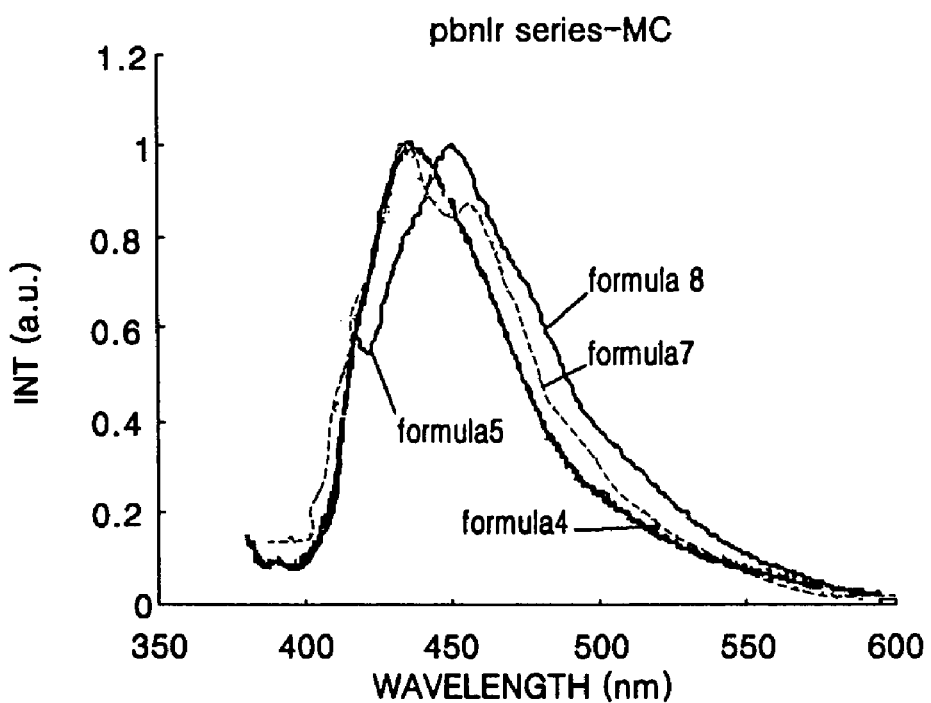
FIG. 2 is the photoluminescence (PL) spectra of iridium compounds having formulae (4), (5), (7), and (8) according to the embodiments of the present invention in $CH_2Cl_2$ solution.

As is apparent from FIG. 2, the iridium compounds were found to be photoluminescent in a deep blue range from 435 nm to 450 nm.

The PL characteristics at a low temperature of 77K, not at room temperature, were observed using the iridium compounds of formulae (7) and (8) to identify emission peaks originating from, for example, a metal-to-ligand charge transfer state or the ligand centered state. The results are shown in FIGS. 3 and 4.

Figure 3:
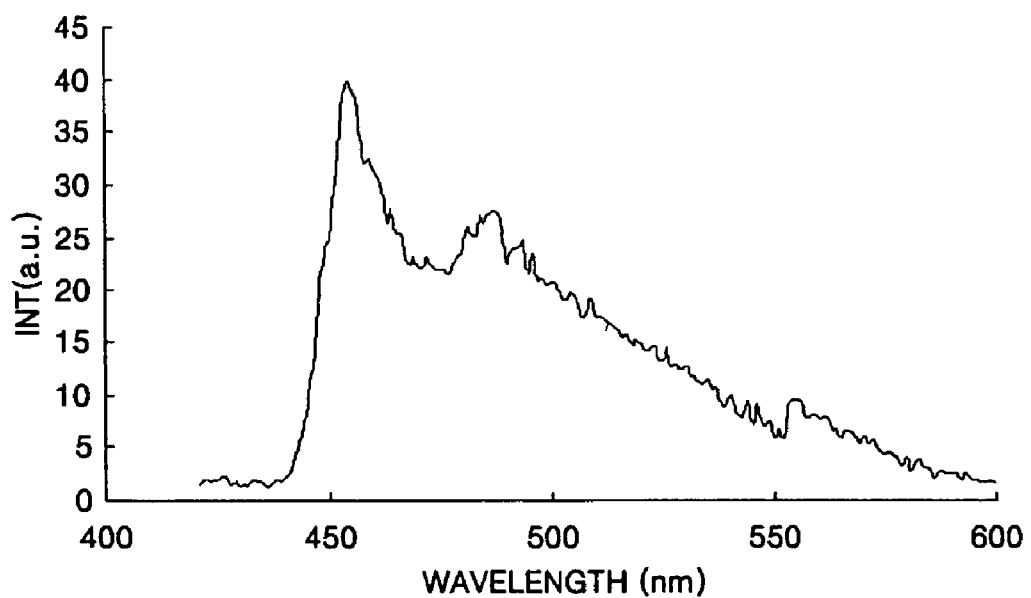
FIG. 3 is the PL spectrum at 77K of the iridium compound of formula (7) according to the present invention.
Figure 4:
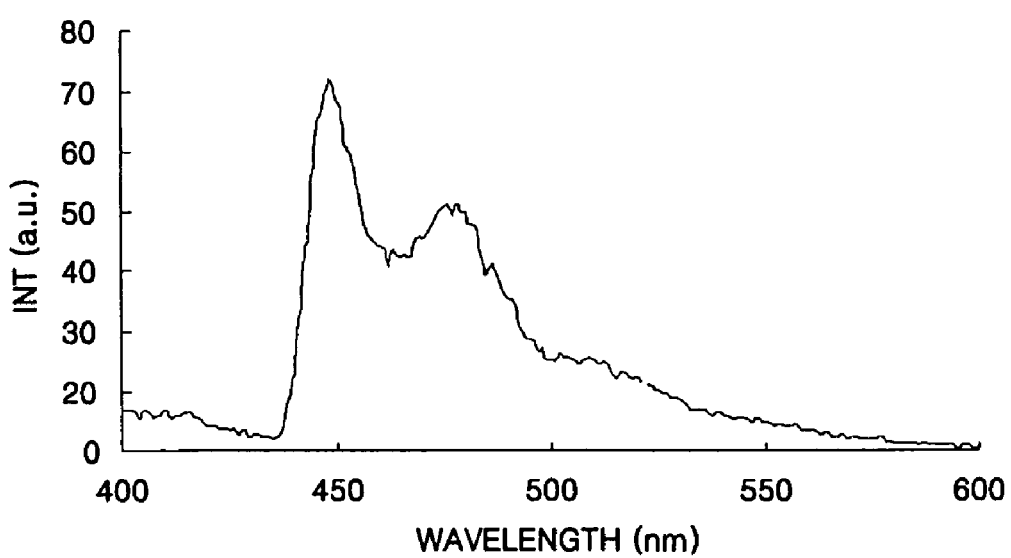
FIG. 4 is the PL spectrum at 77K of the iridium compound of formula (8) according to the embodiments of the present invention.

As is apparent from FIGS. 3 and 4, the main emission peaks of the two iridium compounds appear in the deep blue region in the range of 454 nm to 448 nm.

Figure 5:
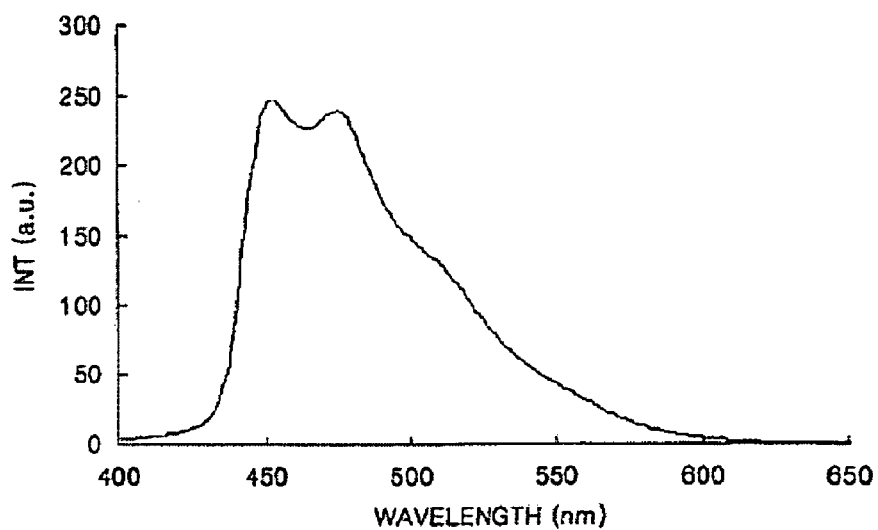
FIG. 5 is the PL spectrum of a solid film manufactured by doping 94 parts by weight of polymethylmethacrylate (PMMA) with 6 parts by weight of the compound of formula (8) according to the embodiments of the present invention.

The solid PL characteristics of the iridium compound of formula (8) was measured using a solid film manufactured by doping polymethylmethacrylate (PMMA) with the iridium compound of formula (8). PMMA is a non-emissive polymer and does not affect the emission properties of the iridium compound film. In particular, the solid film was manufactured by doping 94 parts by weight of PMMA with 6 parts by weight of the iridium compound of formula (8). The results are shown in FIG. 5. As shown in FIG. 5, the compound of formula (8) has a main emission peak near 452 nm in the blue range even when processed into a thin film, indicating that red shifting due to self-aggregation is minimal.

Figure 7:
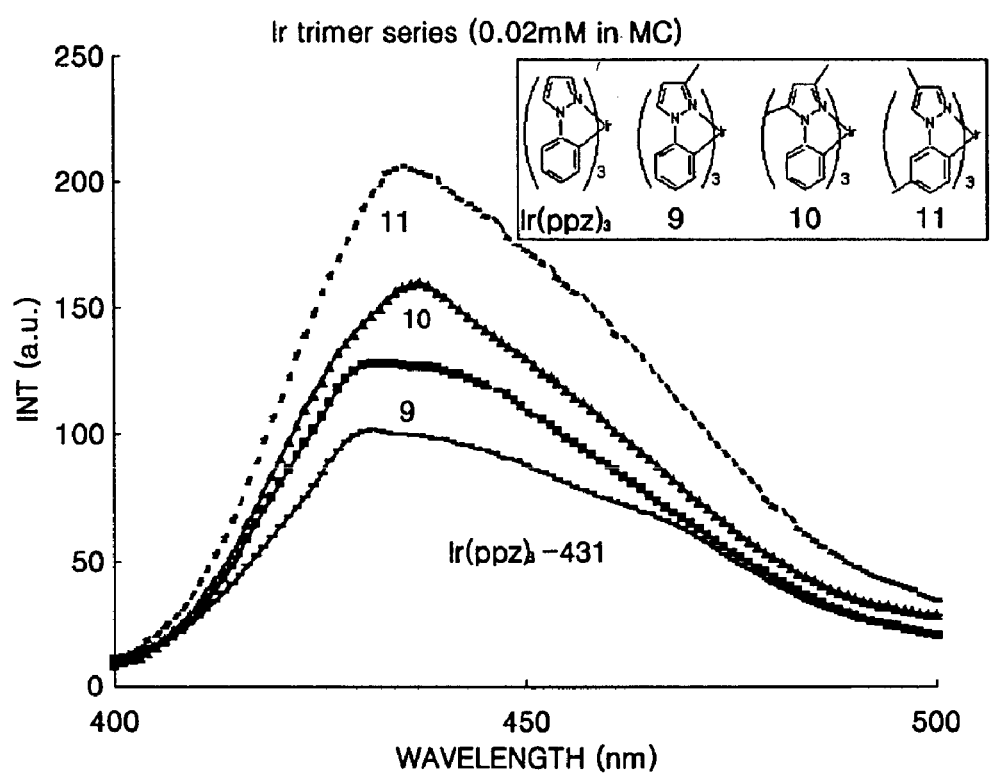
FIG. 7 is the PL spectra of Ir(ppz)$_3$ and iridium compounds of formulae (9), (10), and (11) in $CH_2Cl_2$ solution.

The PL characteristics of the iridium compounds of formulas (9), (10), and (11) prepared in the above synthesis examples and Ir(ppz)$_3$ when dissolved in CH$_2$Cl$_2$ solution were measured. The results are shown in FIG. 7. As is apparent from FIG. 7, the iridium compounds of formulas (9), (10), and (11) emit light near 440 nm in the deep blue region and have greater emission efficiencies than Ir(ppz)$_3$.

The PL characteristics of the iridium compound of formula (11) in CH$_2$Cl$_2$ solution were measured at room temperature and at 77K. The results are shown in FIG. 8. As is apparent from FIG. 8, the iridium compound of formula (11) emits light near 435 m in the deep blue range both at room temperature and at 77K.

Figure 9:
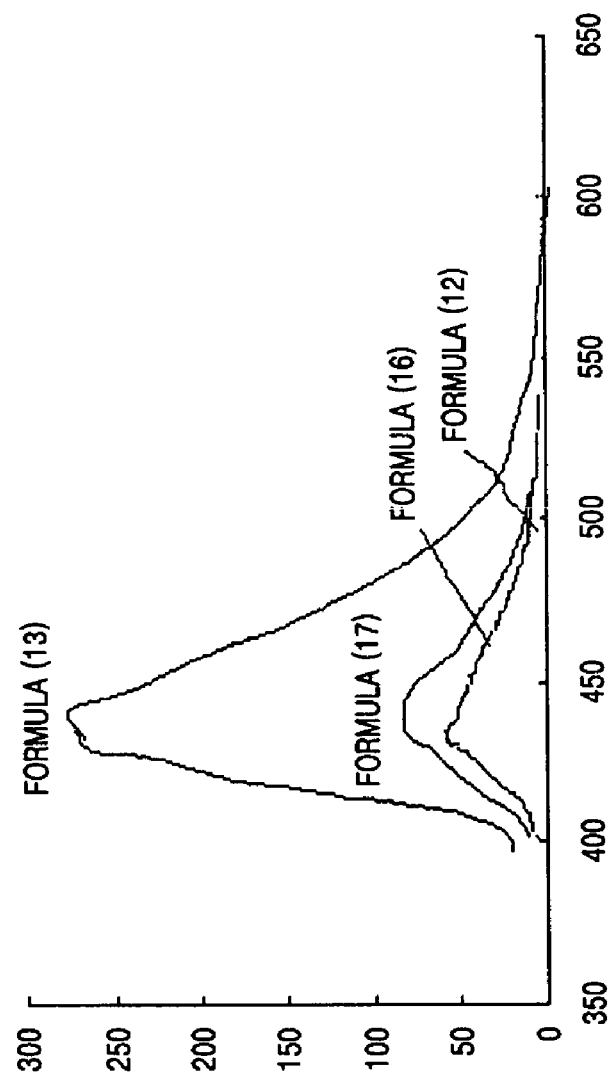
FIG. 9 is the PL spectra of iridium compounds of formulae (12), (13), (16), and (17) according to the embodiments of the present invention in $CH_2Cl_2$ solution.
Figure 9:
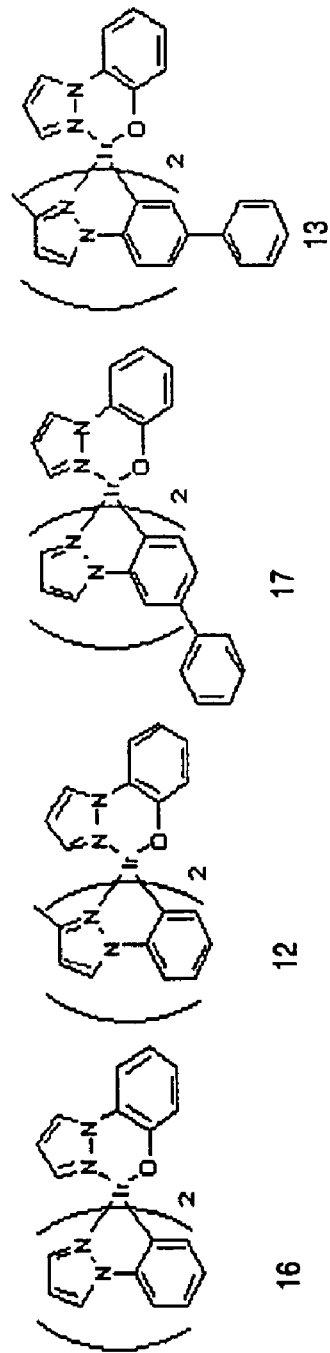

The PL characteristics of the compounds of formulae (12), (13), (16), and (17) prepared in the above synthesis examples were measured when dissolved in CH$_2$Cl$_2$ solution. The results are shown in FIG. 9. As shown in FIG. 9, the iridium compounds of formulae (12), (13), (16), and (17) emit light near 430 nm and 440 nm in the blue range, and the emission intensity of the iridium compound of formula (13) is greater than the emission intensities of the compounds of formulae (12), (16), and (17) when the concentrations of the compounds are all equal.

Figure 10:
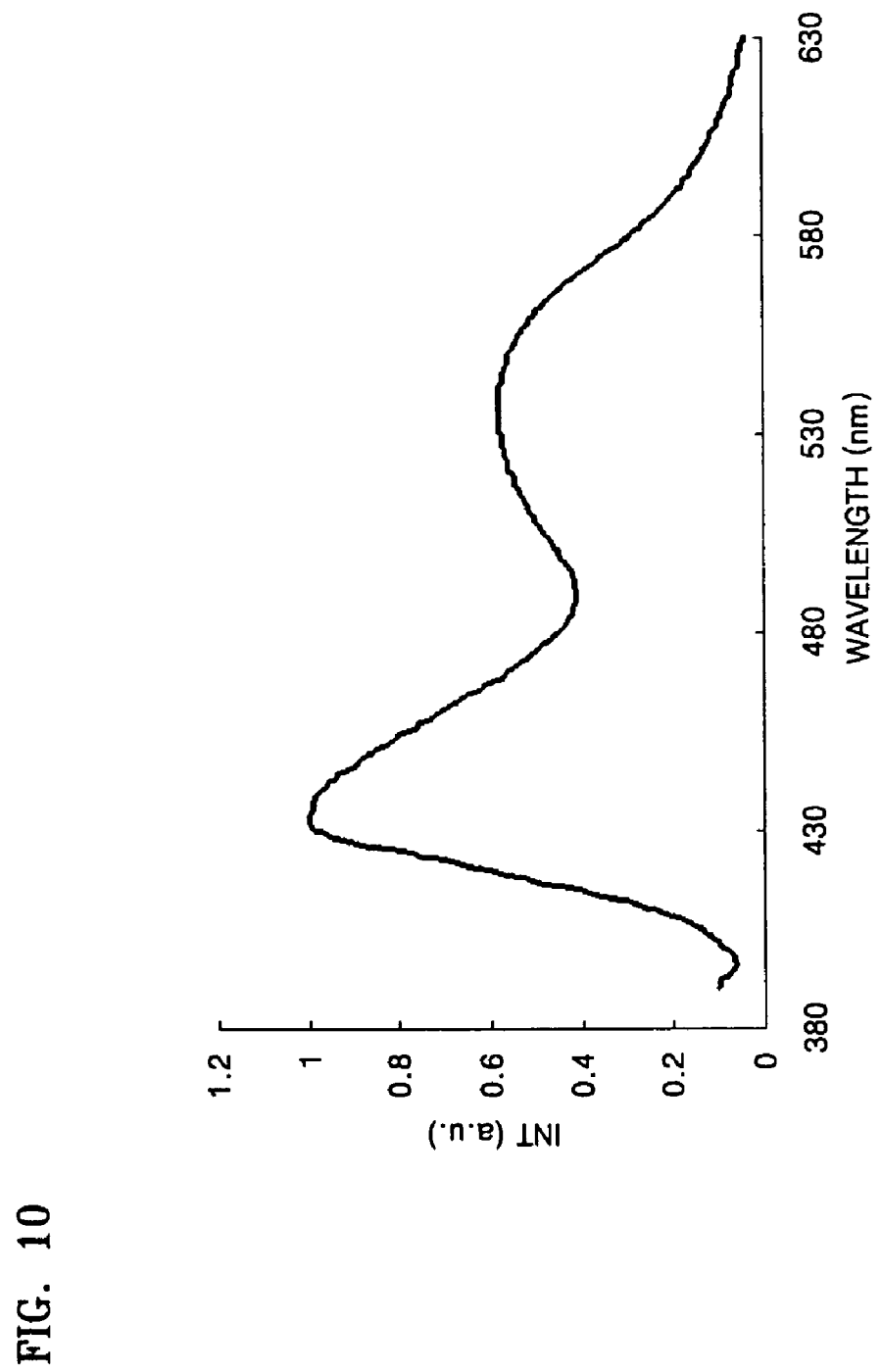
FIG. 10 is the PL spectrum of an iridium compound of formula (15) according to the embodiments of the present invention in $CH_2Cl_2$ solution.
Figure 11:
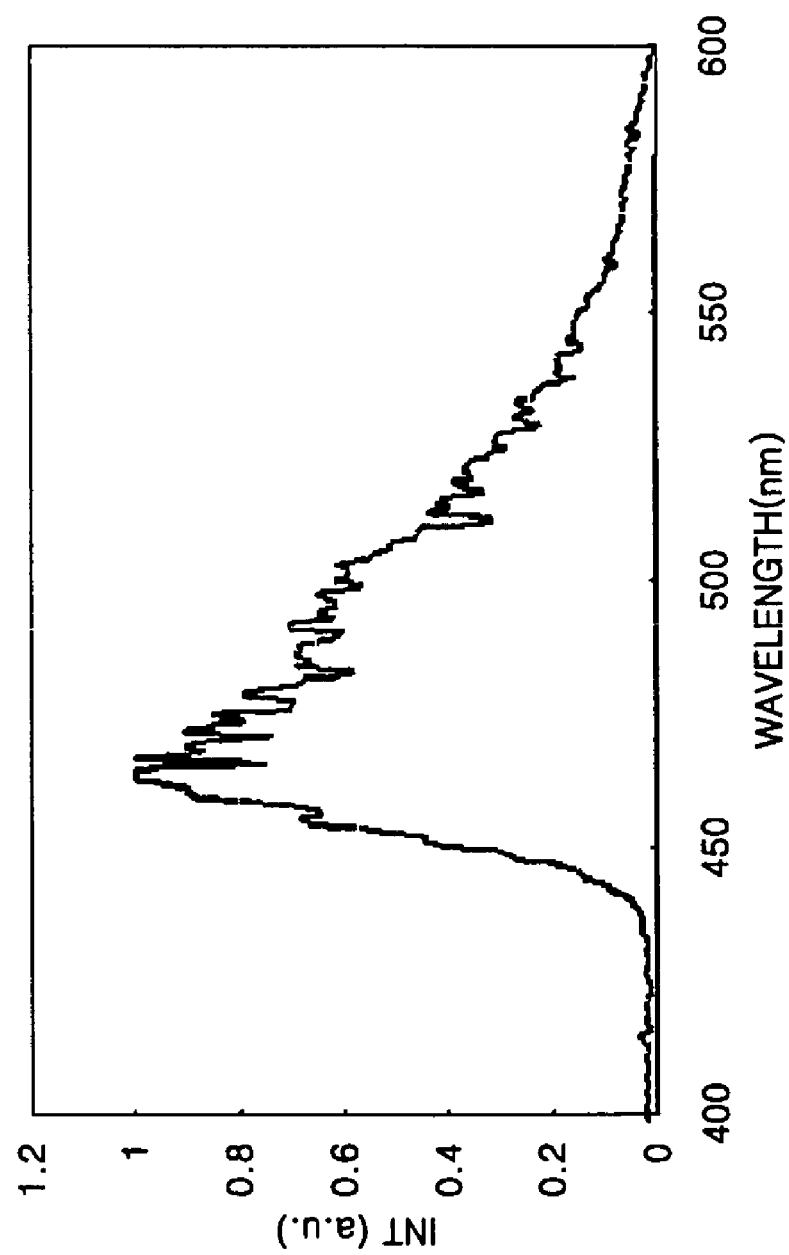
FIG. 11 is the PL spectrum of the iridium compound of formula (17) according to the embodiments of the present invention at 77K.

The PL characteristics of the iridium compound of formula (15) in CH$_3$Cl$_2$ solution and the PL characteristics of the iridium compound of formula (17) at 77K were measured. The results are shown in FIGS. 10 and 11, respectively. As is apparent from FIGS. 10 and 11, the iridium compound of formula (15) has a main emission peak at 432 nm, and the iridium compound of formula (17) has a main emission peak at 463 nm, which are both in the blue range.

SYNTHESIS EXAMPLE 18

Synthesis of Compound (A-1)

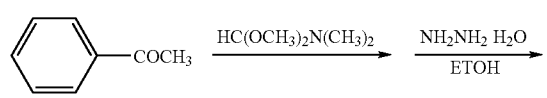

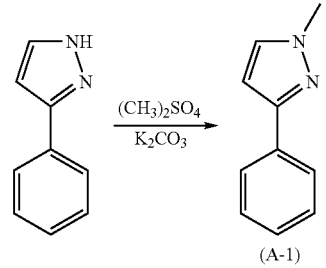

249.8 mmol of acetophenone was added to 1399 mmol of N,N-dimethylformamide dimethylacetal and refluxed for 1 hour. 217.6 mmol of hydrazine monohydrate and 100 mL of ethanol were added to the reaction product and refluxed further for 1 hour.

The progress of the reaction was checked using TLC to determine if the reaction had completed. After the completion of the reaction, 213.5 mmol of dimethyl sulfate, acetone, and 234.9 mmol of potassium carbonate were added to the reaction product and refluxed for 1 hour to obtain compound (A-1) with a yield of 29.6%.

The structure of compound (A-1) was identified using NMR. The result is shown in FIG. 13a.

SYNTHESIS EXAMPLE 19

Synthesis of Compound (B-1)

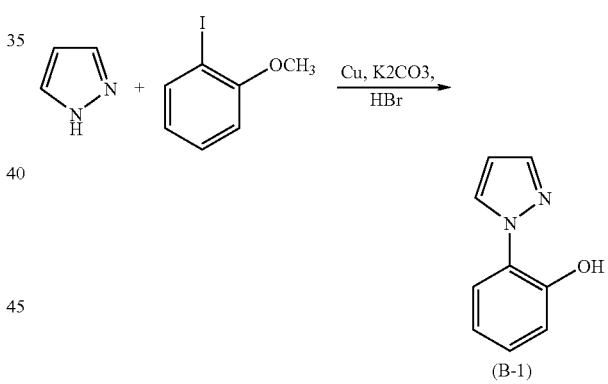

7.86 mmol of copper, 210.6 mmol of potassium carbonate, and 10 mL of nitrobenzene were placed in a sealed tube. 35.10 mmol of pyrazole and 35.10 mmol of 2-idozoanisole were added into the reaction mixture, and the tube was plugged and heated under reflux for 10 hours while stirring the mixture. 50 mL of 48% HBr was added into the product and refluxed further 10 hours to obtain compound (B-1) with a yield of 83.5%.

SYNTHESIS EXAMPLE 20

Synthesis of Compound of Formula (33)

20 mL of ethylcellosolve was stirred in a nitrogen atmosphere at room temperature for 30 minutes, and 26.1 mmol of compound (A-1) and 13.05 mmol of iridium chloride hydrochloride hydrate were added thereto and heated while stirring for 24 hours and checking the progress of the reaction using TLC to determine if the reaction had completed. The reaction products were subjected to extraction using methylene chloride. The extracted methylene chloride phase was treated using MgSO₄ to remove water, filtered, and dried in a vacuum for 3 hours to obtain a dimer with a yield of 70.7%.

3.755 mmol of the dimer and 7.51 mmol of compound (B-1) were added to 20 mL of ethylcellosolve at room temperature, and 8.26 mL of Na₂CO₃ were added, as a basic component, to the mixture, followed by heating in a nitrogen atmosphere for 24 hours while stirring the mixture and checking the progress of the reaction using TLC to determine if the reaction had completed. As a result, the compound of formula (33) was obtained with a yield of 20%.

Figure 13B:
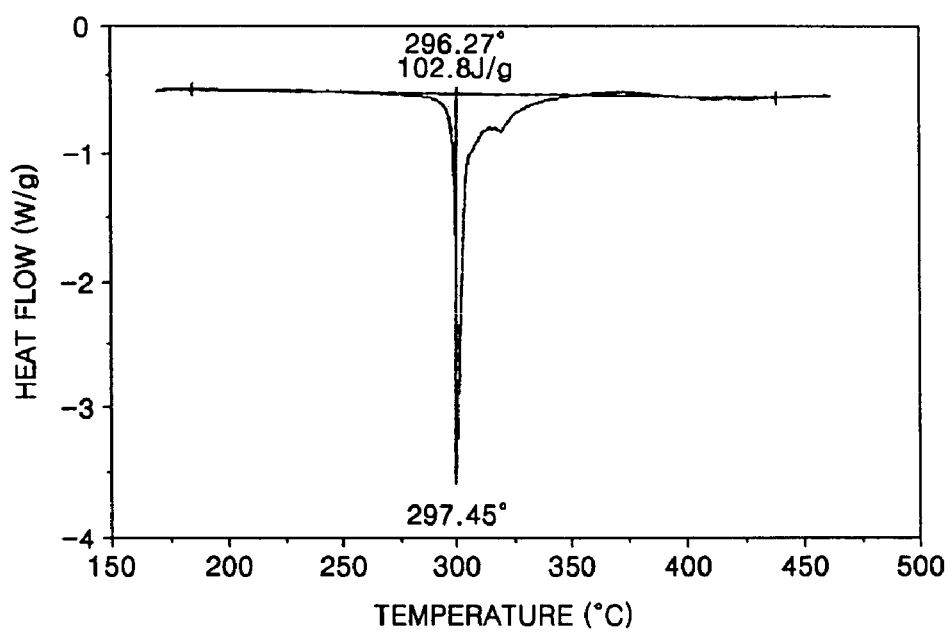
FIG. 13B is the differential scanning calorimetry (DSC) curve of an organic electroluminescent (EL) compound of formula (33) according to the embodiments of the present invention.
Figure 14:
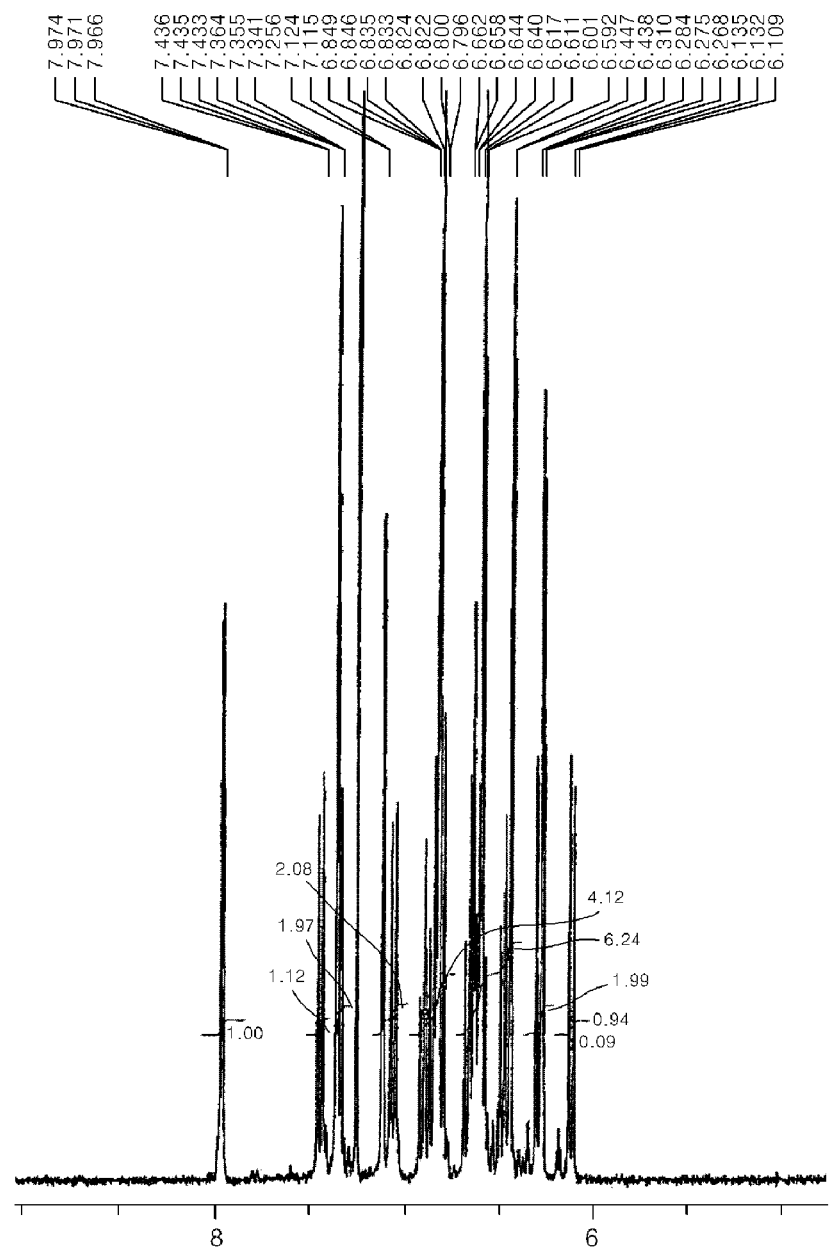
FIG. 14 is the NMR spectrum of the organic EL compound of formula (33) according to the embodiments of the present invention in $CHCl_3$ solution.
Figure 15:
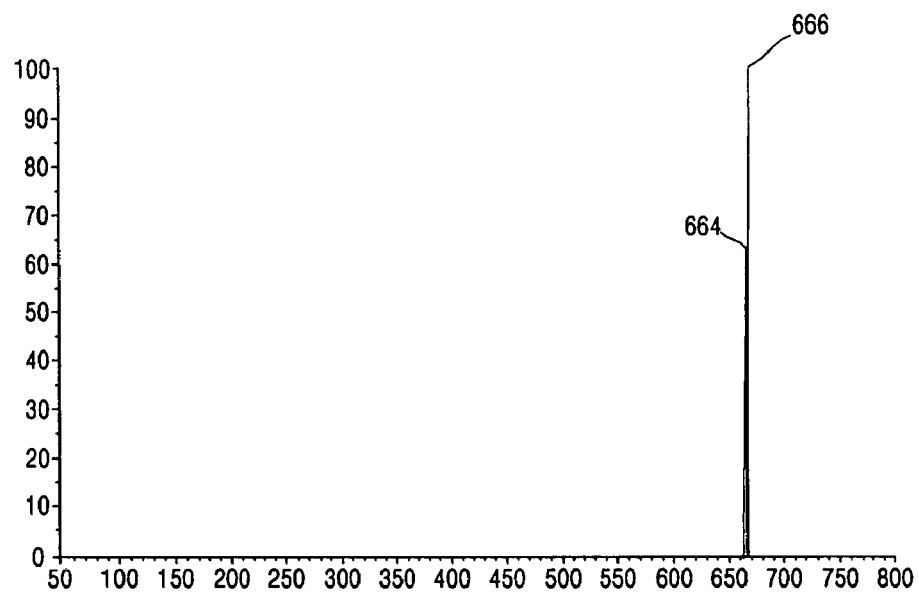
FIG. 15 is a graph illustrating the result of a mass analysis performed on the organic EL compound of formula (33) according to the embodiments of the present invention.
Figure 16:
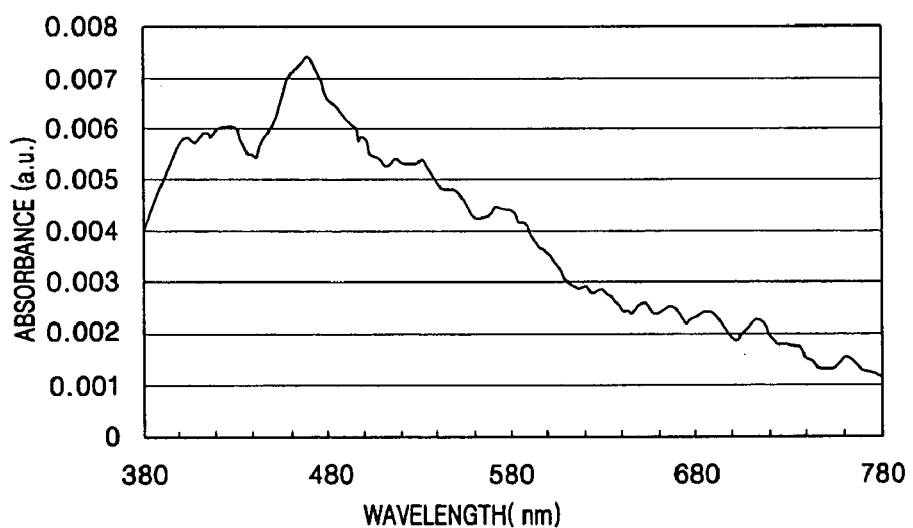
FIG. 16 is the PL spectrum of the organic EL compound of formula (33) in solid state according to the embodiments of the present invention.

The structure and mass of the compound of formula (33) were analyzed using NMR and mass spectrometry, respectively. The results are shown in FIGS. 14 and 5. The thermal characteristics of the compound of formula (33) can be inferred based on data obtained by the analysis of the DSC curve of FIG. 13B. As shown in FIG. 13B, the Tm of the compound of formula (33) is 296° C. FIG. 16 is a PL spectrum of the compound of formula (33) in solid state. As shown in FIG. 16, the compound of formula (33) emits blue light at 460 nm.

SYNTHESIS EXAMPLE 21

Synthesis of Compound (C-1)

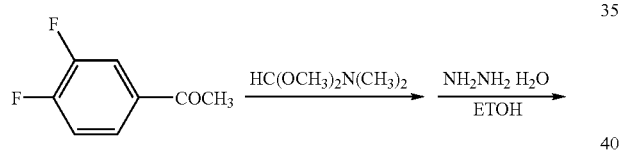

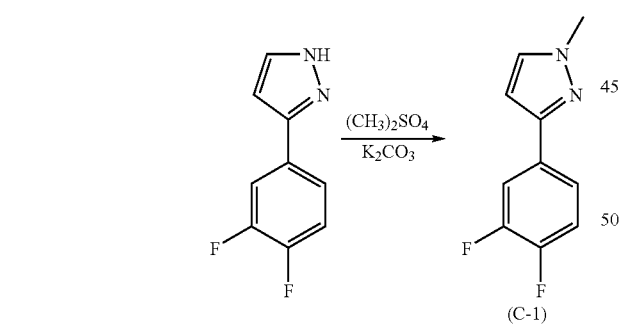

171.5 mmol of 3,4-difluoroacetophenoene and 686 mmol of N,N-dimethylformamide dimethylacetal were mixed together and refluxed for 1 hour. 106.7 mmol of hydrazine monohydrate was added to the reaction product and refluxed using ethanol solvent for 1 hour. 103 mmol of dimethyl sulfate and 113.3 mmol of K₂CO₃ were added to the resulting product and refluxed using 100 mL of acetone for 3 hours to obtain compound (C-1) with a yield of 30%.

Figure 17:
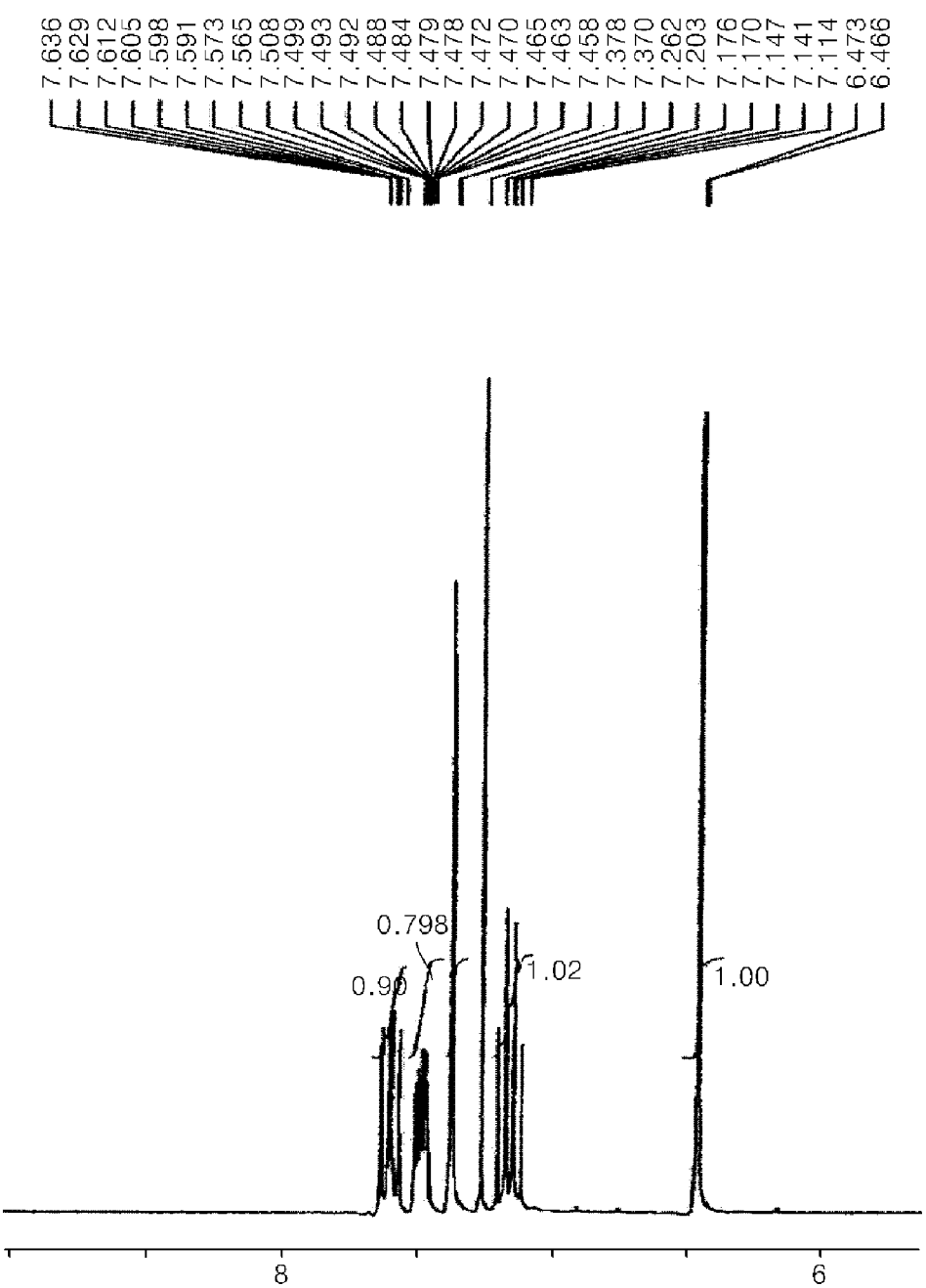
FIG. 17 is the NMR spectrum of a compound of formula (C-1) according to the embodiments of the present invention in CHCl₃ solution.
Figure 18:
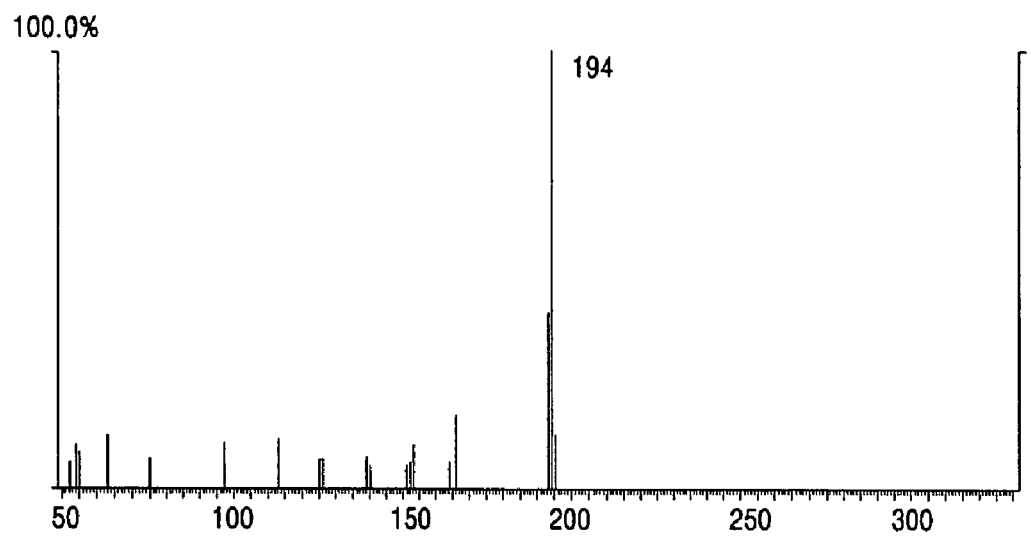
FIG. 18 is a graph illustrating the result of a mass analysis performed on the compound of formula (C-1) according to the embodiments of the present invention.

The structure and mass of compound (C-1) were analyzed using NMR and mass spectrometry, respectively. The results are shown in FIGS. 17 and 18.

SYNTHESIS EXAMPLE 22

Synthesis of Compound of Formula (34)

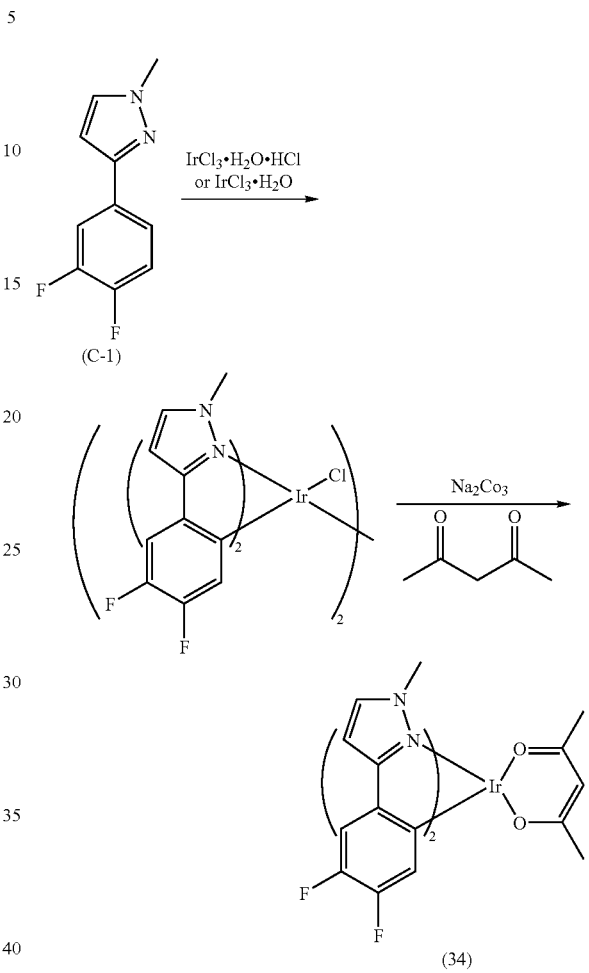

10 mL of ethylcellosolve was stirred in a nitrogen atmosphere at room temperature for 30 minutes, and 13.7 mmol of compound (C-1) and 6.85 mmol of iridium (III) chloride were added thereto and heated while stirring for 24 hours and checking the progress of the reaction using TLC to determine if the reaction had completed. The reaction products were subjected to extraction using methylene chloride. The extracted methylene chloride phase was treated using MgSO₄ to remove water, filtered, and dried in a vacuum for 3 hours to obtain a dimer with a yield of 95.1%.

10 mL of ethylcellosolve was stirred in a nitrogen atmosphere at room temperature for 30 minutes, 2.46 mmol of the dimer, 4.92 mmol of acetyl acetone, and 5.412 mL of Na₂CO₃ as a base component were added thereto, followed by heating in a nitrogen atmosphere for 24 hours while stirring the mixture and checking the progress of the reaction using TLC to determine if the reaction had completed. As a result, the compound of formula (34) was obtained with a yield of 30%.

Figure 19:
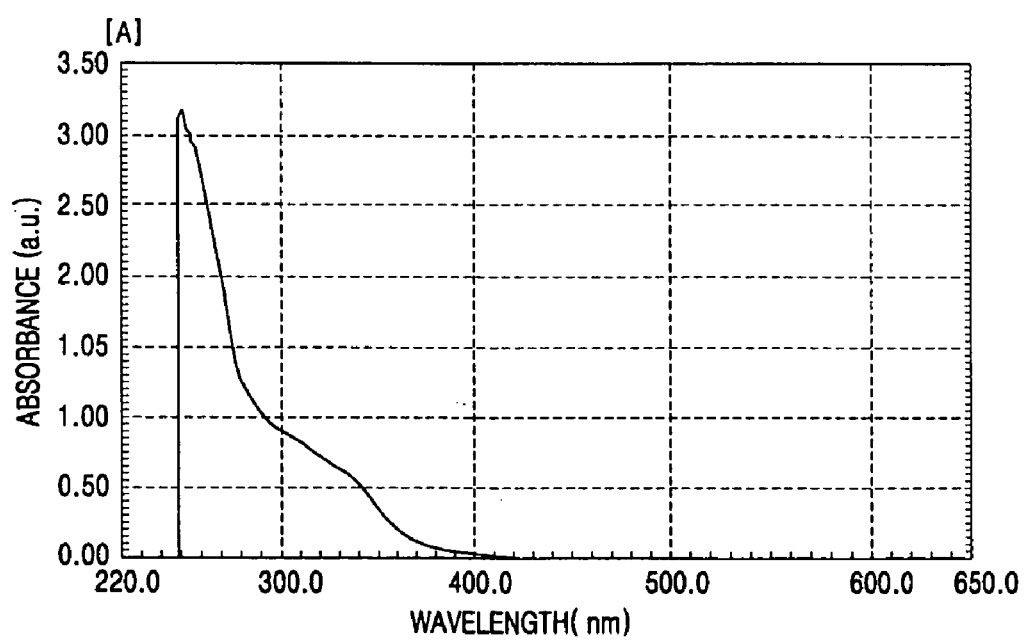
FIG. 19 is the absorption spectrum of an organic EL compound of formula (34) according to the embodiments of the present invention.
Figure 20:
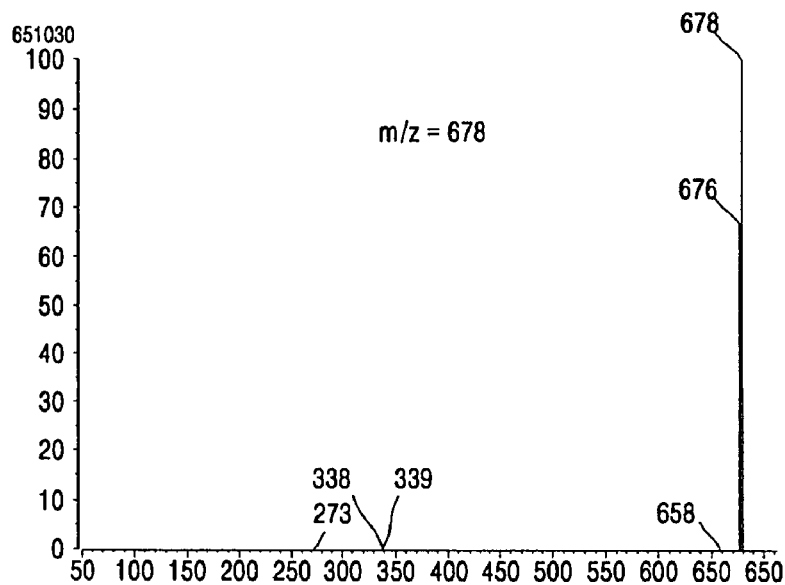
FIG. 20 is a graph illustrating the result of a mass analysis performed on the organic EL compound of formula (34) according to the embodiments of the present invention.
Figure 21:
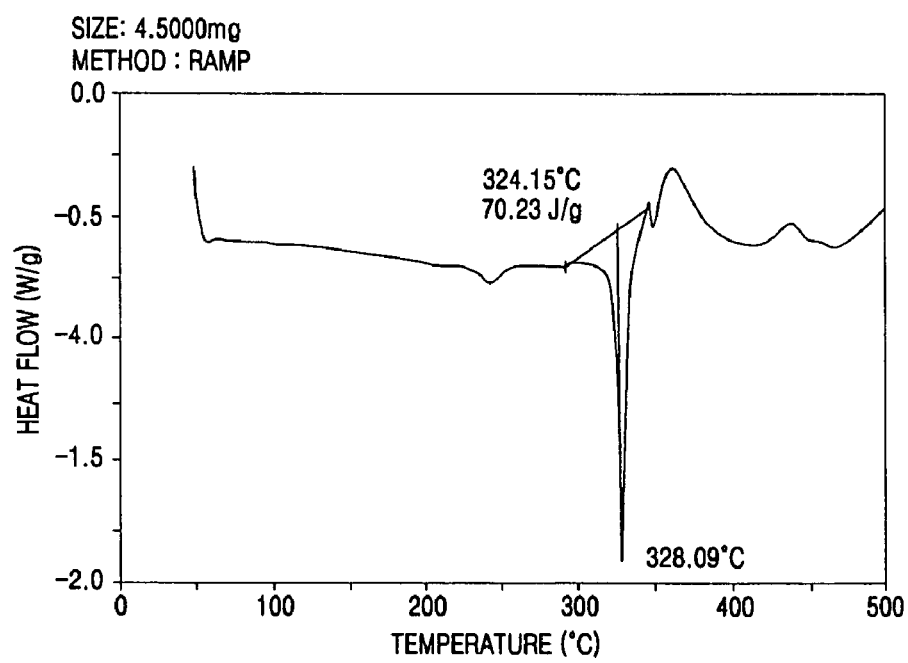
FIG. 21 is the DSC curve of the organic EL compound of formula (34) according to the embodiments of the present invention.

The mass of the compound of formula (34) was measured using mass spectrometry. The result is shown in FIG. 20. FIG. 19 illustrates the light absorption characteristics of the compound of formula (34), and FIG. 21 is the DSC curve of the compound of formula (34). As shown in FIGS. 19 and 21, the compound of formula (34) has an absorption peak at 230 nm, and the Tm thereof is 324° C.

SYNTHESIS EXAMPLE 23

Synthesis of Compound (D-1)

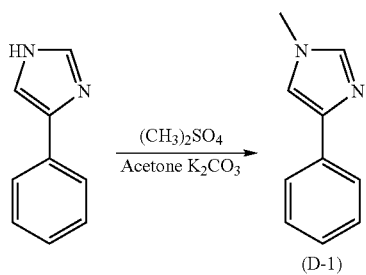

(D-1)

92.04 mmol of 1H-4-phenylimidazole, 92.04 mmol of dimethyl sulfate, and 101.2 mmol of $K_2CO_3$ were placed in a sealed tube, and the tube was plugged and heated under reflux for about 3 hours while stirring the mixture and checking the progress of the reaction using TLC to determine if the reaction had completed. As a result, compound (D-1) was obtained with a yield of 41.2%.

Figure 22:
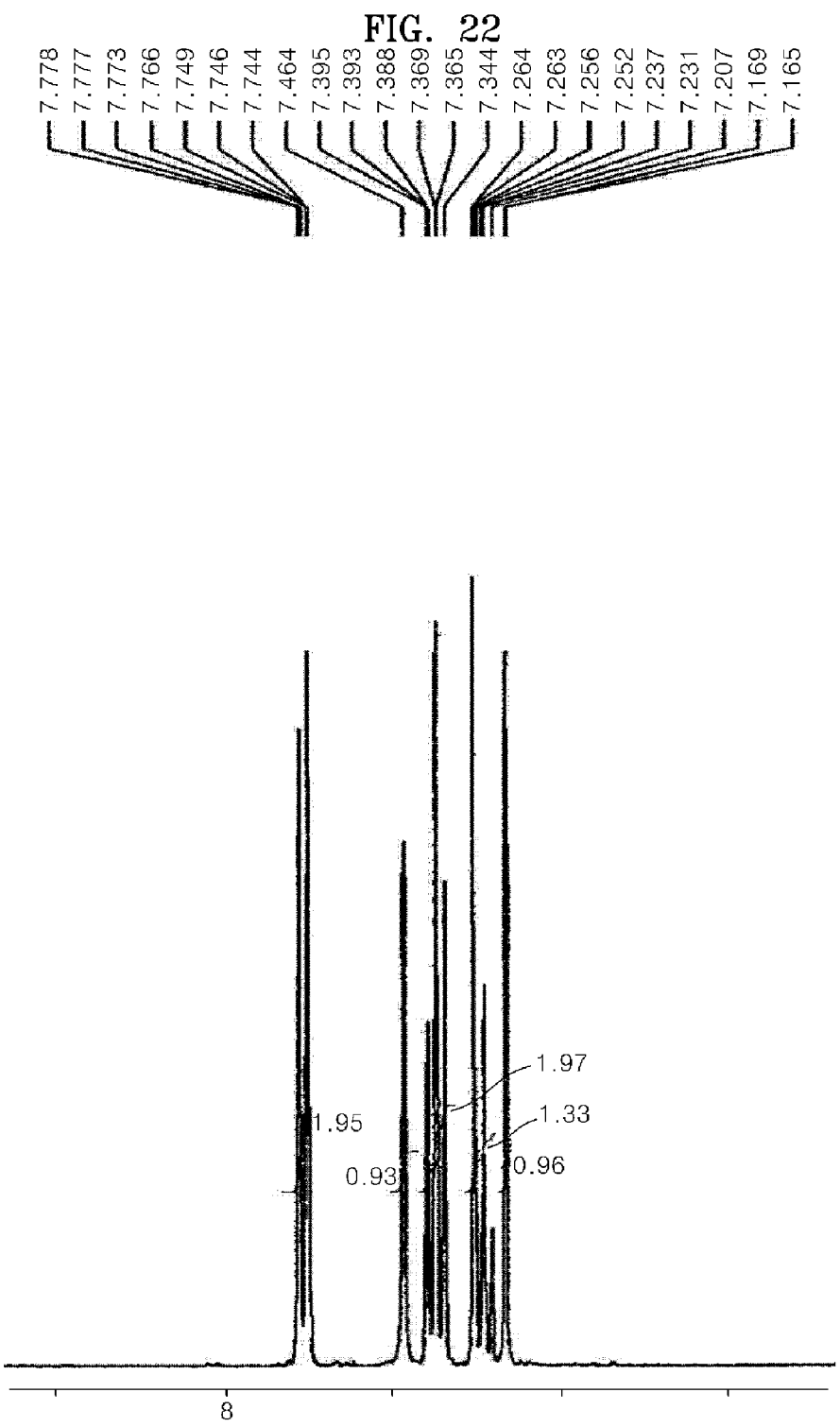
FIG. 22 is the NMR spectrum of a compound of formula (D-1) according to the embodiments of the present invention in CHCl₃ solution.
Figure 23:
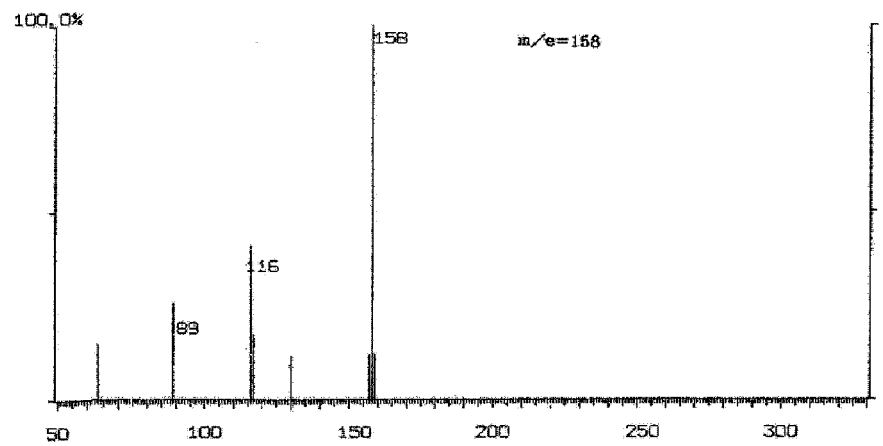
FIG. 23 is a graph illustrating the result of a mass analysis performed on the compound of formula (D-1) according to the embodiments of the present invention.

The structure and mass of compound (D-1) were analyzed using NMR and mass spectrometry, respectively. The results are shown in FIGS. 22 and 23.

SYNTHESIS EXAMPLE 24

Synthesis of Compound of Formula (37)

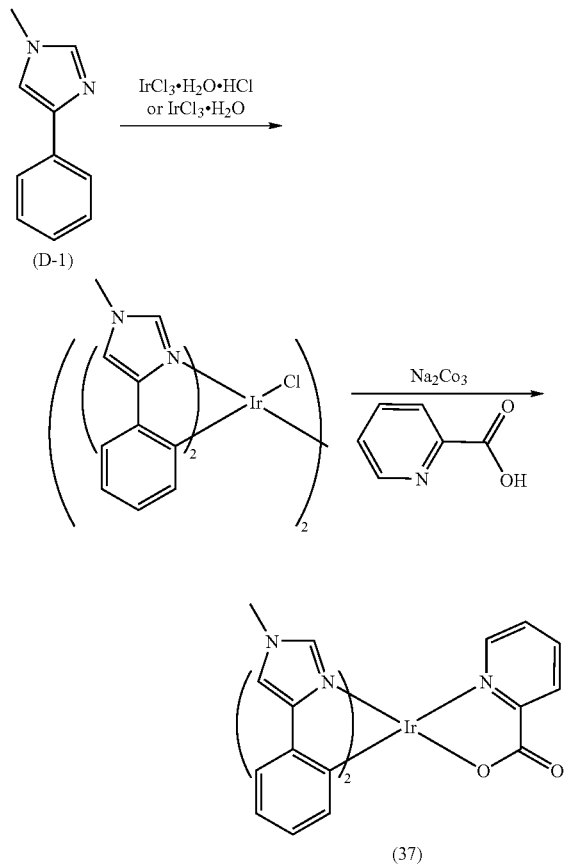

(37)

10 mL of ethylcellosolve was stirred in a nitrogen atmosphere at room temperature for 30 minutes, and 16.58 mmol of the compound of the compound (D-1) and 8.292 mmol of iridium (III) chloride were added thereto and heated while stirring for 24 hours and checking the progress of the reaction using TLC to determine if the reaction had completed. The reaction products were subjected to extraction using methylene chloride. The extracted methylene chloride phase was treated using $MgSO_4$ to remove water, filtered, and dried in a vacuum for 3 hours to obtain a dimer with a yield of 44.5%.

10 mL of 1,2-dichloroethane was stirred in a nitrogen atmosphere at room temperature for 30 minutes, 1.487 mmol of the dimmer, 2.974 mmol of 2-pyrridine carboxylic acid, and 5.412 mL of $Na_2CO_3$ as a base component were added thereto, followed by heating in a nitrogen atmosphere for 24 hours while stirring the mixture and checking the progress of the reaction using TLC to determine if the reaction had completed. As a result, the compound of formula (37) was obtained with a yield of 53.5%.

Figure 24:
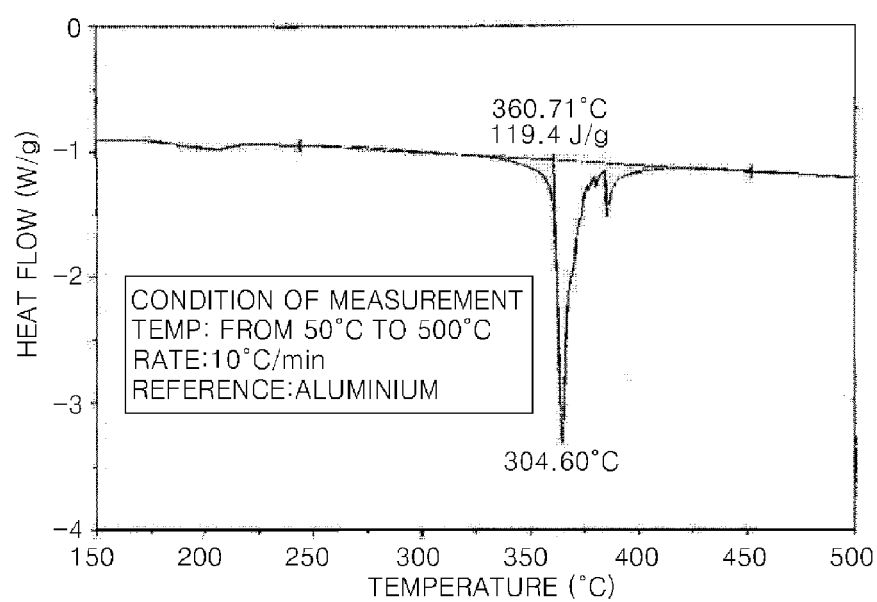
FIG. 24 is the DSC curve of an organic EL compound of formula (37) according to the embodiments of the present invention.
Figure 25:
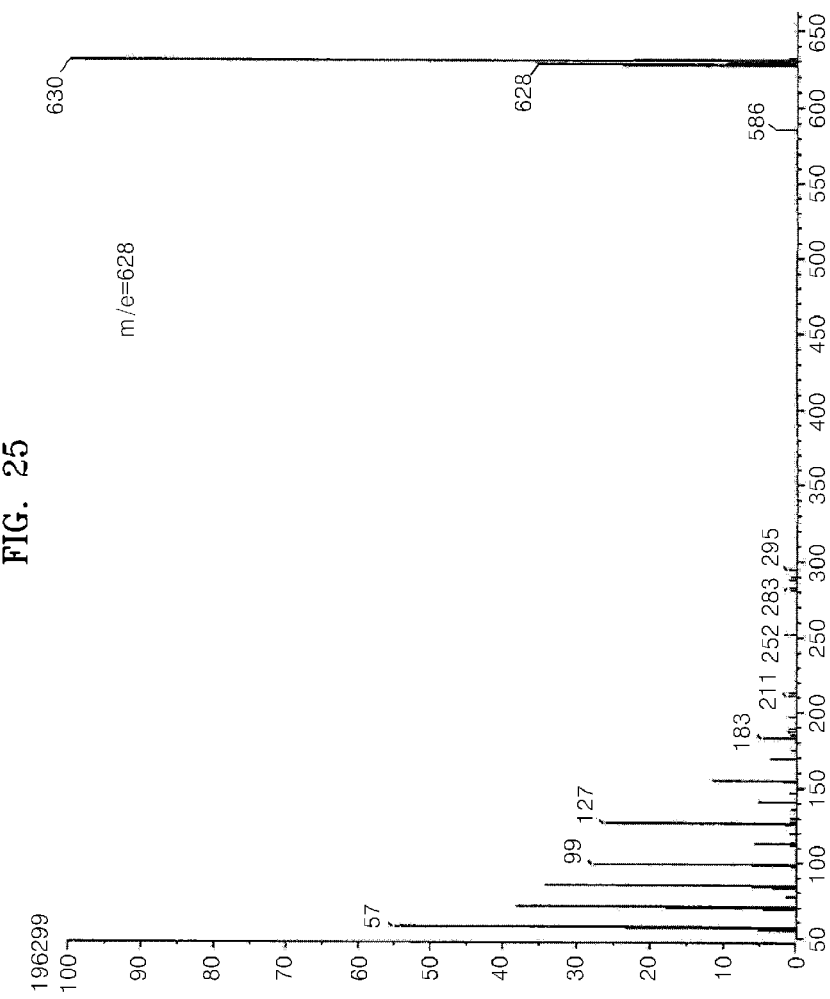
FIG. 25 is a graph illustrating the result of a mass analysis performed on the organic EL compound of formula (37) according to the embodiments of the present invention.

FIG. 24 is the DSC curve of the compound of formula (37). As shown in FIG. 24, the Tm of the compound of formula (37) is 361° C. The mass of the compound (37) is shown in FIG. 25.

SYNTHESIS EXAMPLE 25

Synthesis of Compound of Formula (36)

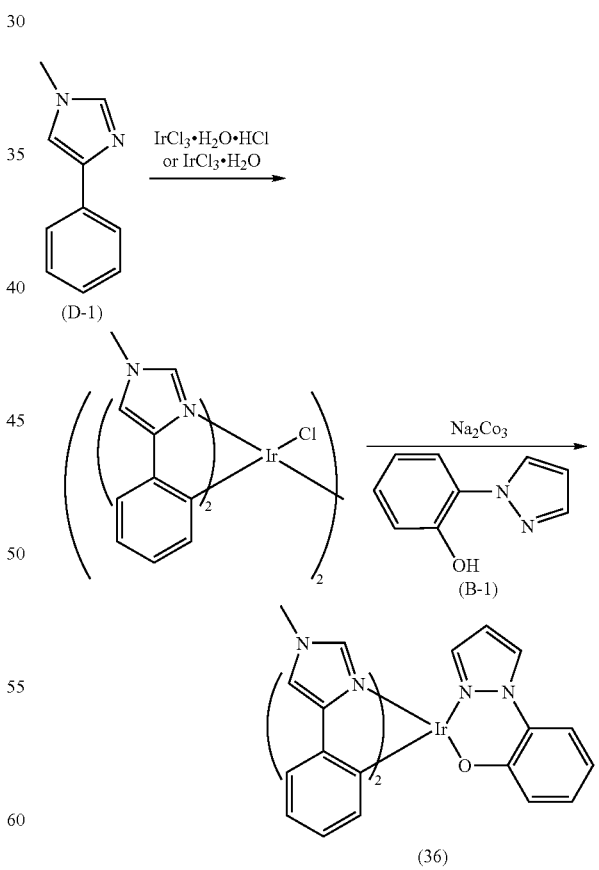

(36)

10 mL of ethylcellosolve was stirred in a nitrogen atmosphere at room temperature for 30 minutes, and 24.88 mmol of the compound of the compound (D-1) and 12.44 mmol of iridium (III) chloride were added thereto and heated while stirring for 24 hours and checking the progress of the reaction using TLC to determine if the reaction had completed. The reaction products were subjected to extraction using methylene chloride. The extracted methylene chloride phase was treated using MgSO₄ to remove water, filtered, and dried in a vacuum for 3 hours to obtain a dimmer with a yield of 44.5%.

10 mL of ethylcellosolve was stirred in a nitrogen atmosphere at room temperature for 30 minutes, 2.504 mmol of the dimer, 5.007 mmol of compound (B-1), and 5.508 mL of Na₂CO₃ as a base component were added thereto, followed by heating in a nitrogen atmosphere for 24 hours while stirring the mixture and checking the progress of the reaction using TLC to determine if the reaction had completed. As a result, the compound of formula (36) was obtained with a yield of 30%.

Figure 26:
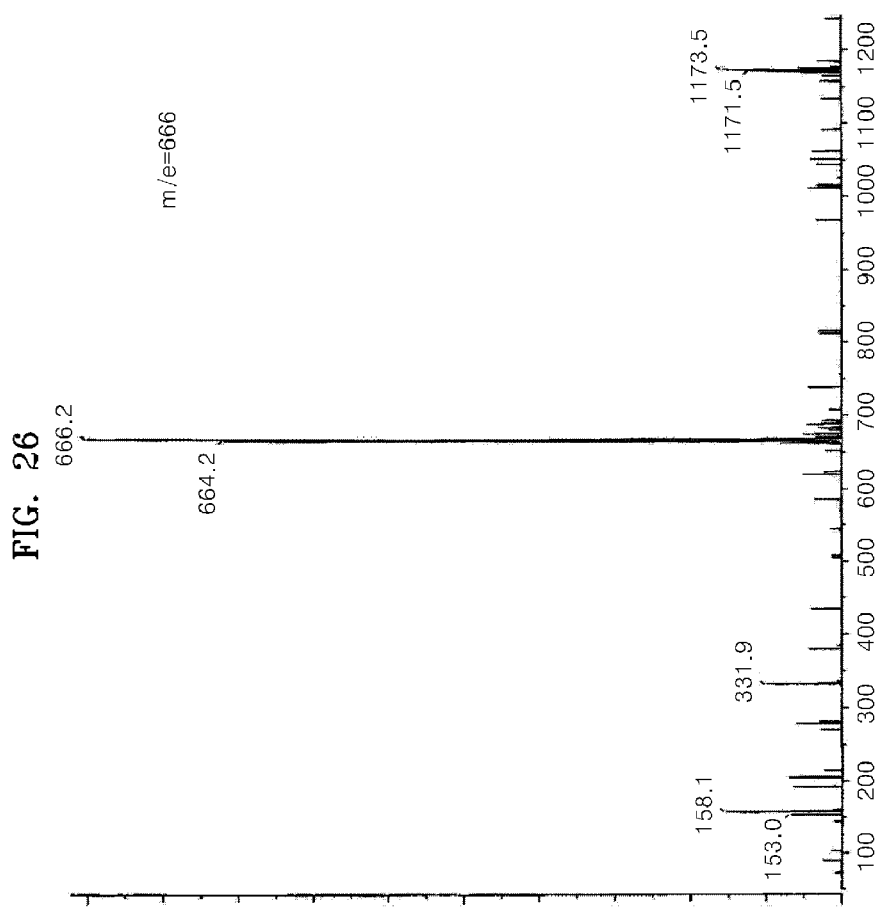
FIG. 26 is a graph illustrating the result of a mass analysis performed on an organic EL compound of formula (36) according to the embodiments of the present invention.
Figure 27:
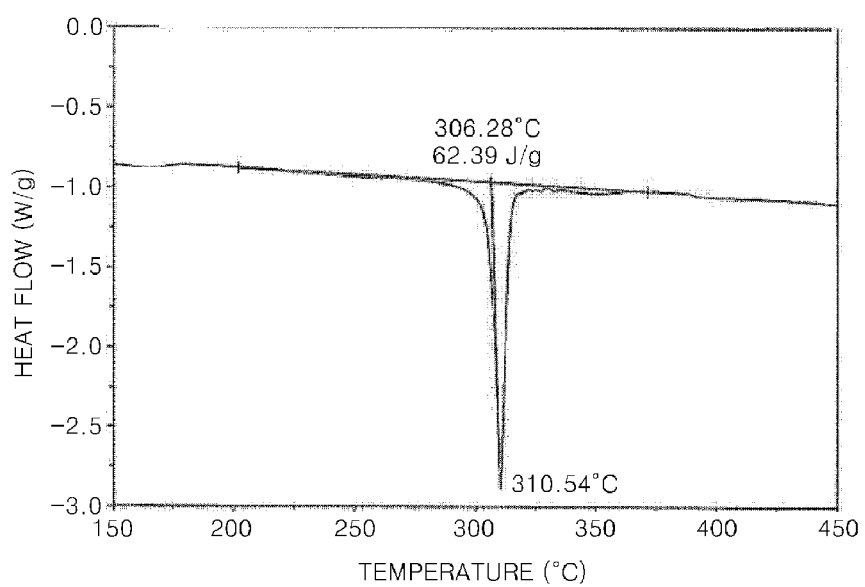
FIG. 27 is the DSC curve of the organic EL compound of formula (36) according to the embodiments of the present invention.

The mass of the compound of formula (36) was measured using mass spectrometry. The result is shown in FIG. 26. FIG. 27 is the DSC curve of the compound of formula (36). As shown in FIG. 27, the Tm of the compound of formula (36) is 306° C.

SYNTHESIS EXAMPLE 26

Synthesis of Compound (E-1)

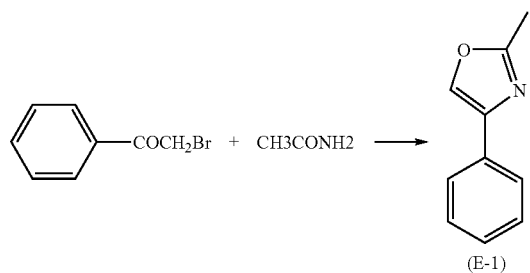

109.1 mmol of 2-bromoacetophenone and 218.2 mmol of acetoamide were reacted under reflux for 2 hours to obtain the compound (E-1) with a yield of 16.5%.

Figure 28:
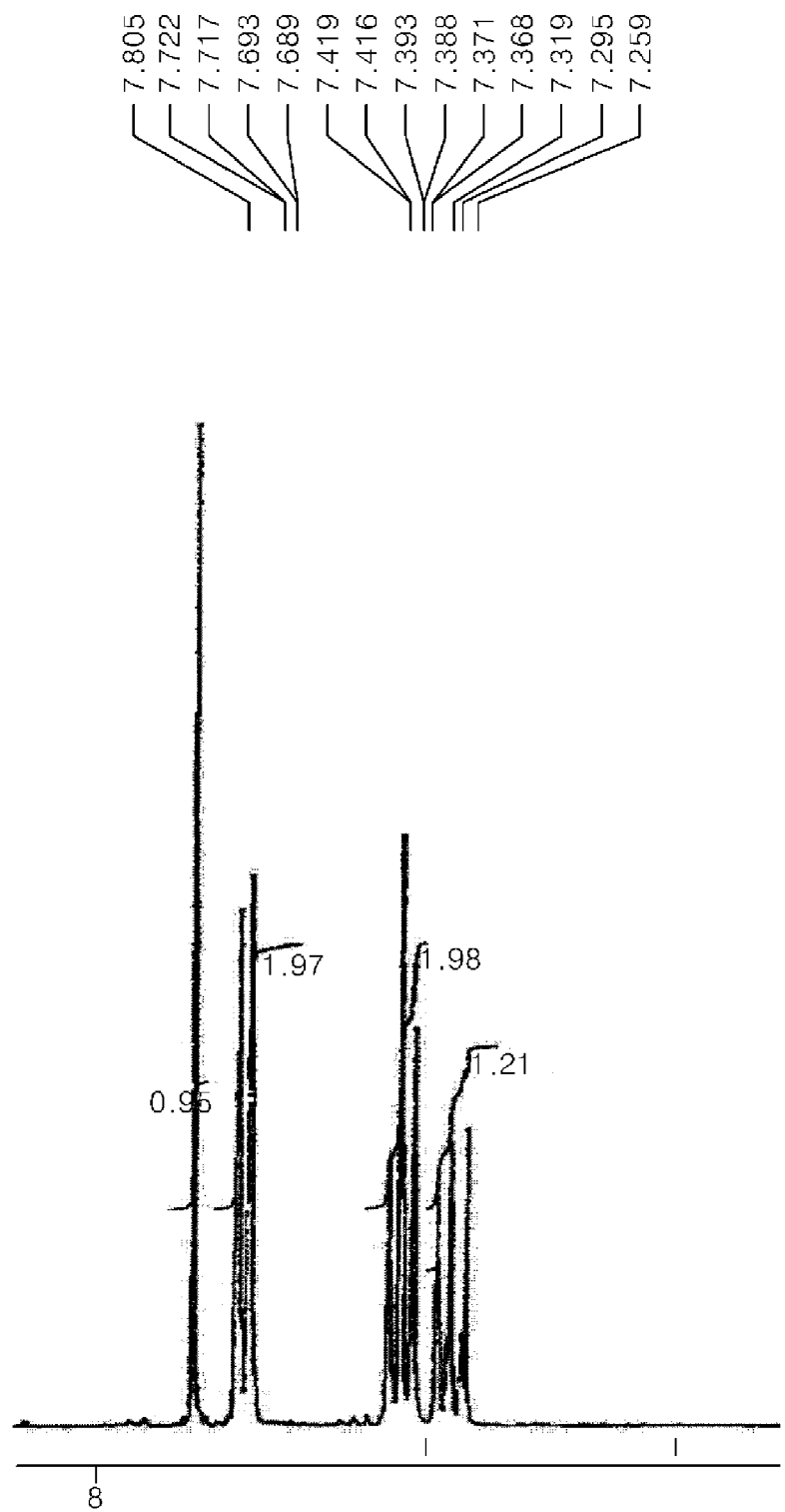
FIG. 28 is the NMR spectrum of a compound of formula (E-1) according to the embodiments of the present invention in CHCl₃ solution.

The structure of the compound (E-1) was identified using NMR. The result is shown in FIG. 28.

SYNTHESIS EXAMPLE 27

Synthesis of Compound of Formula (35

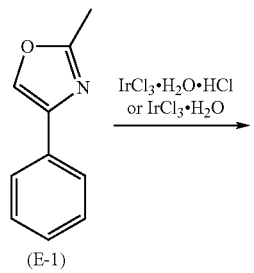

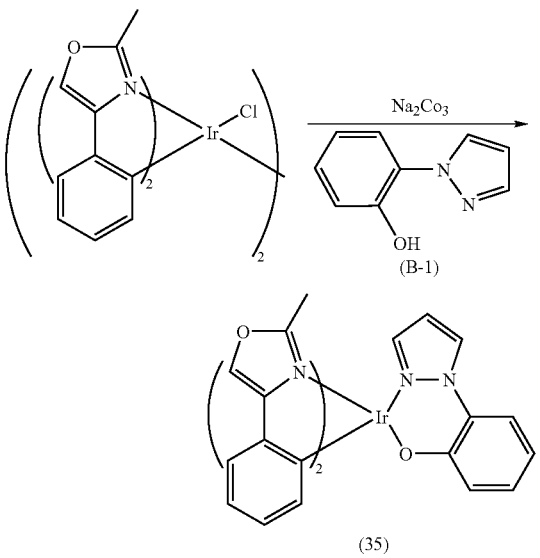

30 mL of ethylcellosolve was stirred in a nitrogen atmosphere at room temperature for 30 minutes, and 18 mmol of the compound of the compound (E-1) and 9 mmol of iridium (III) chloride were added thereto and heated while stirring for 24 hours and checking the progress of the reaction using TLC to determine if the reaction had completed. The reaction products were subjected to extraction using methylene chloride. The extracted methylene chloride phase was treated using MgSO₄ to remove water, filtered, and dried in a vacuum for 3 hours to obtain a dimer with a yield of 31.1%.

40 mL of ethylcellosolve was stirred in a nitrogen atmosphere at room temperature for 30 minutes, 1.345 mmol of the dimer, 2.69 mmol of compound (B-1), and 2.6 mmol of Na₂CO₃ as a base component were added thereto, followed by heating in a nitrogen atmosphere for 24 hours while stirring the mixture and checking the progress of the reaction using TLC to determine if the reaction had completed. As a result, the compound of formula (35) was obtained with a yield of 56.7%.

Figure 29:
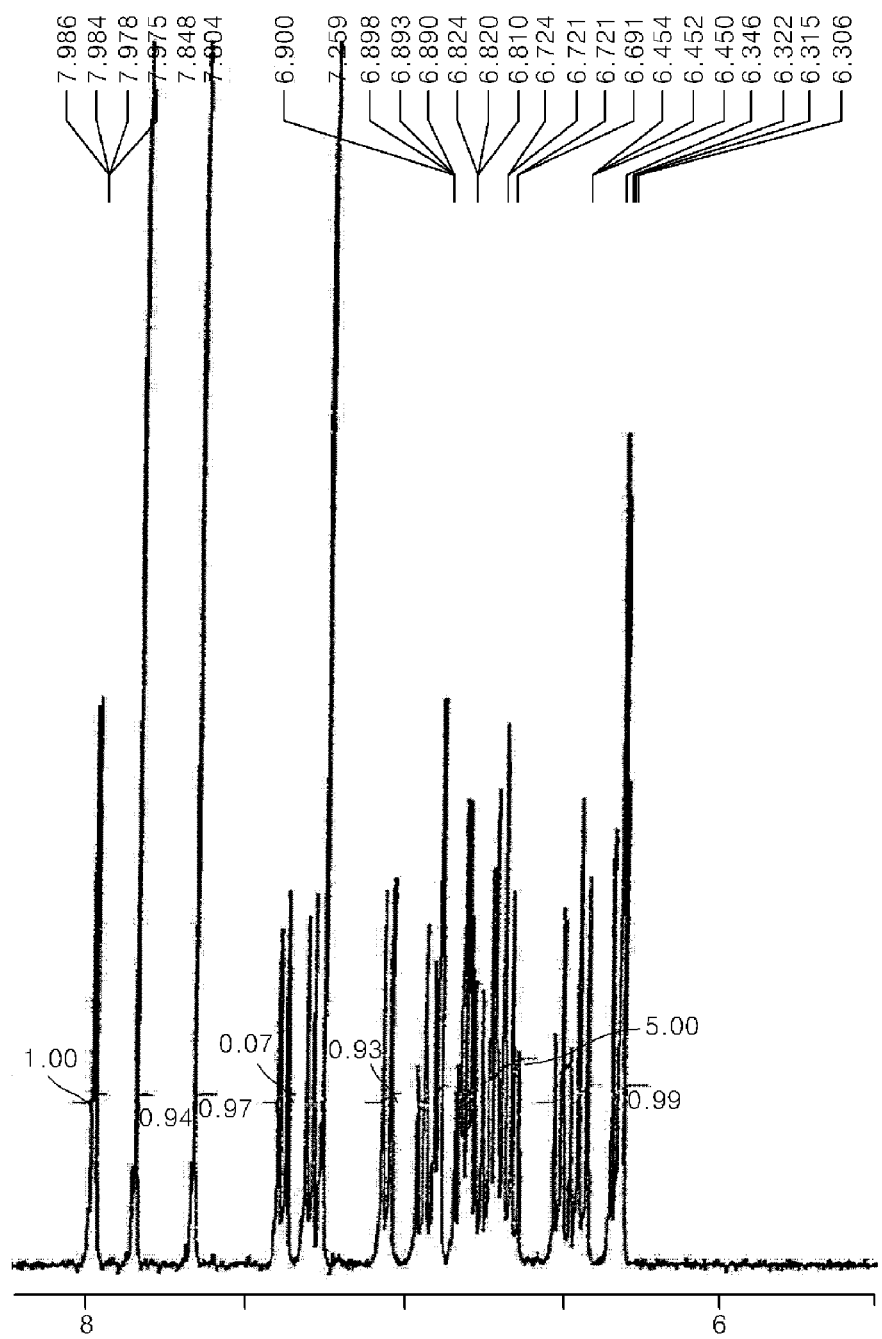
FIG. 29 is the NMR spectrum of an organic EL compound of formula (35) according to the embodiments of the present invention in CHCl₃ solution.
Figure 30:
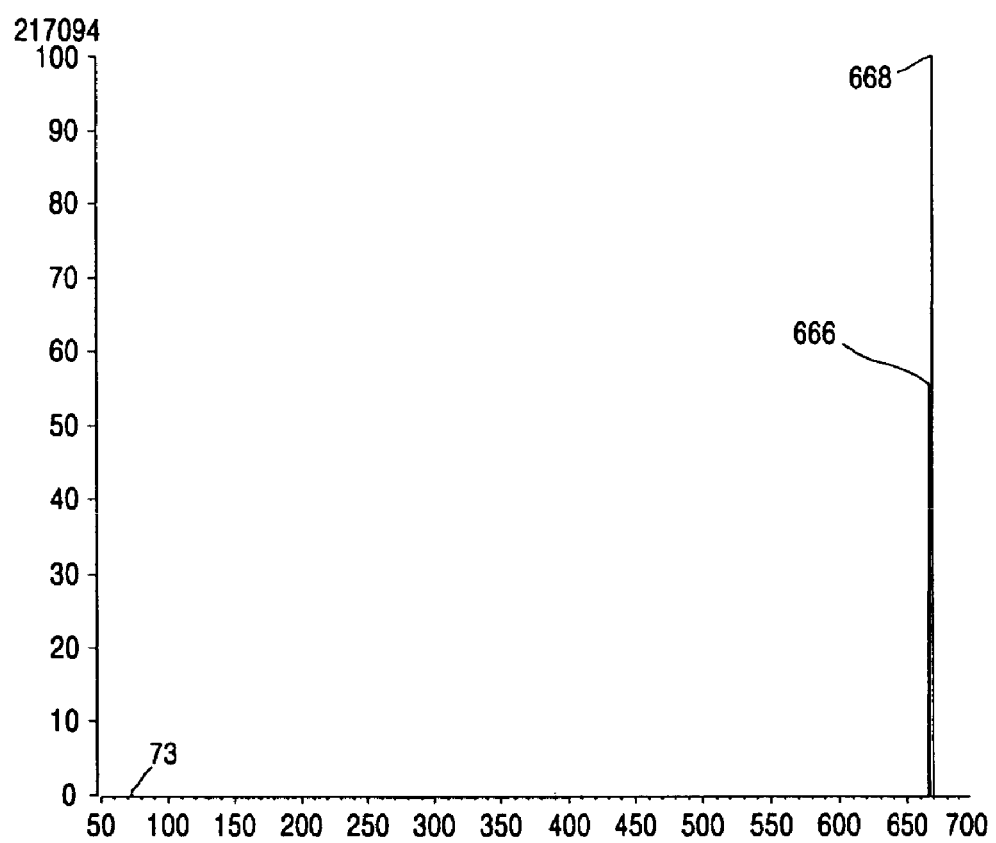
FIG. 30 is a graph illustrating the result of a mass analysis performed on the organic EL compound of formula (35) according to the embodiments of the present invention.
Figure 31:
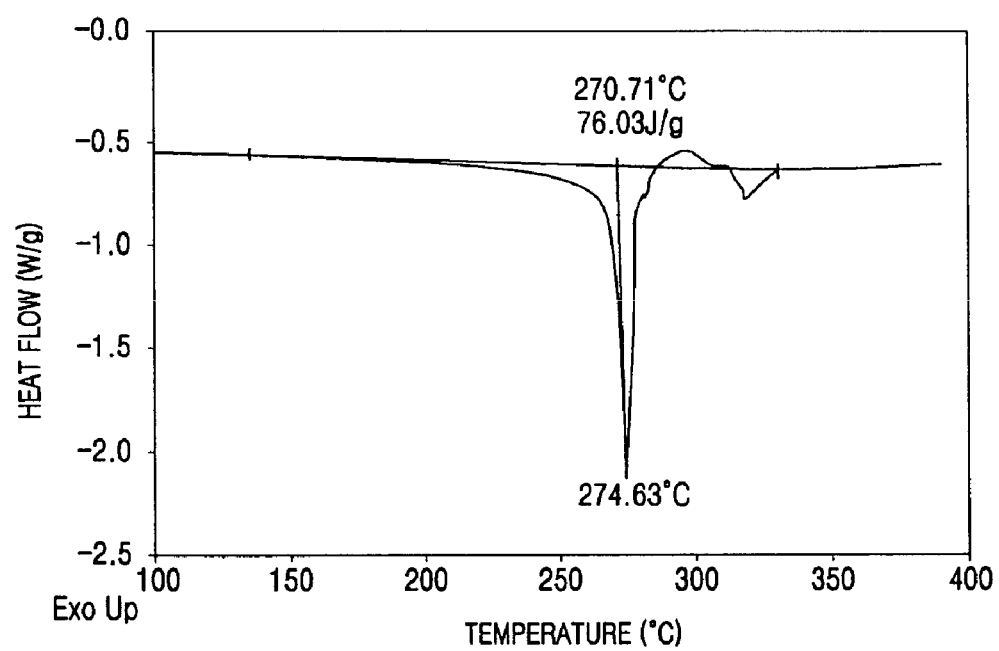
FIG. 31 is the DSC curve of the organic EL compound of formula (35) according to the embodiments of the present invention.

The structure and mass of the compound of formula (35) were analyzed using NMR and mass spectrometry, respectively. The results are shown in FIGS. 29 and 30. FIG. 31 is the DSC curve of the compound of formula (35). As shown in FIG. 31, the Tm of the compound of formula (31) is 271° C.

SYNTHESIS EXAMPLE 28

Synthesis of Compound (F-1)

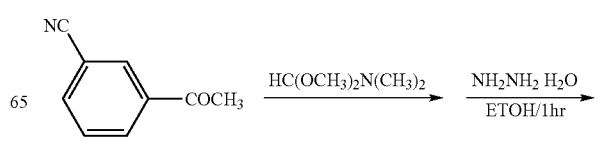

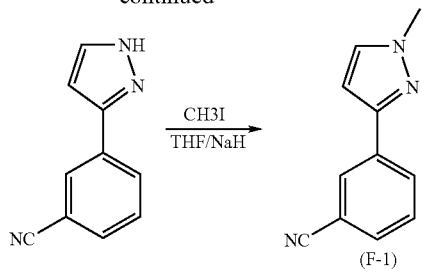

(F-1)

68.49 mmol of 3-cyanoacetophenone was mixed with 274 mmol of N,N-dimethylformamide and refluxed for 1 hour. 48.42 mmol of hydrazine monohydrate was added to the reaction product and refluxed for 1 hour using 100 mL of ethanol solvent. 61.51 mmol of NaH, 55.92 mmol of methyl iodide and 50 mL of THF were added to the reaction product and refluxed for 3 hours to obtain compound (F-1) with a yield of 48.8%.

Figure 32:
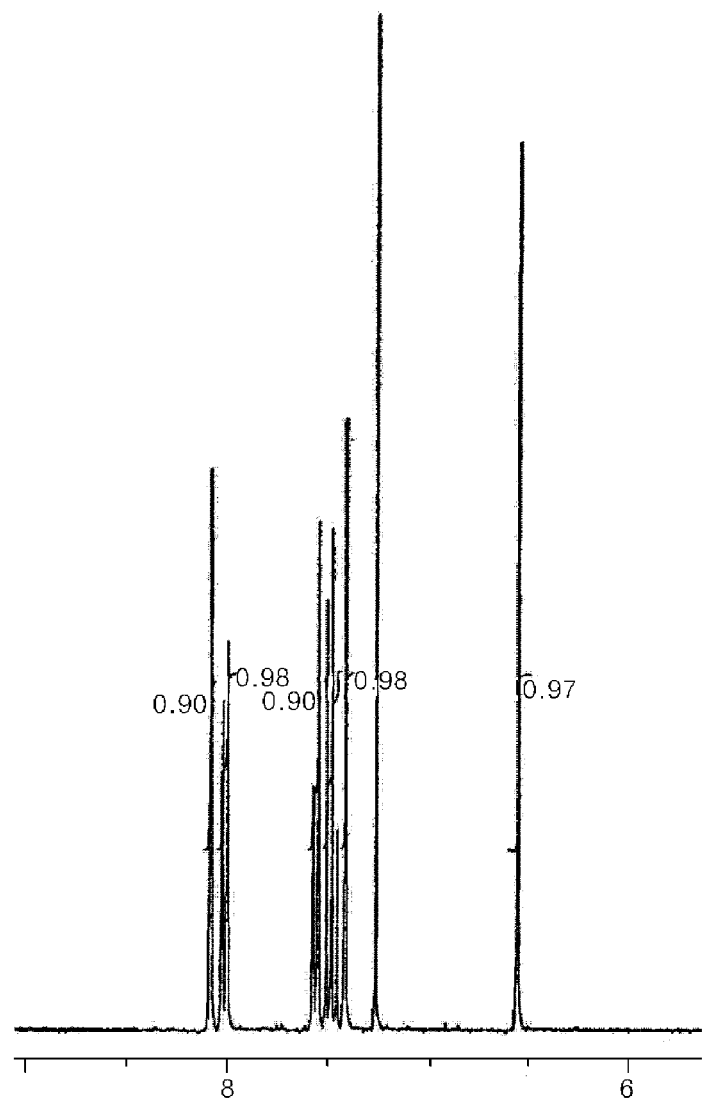
FIG. 32 is the NMR spectrum of a compound of formula (F-1) according to the embodiments of the present invention in CHCl₃ solution.
Figure 33:
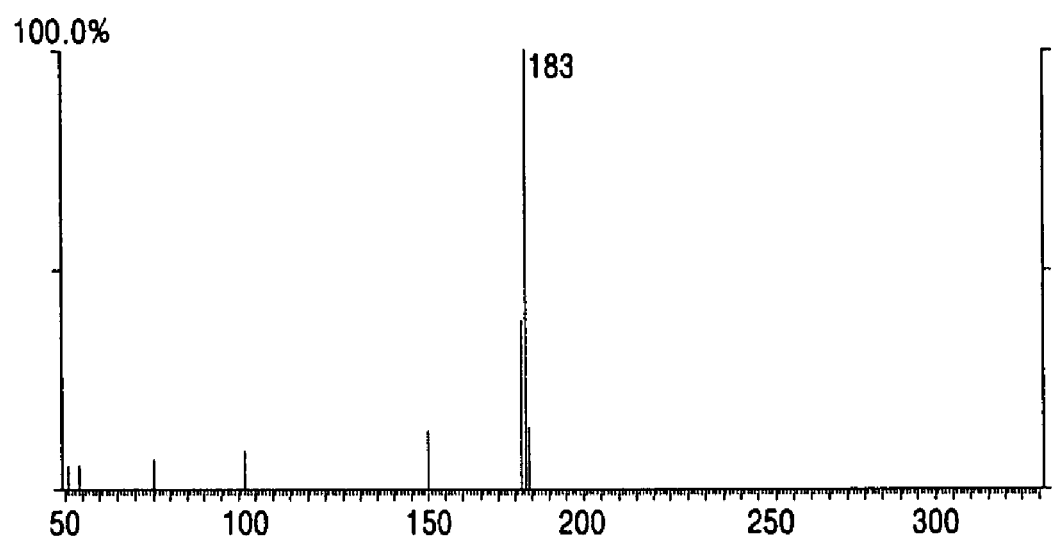
FIG. 33 is a graph illustrating the result of a mass analysis performed on the compound of formula (F-1) according to the embodiments of the present invention.

The structure and mass of the compound (F-1) were measured using NMR and mass spectrometry, respectively. The results are shown in FIGS. 32 and 33.

SYNTHESIS EXAMPLE 29

Synthesis of Compound of Formula (47)

The compound of formula (47) was synthesized in the same manner as in Synthesis Example 20, except that 1-phenylpyrazole, instead of compound (A-1), and 3-isoquinolinecarboxylate (3iq), instead of compound (B-1), were used.

SYNTHESIS EXAMPLE 30

Synthesis of Compound of Formula (48)

The compound of formula (48) was synthesized in the same manner as in Synthesis Example 20, except that 3-methyl-1-phenyl-1H-pyrazole, instead of compound (A-1), and 3-isoquinolinecarboxylate (3iq), instead of compound (B-1), were used.

SYNTHESIS EXAMPLE 31

Synthesis of Compound of Formula (49)

The compound of formula (49) was synthesized in the same manner as in Synthesis Example 20, except that 4-methyl-1-phenyl-1H-pyrazole (synthesized using a method disclosed in Korean Patent Application No. 2003-54778, the contents of which are incorporated by reference herein to the extent that they disclose that method), instead of compound (A-1), and 3-isoquinolinecarboxylate (3iq), instead of compound (B-1), were used.

SYNTHESIS EXAMPLE 32

Synthesis of Compound of Formula (50)

The compound of formula (50) was synthesized in the same manner as in Synthesis Example 20, except that 3,5-dimethyl-1-phenyl-1H-pyrazole (synthesized using a method disclosed in Korean Patent Application No. 2003-54778, the contents of which are incorporated by reference herein to the extent that they disclose that method), instead of compound (A-1), and 3-isoquinolinecarboxylate (3iq), instead of compound (B-1), were used.

SYNTHESIS EXAMPLE 33

Synthesis of Compound of Formula (51)

The compound of formula (51) was synthesized in the same manner as in Synthesis Example 20, except that 1-p-tolyl-1H-pyrazole (synthesized using a method disclosed in Korean Patent Application No. 2003-54778, the contents of which are incorporated by reference herein to the extent that they disclose that method), instead of compound (A-1), and 3-isoquinolinecarboxylate (3iq), instead of compound (B-1), were used.

SYNTHESIS EXAMPLE 34

Synthesis of Compound of Formula (52)

The compound of formula (52) was synthesized in the same manner as in Synthesis Example 20, except that 1-m-tolyl-1H-pyrazole (synthesized using a method disclosed in Korean Patent Application No. 2003-54778, the contents of which are incorporated by reference herein to the extent that they disclose that method), instead of compound (A-1), and 3-isoquinolinecarboxylate (3iq), instead of compound (B-1), were used.

SYNTHESIS EXAMPLE 35

Synthesis of Compound of Formula (53)

The compound of formula (53) was synthesized in the same manner as in Synthesis Example 20, except that 1-m-tolyl-1H-pyrazole (synthesized using a method disclosed in Korean Patent Application No. 2003-54778, the contents of which are incorporated by reference herein to the extent that they disclose that method), instead of compound (A-1), and 3-isoquinolinecarboxylate (3iq), instead of compound (B-1), were used.

SYNTHESIS EXAMPLE 36

Synthesis of Compound of Formula (54)

The compound of formula (54) was synthesized in the same manner as in Synthesis Example 20, except that 4-methyl-1-m-tolyl-1H-pyrazole (synthesized using a method disclosed in Korean Patent Application No. 2003-54778, the contents of which are incorporated by reference herein to the extent that they disclose that method), instead of compound (A-1), and 3-isoquinolinecarboxylate (3iq), instead of compound (B-1), were used.

SYNTHESIS EXAMPLE 37

Synthesis of Compound of Formula (55)

The compound of formula (55) was synthesized in the same manner as in Synthesis Example 20, except that 1-phenylpyrazole (synthesized using a method disclosed in Korean Patent Application No. 2003-54778, the contents of which are incorporated by reference herein to the extent that they disclose that method), instead of compound (A-1), and 1-isoquinolinecarboxylate (1iq), instead of compound (B-1), were used.

SYNTHESIS EXAMPLE 38

Synthesis of Compound of Formula (56)

The compound of formula (56) was synthesized in the same manner as in Synthesis Example 20, except that 3-methyl-1-phenyl-1H-pyrazole (synthesized using a method disclosed in Korean Patent Application No. 2003-54778, the contents of which are incorporated by reference herein to the extent that they disclose that method), instead of compound (A-1), and 1-isoquinolinecarboxylate (1iq), instead of compound (B-1), were used.

SYNTHESIS EXAMPLE 39

Synthesis of Compound of Formula (57)

The compound of formula (57) was synthesized in the same manner as in Synthesis Example 20, except that 4-methyl-1-phenyl-1H-lpyrazole (synthesized using a method disclosed in Korean Patent Application No. 2003-54778, the contents of which are incorporated by reference herein to the extent that they disclose that method), instead of compound (A-1), and 1-isoquinolinecarboxylate (1iq), instead of compound (B-1), were used.

SYNTHESIS EXAMPLE 40

Synthesis of Compound of Formula (58)

The compound of formula (58) was synthesized in the same manner as in Synthesis Example 20, except that 3,5-dimethyl-phenylpyrazole (synthesized using a method disclosed in Korean Patent Application No. 2003-54778, the contents of which are incorporated by reference herein to the extent that they disclose that method), instead of compound (A-1), and 1-isoquinolinecarboxylate (1iq), instead of compound (B-1), were used.

SYNTHESIS EXAMPLE 41

Synthesis of Compound of Formula (59)

The compound of formula (59) was synthesized in the same manner as in Synthesis Example 20, except that 1-o-tolyl-1H-pyrazole (synthesized using a method disclosed in Korean Patent Application No. 2003-54778, the contents of which are incorporated by reference herein to the extent that they disclose that method), instead of compound (A-1), and 1-isoquinolinecarboxylate (1iq), instead of compound (B-1), were used.

SYNTHESIS EXAMPLE 42

Synthesis of Compound of Formula (60)

The compound of formula (60) was synthesized in the same manner as in Synthesis Example 20, except that 1-m-tolyl-1H-pyrazole (synthesized using a method disclosed in Korean Patent Application No. 2003-54778, the contents of which are incorporated by reference herein to the extent that they disclose that method), instead of compound (A-1), and 1-isoquinolinecarboxylate (1iq), instead of compound (B-1), were used.

SYNTHESIS EXAMPLE 43

Synthesis of Compound of Formula (61)

The compound of formula (61) was synthesized in the same manner as in Synthesis Example 20, except that 1-p-tolyl-1H-pyrazole (synthesized using a method disclosed in Korean Patent Application No. 2003-54778, the contents of which are incorporated by reference herein to the extent that they disclose that method), instead of compound (A-1), and 1-isoquinolinecarboxylate (1iq), instead of compound (B-1), were used.

SYNTHESIS EXAMPLE 44

Synthesis of Compound of Formula (62)

The compound of formula (62) was synthesized in the same manner as in Synthesis Example 20, except that 4-methyl-1-m-tolyl-1H-pyrazole (synthesized using a method disclosed in Korean Patent Application No. 2003-54778, the contents of which are incorporated by reference herein to the extent that they disclose that method), instead of compound (A-1), and 1-isoquinolinecarboxylate (1iq), instead of compound (B-1), were used.

The photoluminescence spectra of the compounds obtained in the synthesis examples were measured. The results are summarized in Table 1 below.

TABLE 1

| Compound | PL (nm) |
| --- | --- |
| formula (36) | 420 |
| formula (47) | 532 |
| formula (48) | 544 |
| formula (49) | 537 |
| formula (50) | 555 |
| formula (51) | 542 |
| formula (52) | 553 |
| formula (53) | 540 |
| formula (54) | 558 |
| formula (55) | 574 |
| formula (56) | 587 |
| formula (57) | 575 |
| formula (58) | 599 |
| formula (59) | 582 |
| formula (60) | 594 |
| formula (61) | 577 |
| formula (62) | 603 |

EXAMPLE 1

An indium tin oxide (ITO) substrate (available from Corning Co.) having a resistance of 10 $\Omega/cm^2$ was used for an anode. A hole injecting layer was formed of IDE 406 on the anode to a thickness of 600 Å by vacuum deposition. Next, a hole transporting layer was formed on the hole injecting layer by depositing N,N'-bis(3-methylphenyl)-N,N'-diphenyl-[1,1-biphenyl]-4,4'-diamine (TPD) in a vacuum to a thickness of 300 Å. An emissive layer was formed on the hole transporting layer by spin coating 4,4'-bis(carbazol-9-yl)-biphenyl (CBP) to a thickness of 200 Å.

A hole barrier layer was formed on the emissive layer by depositing BCP in a vacuum to a thickness of 50 Å. An electron transporting layer was formed on the hole barrier layer by depositing Alq3 in a vacuum to a thickness of 200 Å. Finally, a LiF/Al electrode was formed on the electron transporting layer by sequentially depositing LiF to a thickness of 10 Å and Al to a thickness of 3,000 Å in a vacuum, thereby resulting in a complete organic EL device.

The luminance, chromaticity coordinate, and efficiency of the organic EL device manufactured in Example 1 were measured. As a result, it was found that the organic EL device has greater efficiency, can operate at low voltage, and has a chromaticity coordinate that provides optimal blue luminance.

EXAMPLE 2

An indium tin oxide (ITO) substrate (available from Corning Co.) having a resistance of 10 Ω/cm² was used for an anode. A hole injecting layer was formed of IDE 406 on the anode to a thickness of 600 Å by vacuum deposition. Next, a hole transporting layer was formed on the hole injecting layer by depositing N,N'-bis(3-methylphenyl)-N, N'-diphenyl-[1,1-biphenyl]-4,4'-diamine (TPD) in a vacuum to a thickness of 300 Å. An emissive layer was formed on the hole transporting layer by spin coating the compound of formula (33) to a thickness of 200 Å.

A hole barrier layer was formed on the emissive layer by depositing BCP in a vacuum to a thickness of 50 Å. An electron transporting layer was formed on the hole barrier layer by depositing Alq3 in a vacuum to a thickness of 200 Å. Finally, a LiF/Al electrode was formed on the electron transporting layer by sequentially depositing LiF to a thickness of 10 Å and Al to a thickness of 3,000 Å in a vacuum, thereby resulting in a complete organic EL device.

The luminance, chromaticity coordinate, and efficiency of the organic EL device manufactured in Example 2 were measured. As a result, it was found that the organic EL device has greater efficiency, can operate at low voltage, and can be used as an effective organic EL material.

As described above, an iridium compound of formula (1) above according to the present invention cab emit deeper blue light than conventional blue phosphorescent materials and can improve color purity and reduce power consumption when used in an organic EL device. In addition, a metallic compound according to the embodiments of the present invention includes a novel bidentate of formula (31) above, can be synthesized with a high yield, and can be used as a full-color organic EL material for organic EL devices.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An iridium compound selected from the group consisting of compounds having formulas:

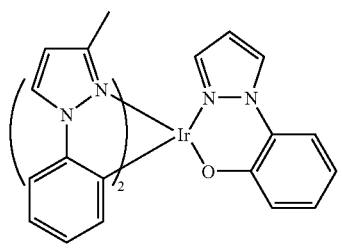

(12)

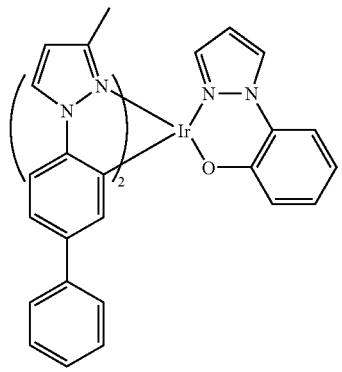

(13)

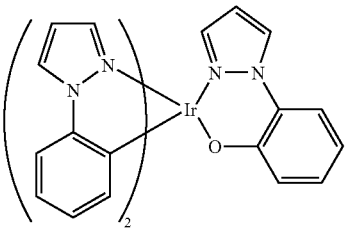

(16)

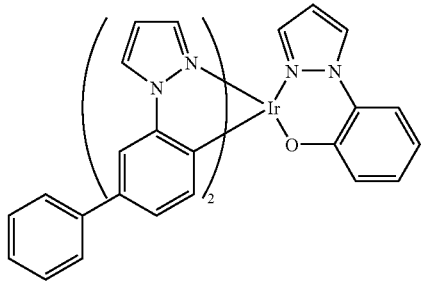

(17)

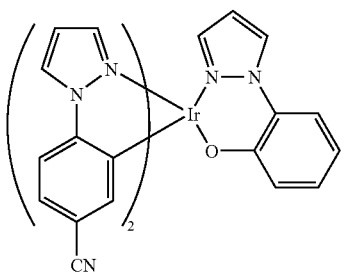

(18)

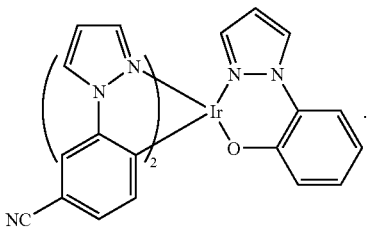

(19)

2. An organic electroluminescent device comprising an organic layer between a pair of electrodes, the organic layer including a compound according to claim 1.

3. An organic electroluminescent device of claim 2, wherein the organic layer is an emissive layer.

* * * * *